US008808379B2

(12) United States Patent
Abdou

(10) Patent No.: US 8,808,379 B2
(45) Date of Patent: Aug. 19, 2014

(54) SPINAL MOTION PRESERVATION DEVICES AND METHODS OF USE

(76) Inventor: M. Samy Abdou, San Diego, CA (US)

( * ) Notice: Subject to any disclaimer, the term of this patent is extended or adjusted under 35 U.S.C. 154(b) by 0 days.

(21) Appl. No.: 13/413,356

(22) Filed: Mar. 6, 2012

(65) Prior Publication Data

US 2012/0239090 A1 Sep. 20, 2012

Related U.S. Application Data

(63) Continuation of application No. 11/891,716, filed on Aug. 13, 2007, now abandoned.

(60) Provisional application No. 60/837,023, filed on Aug. 11, 2006, provisional application No. 60/842,697, filed on Sep. 6, 2006, provisional application No. 60/852,774, filed on Oct. 19, 2006, provisional application No. 60/874,195, filed on Dec. 11, 2006.

(51) Int. Cl.
*A61F 2/44* (2006.01)

(52) U.S. Cl.
USPC .......................................... 623/17.11; 606/246

(58) Field of Classification Search
USPC ..................... 606/246–279; 623/17.11–17.16
See application file for complete search history.

(56) References Cited

U.S. PATENT DOCUMENTS

| 4,759,769 A | 7/1988 | Hedman et al. |
| 4,790,303 A * | 12/1988 | Steffee .......................... 606/300 |
| 5,425,773 A | 6/1995 | Boyd et al. |
| 5,562,738 A | 10/1996 | Boyd et al. |
| 5,674,296 A | 10/1997 | Bryan |
| 5,676,701 A | 10/1997 | Yuan |
| 6,355,038 B1 | 3/2002 | Pisharodi |
| 6,770,096 B2 | 8/2004 | Bolger et al. |
| 6,921,403 B2 * | 7/2005 | Cragg et al. ................ 606/86 R |
| 7,083,622 B2 | 8/2006 | Simonson |
| 7,594,932 B2 | 9/2009 | Aferzon et al. |
| 7,727,280 B2 | 6/2010 | McLuen |
| 7,749,274 B2 | 7/2010 | Razian |
| 7,799,081 B2 | 9/2010 | McKinley |
| 2001/0039452 A1 | 11/2001 | Zucherman |
| 2003/0065395 A1 | 4/2003 | Ralph et al. |
| 2003/0078662 A1 | 4/2003 | Ralph et al. |
| 2003/0217809 A1 | 11/2003 | Yukio |
| 2004/0049280 A1 | 3/2004 | Cauthen |
| 2004/0073216 A1 * | 4/2004 | Lieberman ..................... 606/61 |
| 2004/0092933 A1 * | 5/2004 | Shaolian et al. ................ 606/61 |
| 2004/0143264 A1 | 7/2004 | McAfee |
| 2004/0225364 A1 | 11/2004 | Richelsoph et al. |
| 2004/0236425 A1 | 11/2004 | Huang |
| 2005/0033431 A1 | 2/2005 | Gordon et al. |

(Continued)

FOREIGN PATENT DOCUMENTS

| WO | WO 2007/140382 | 6/2007 |
| WO | WO 2007/095333 | 8/2007 |
| WO | WO 2008/021319 | 2/2008 |
| WO | WO 2008/073447 | 6/2008 |

*Primary Examiner* — Mary Hoffman
*Assistant Examiner* — Tara Carter
(74) *Attorney, Agent, or Firm* — Gazdzinski & Associates, PC

(57) ABSTRACT

Orthopedic implants are adapted to replace the function of a natural disc of the spine. In an embodiment, the implant can be placed across the disc space through a trans-pedicular corridor using a substantially posterior surgical approach. In another embodiment, an implant can be placed across the disc space at a different level through a substantially lateral or anterior approach.

22 Claims, 55 Drawing Sheets

(56) References Cited

U.S. PATENT DOCUMENTS

| | | |
|---|---|---|
| 2005/0043800 A1 | 2/2005 | Paul et al. |
| 2005/0071007 A1 | 3/2005 | Malek |
| 2005/0216083 A1 | 9/2005 | Michelson |
| 2006/0058791 A1* | 3/2006 | Broman et al. .......... 606/61 |
| 2006/0084988 A1 | 4/2006 | Kim |
| 2007/0106383 A1* | 5/2007 | Abdou .......... 623/17.11 |
| 2007/0161992 A1 | 7/2007 | Kwak |
| 2007/0191958 A1 | 8/2007 | Abdou |
| 2007/0282448 A1 | 12/2007 | Abdou |
| 2008/0281358 A1 | 11/2008 | Abdou |
| 2010/0087858 A1 | 4/2010 | Abdou |

* cited by examiner

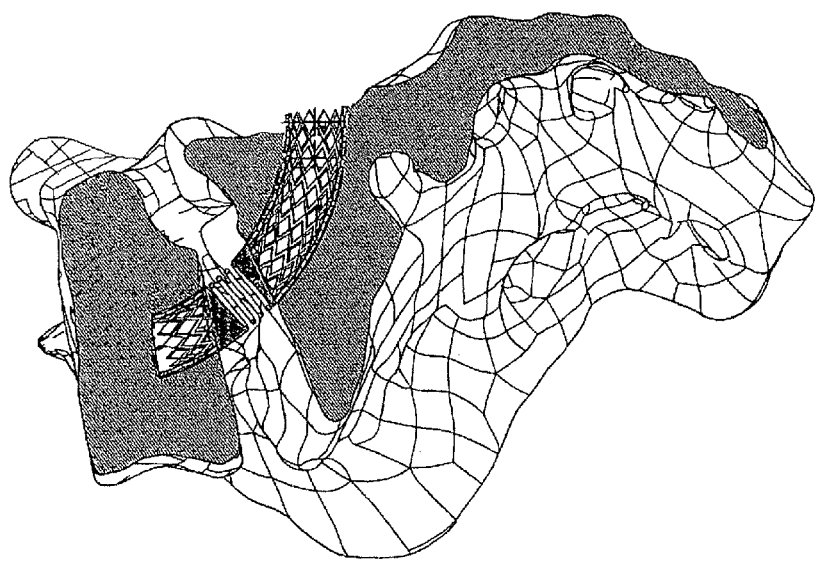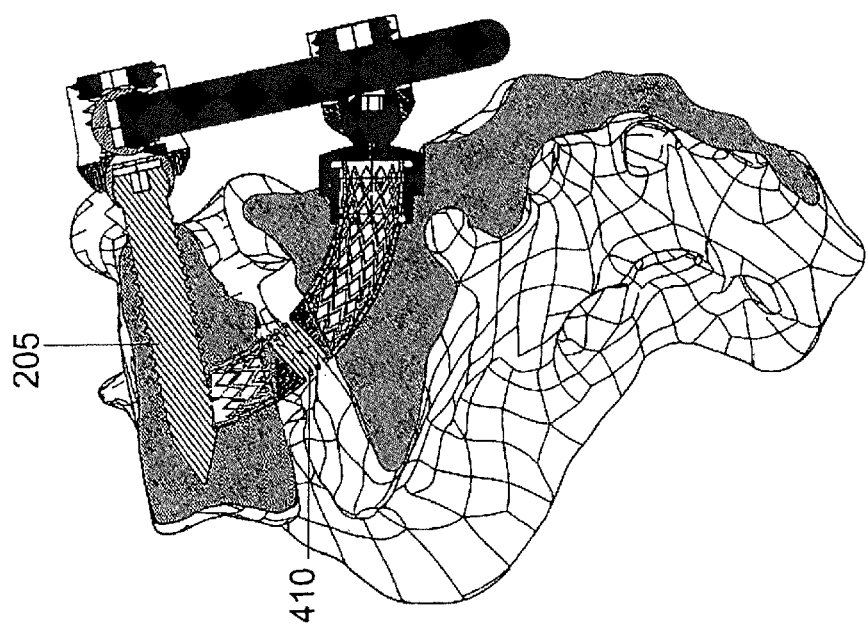
Fig. 5A
Fig. 5B

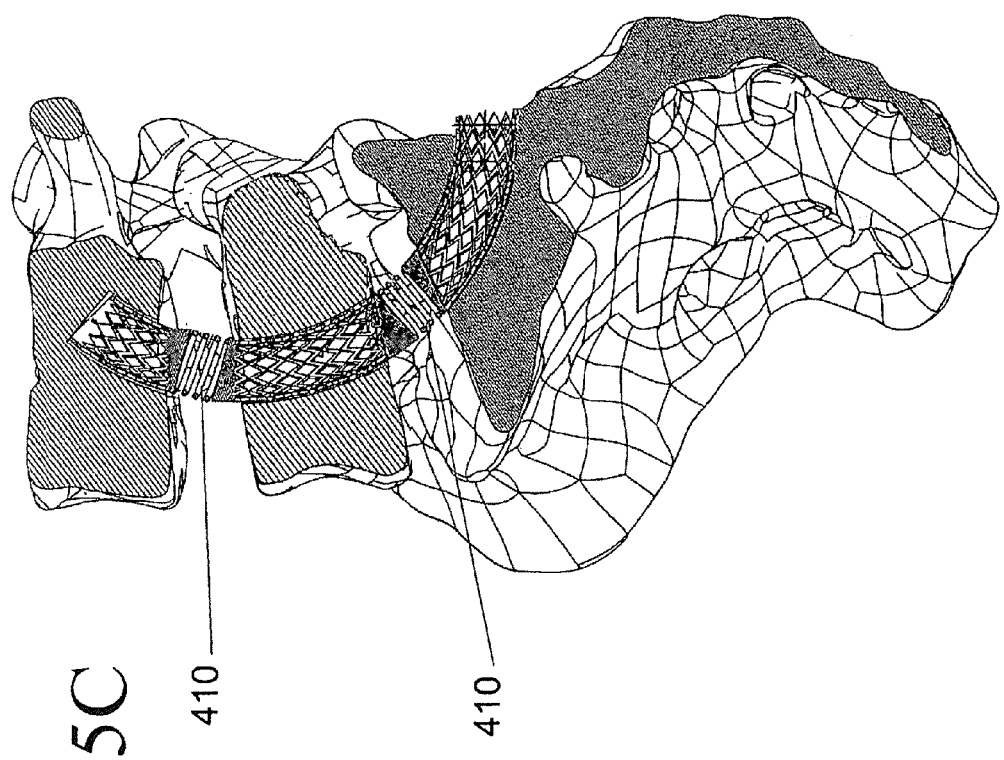

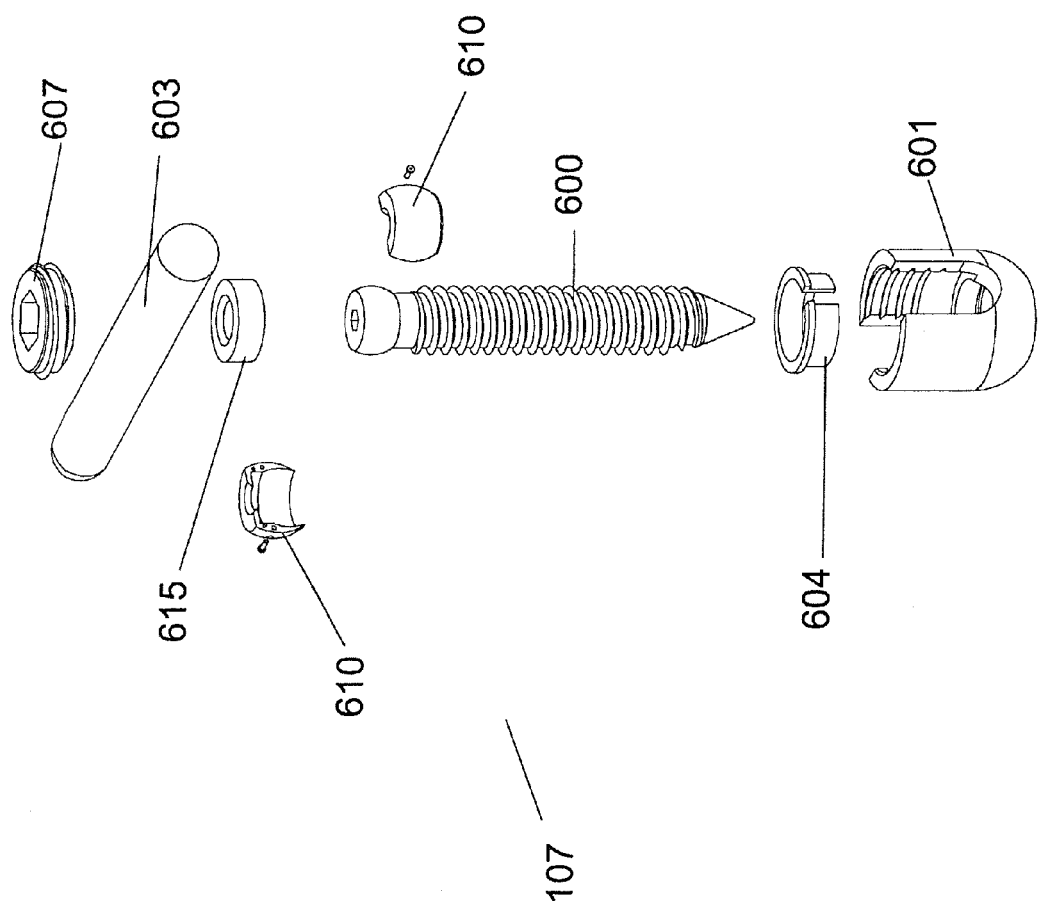

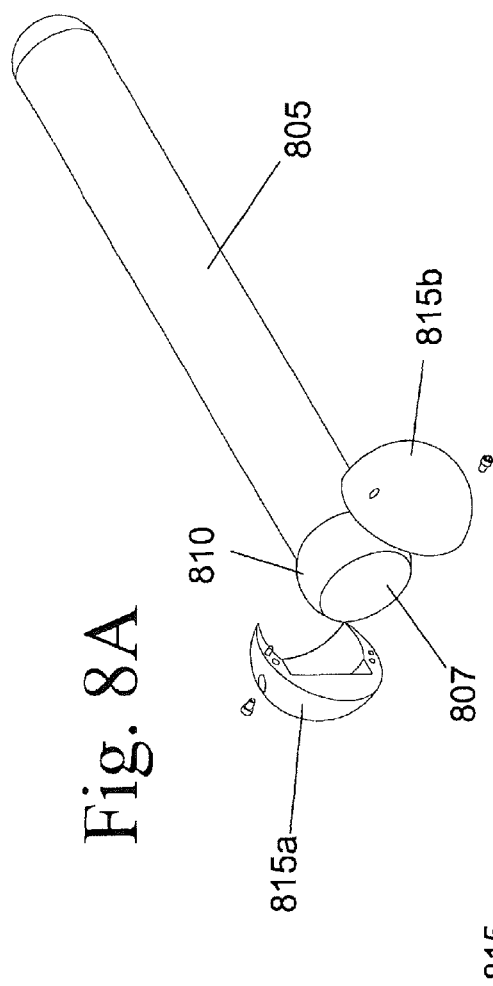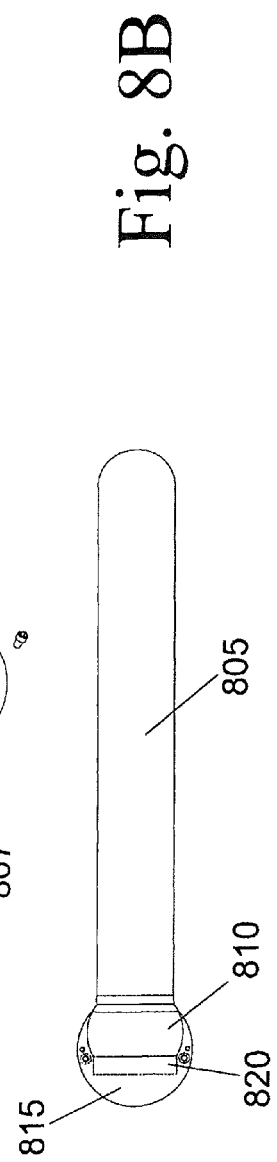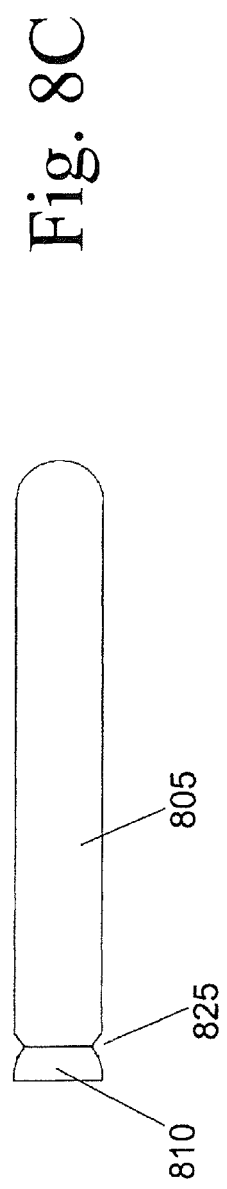

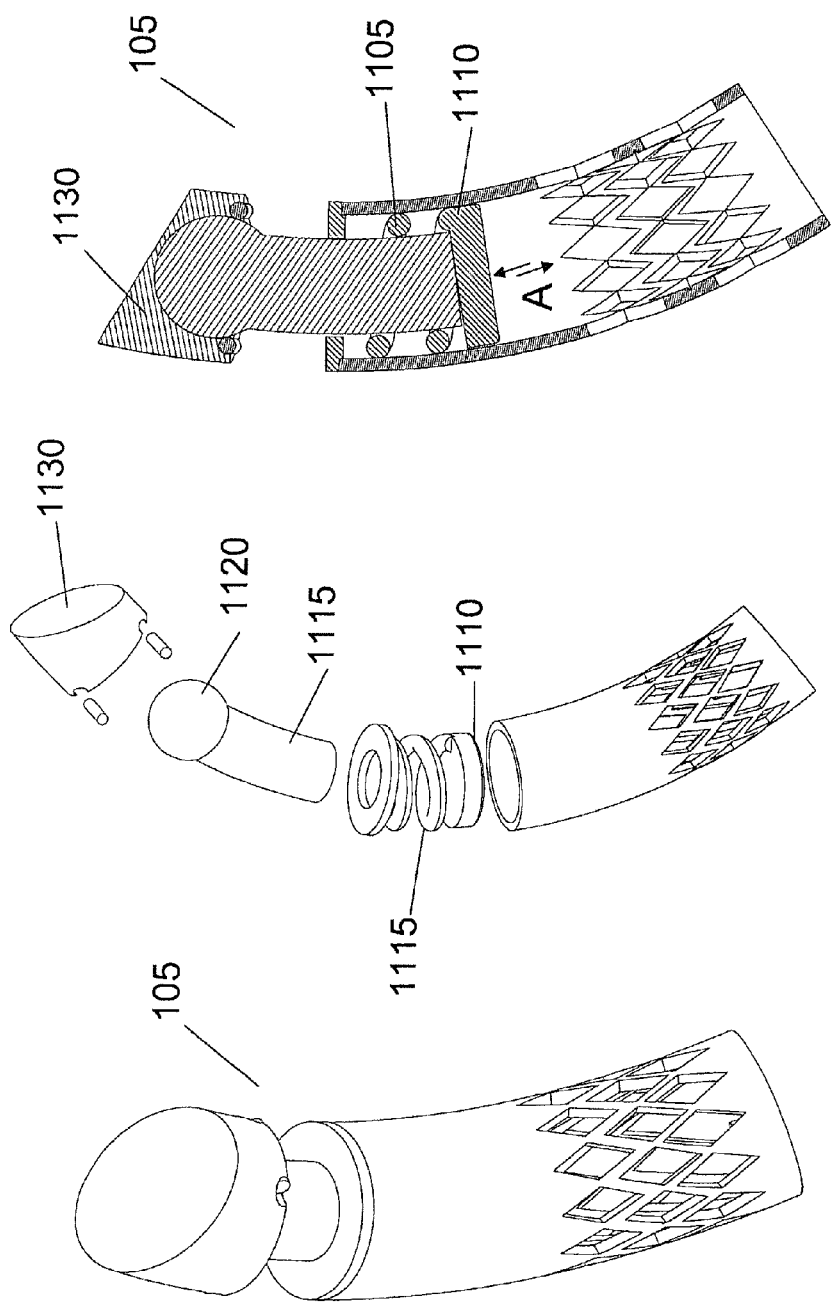

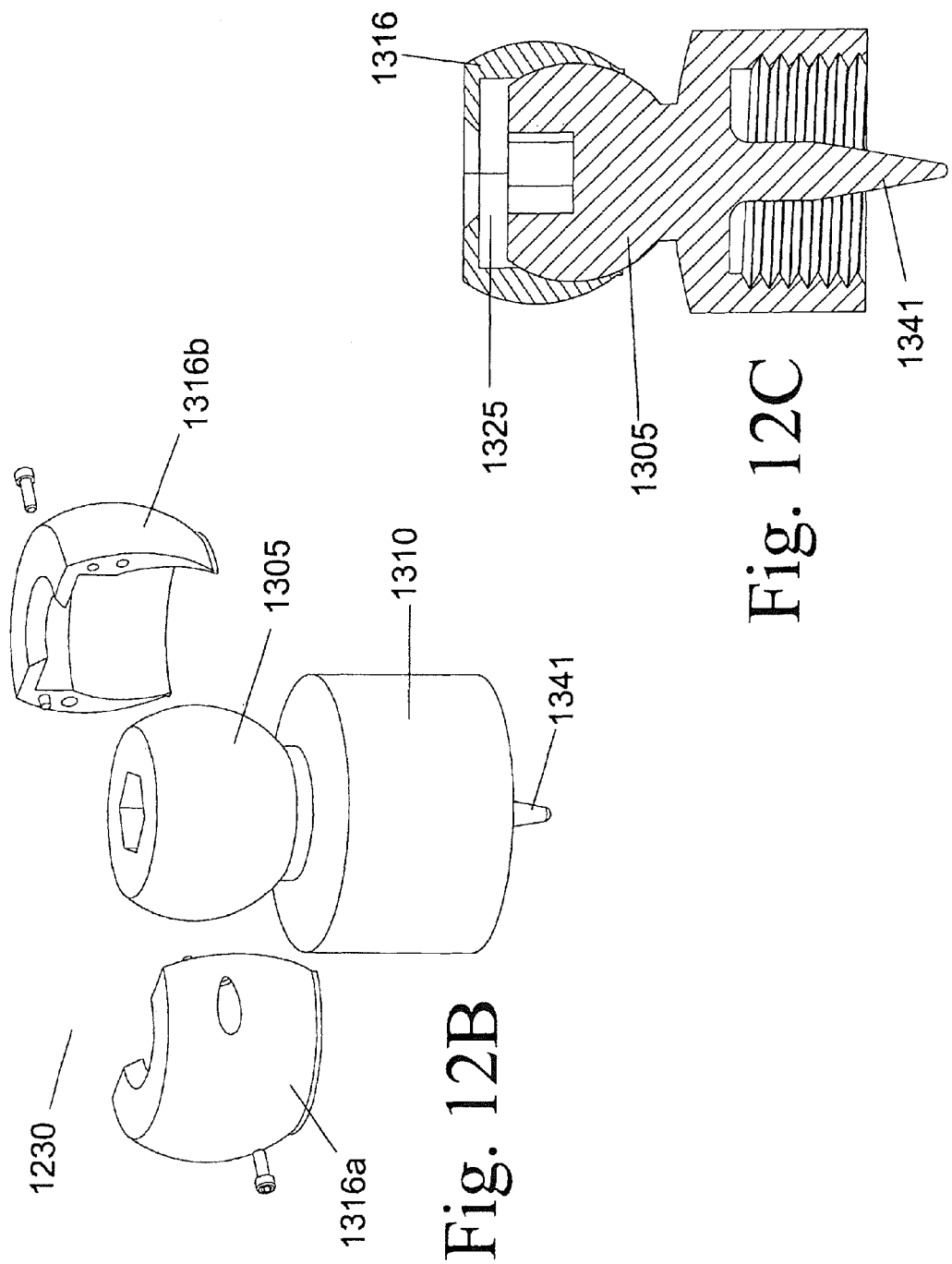

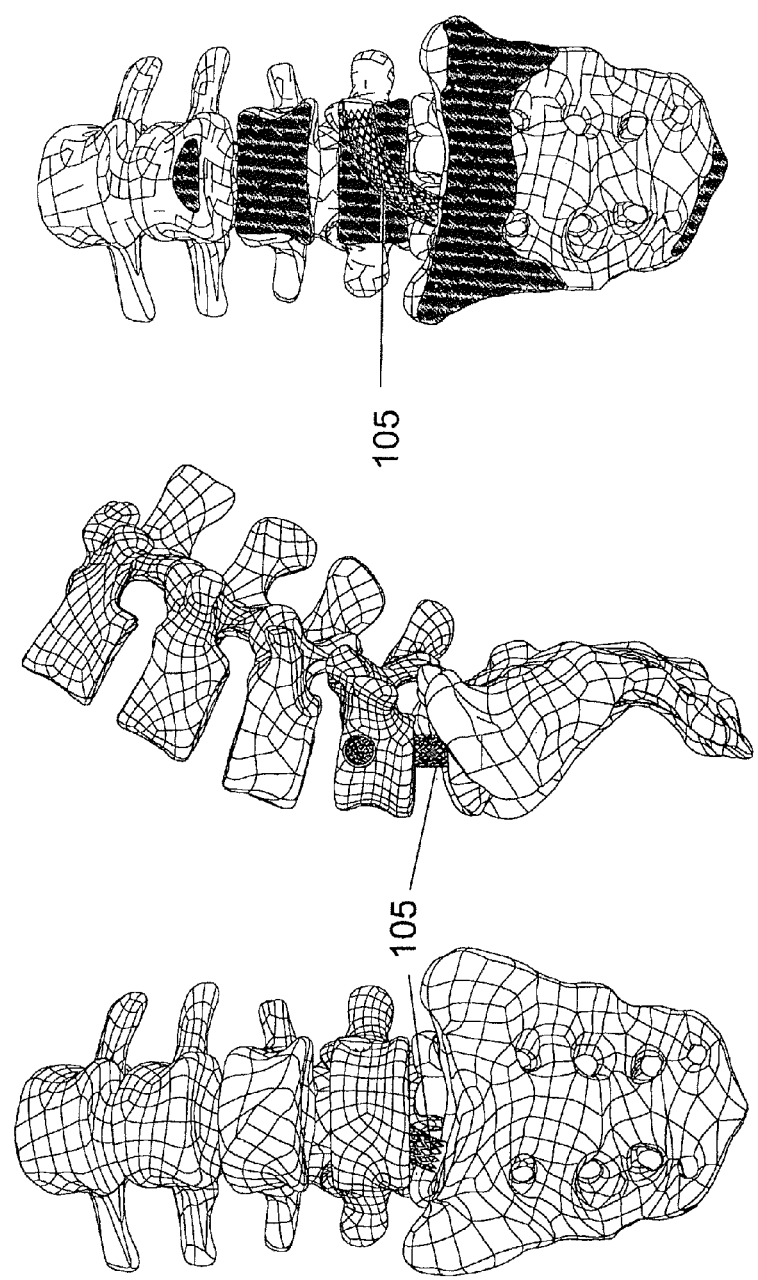

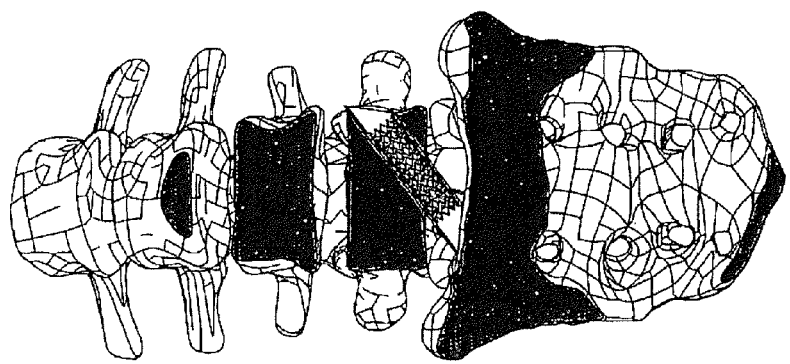
Fig. 13D
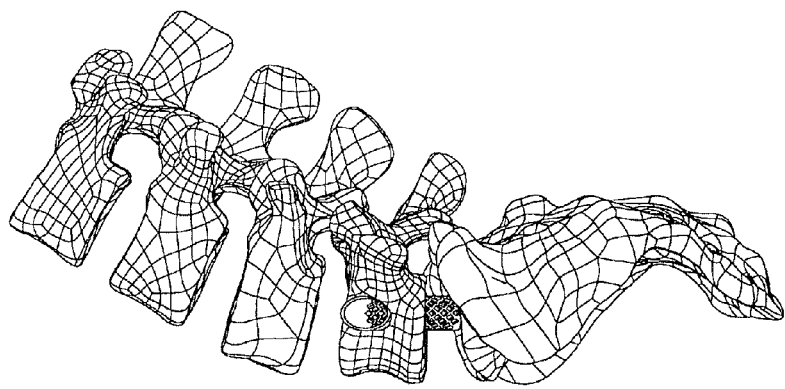
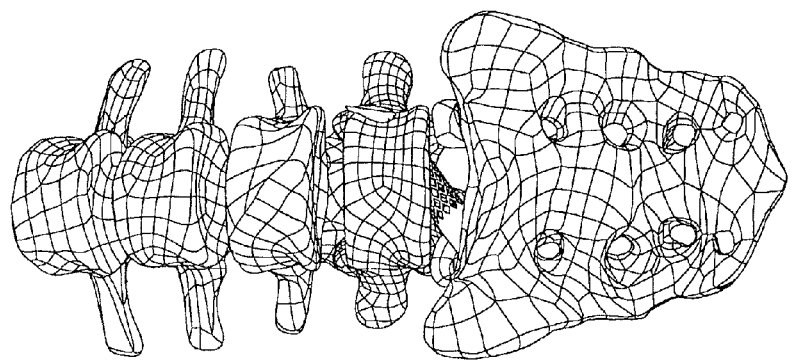
Fig. 13C

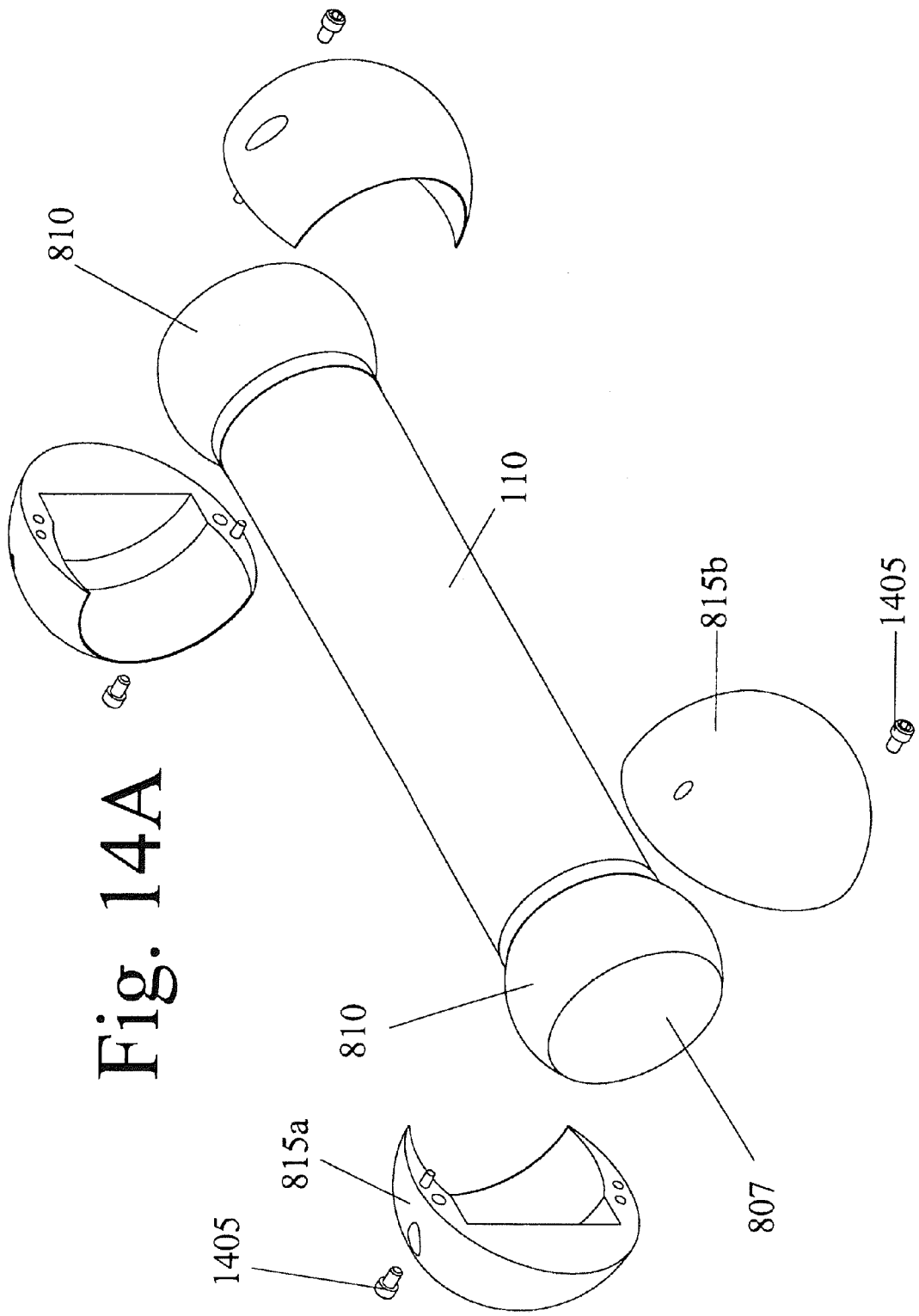

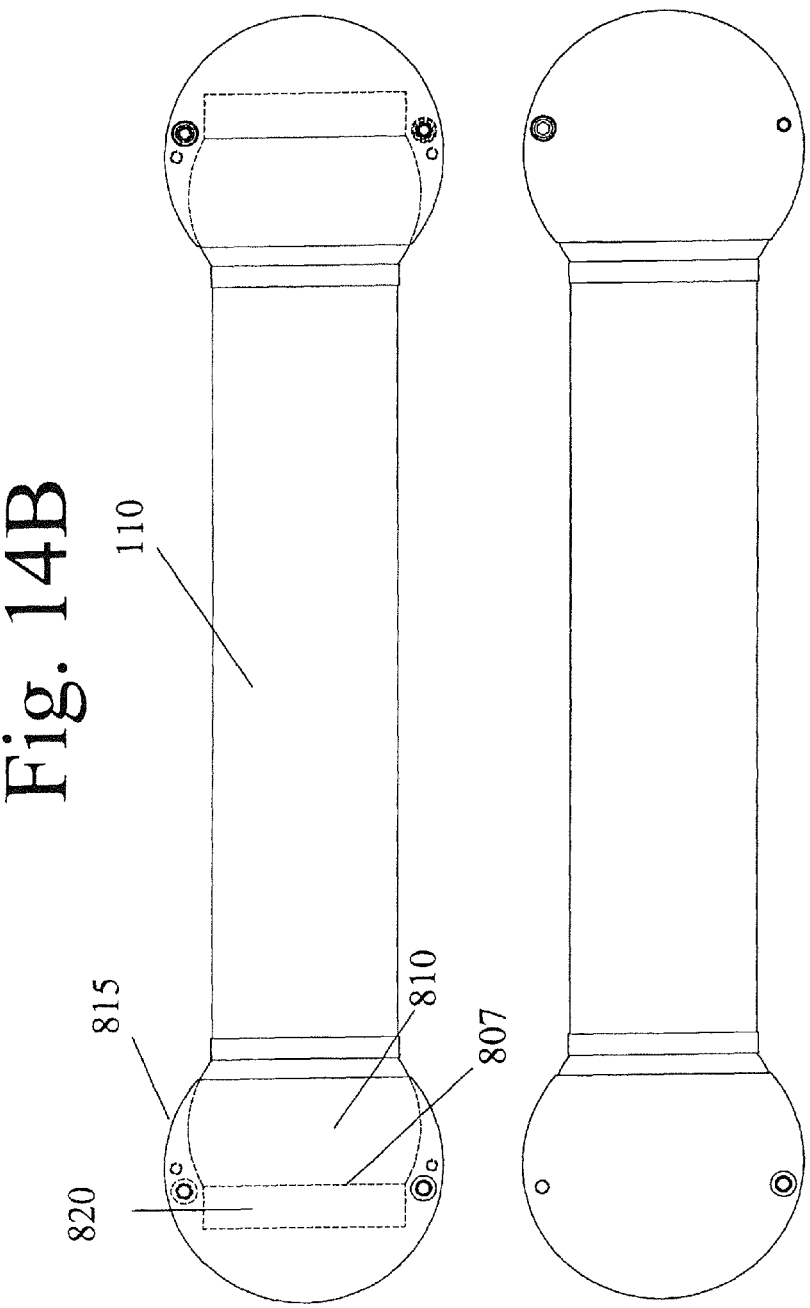

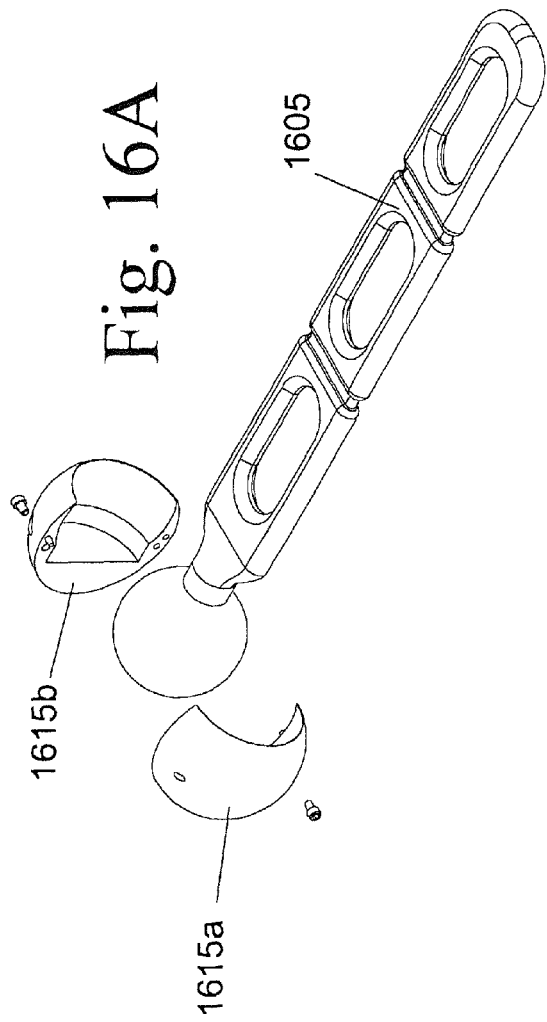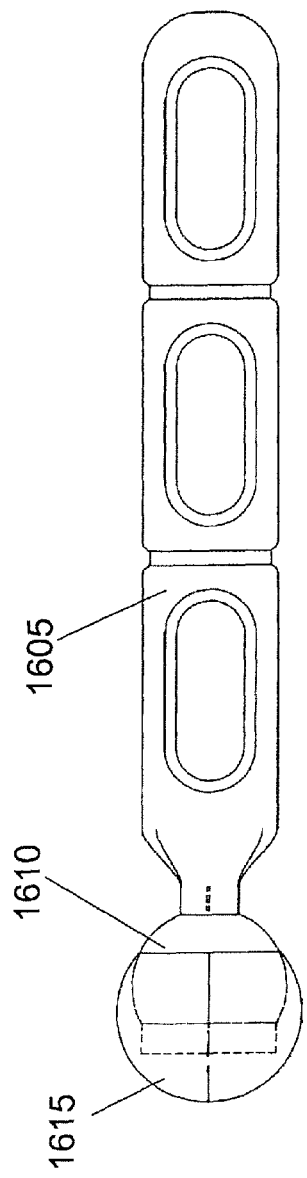
Fig. 16A
Fig. 16B

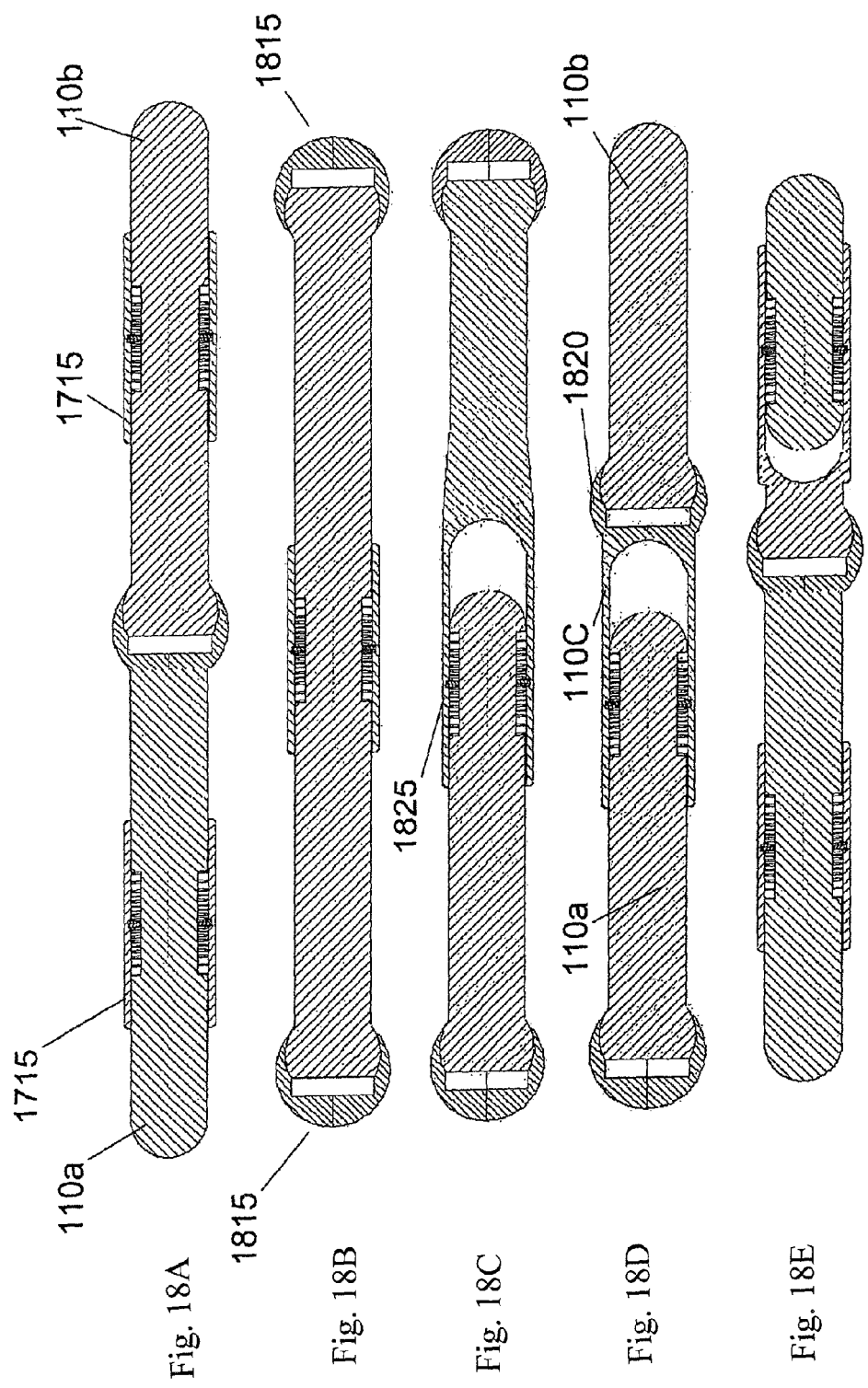

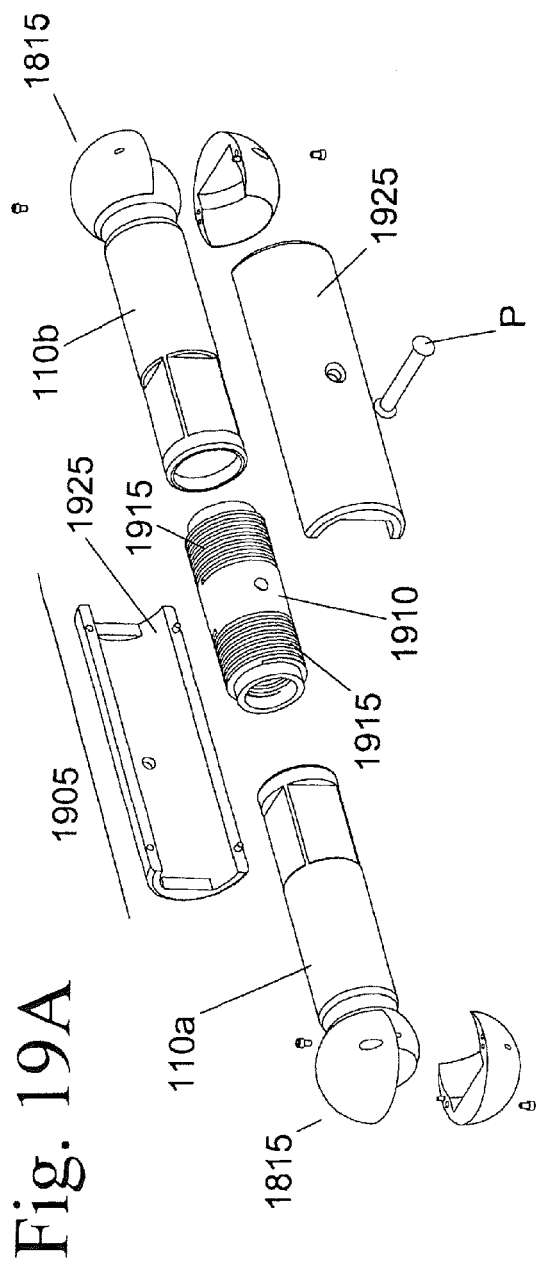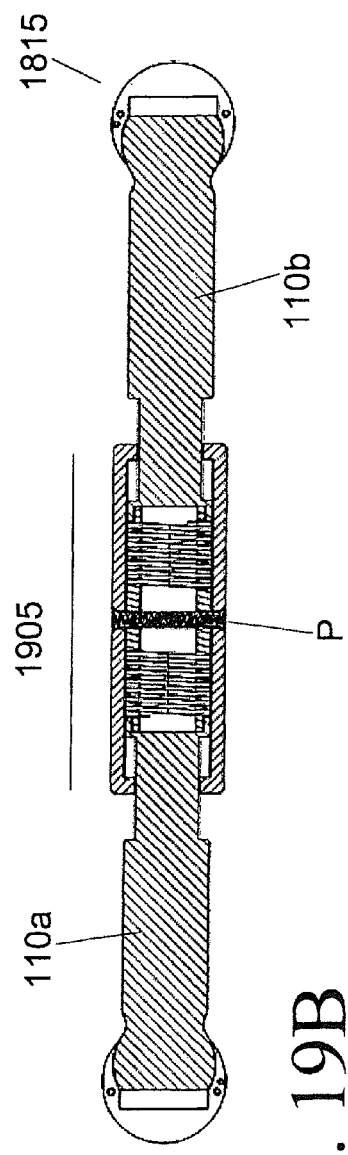
Fig. 19A
Fig. 19B

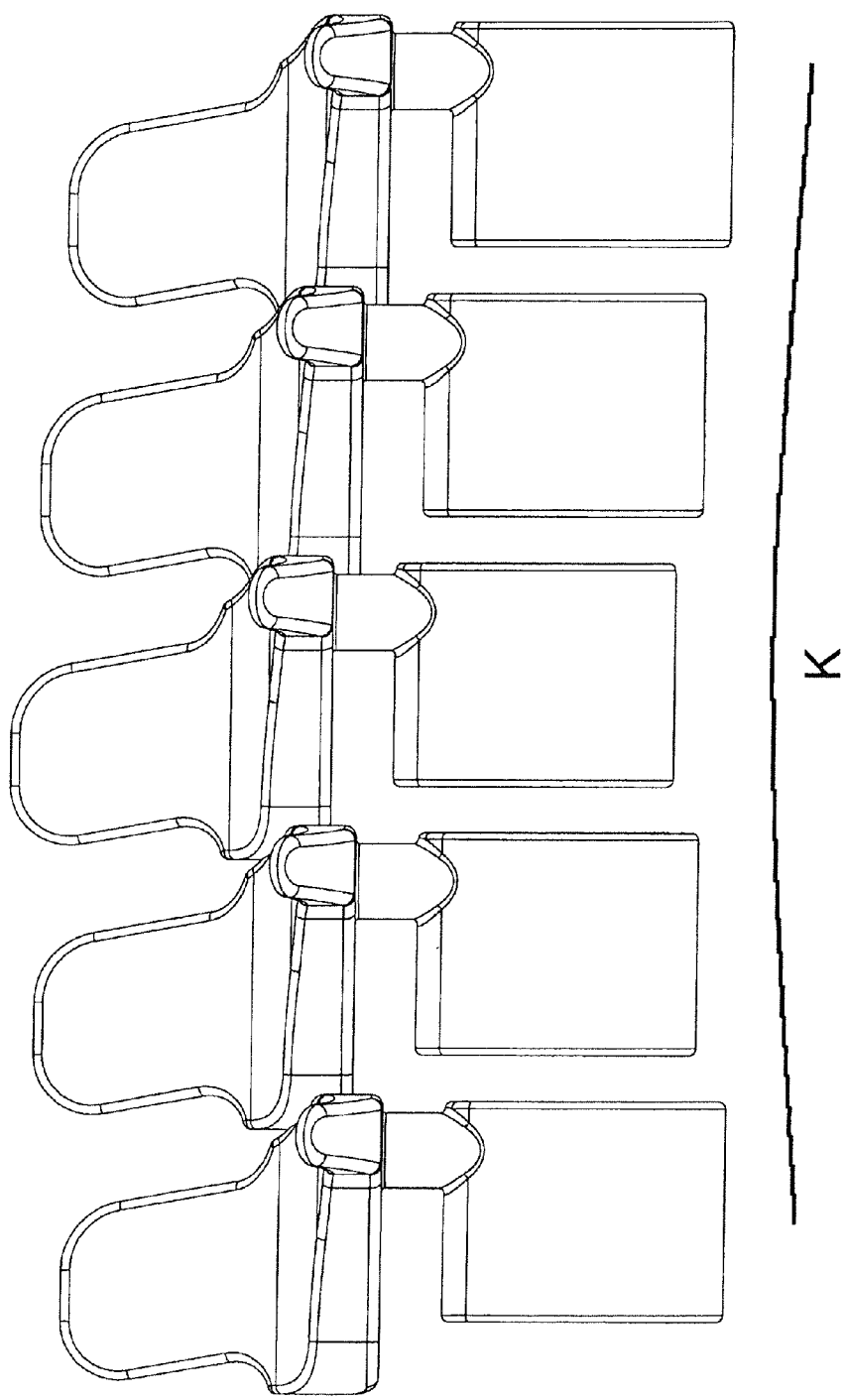

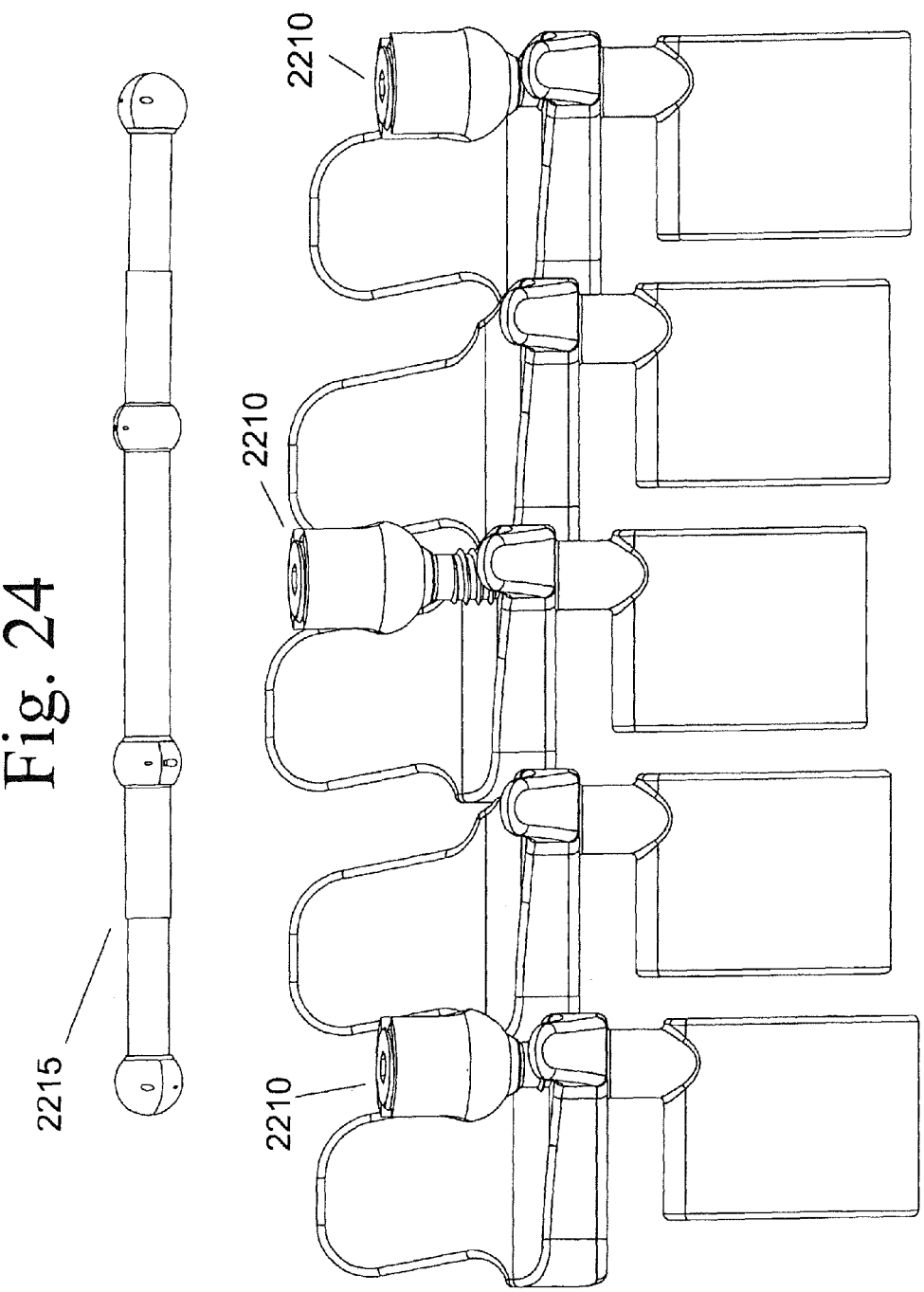

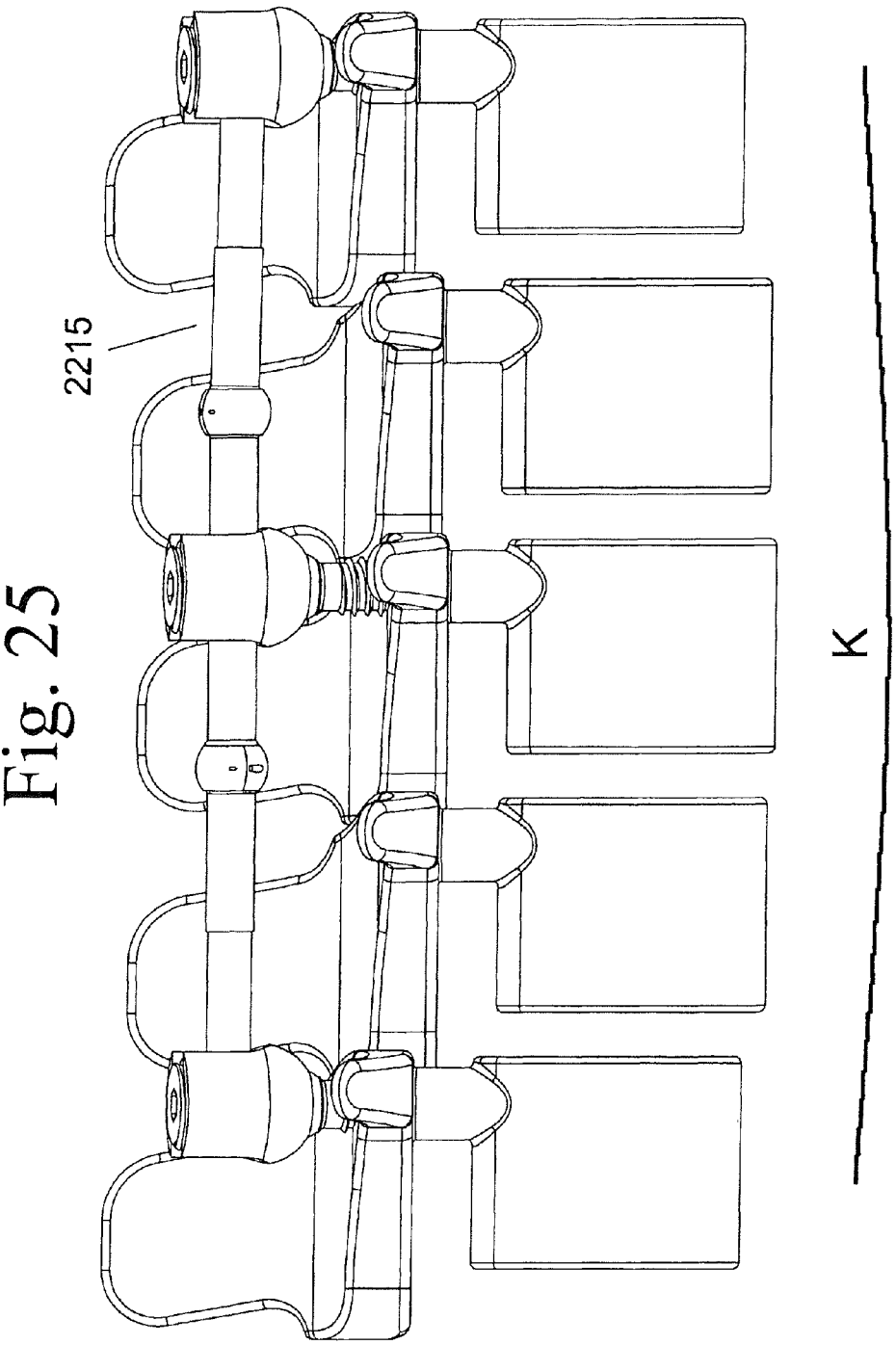

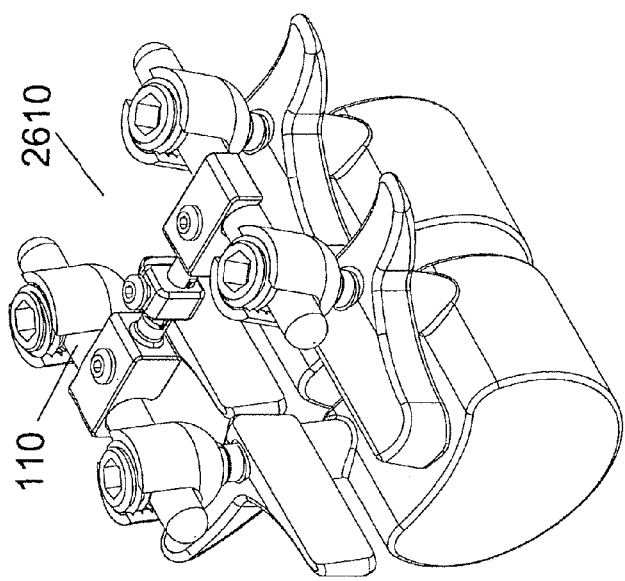
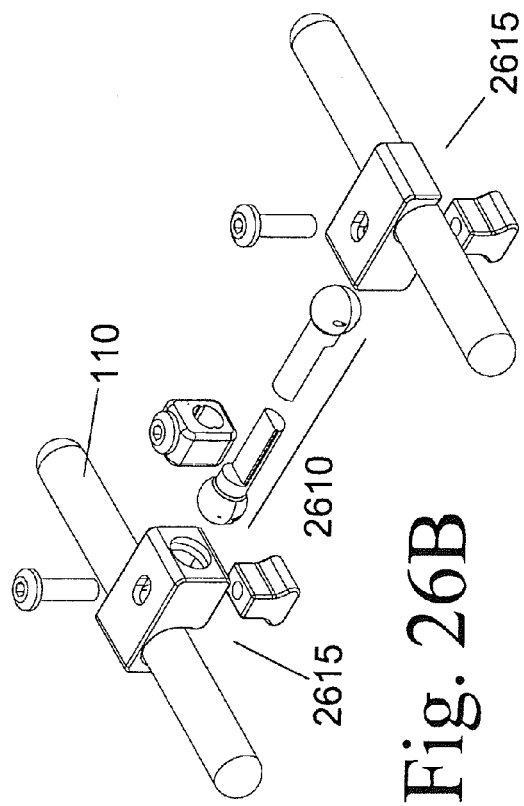
Fig. 26A
Fig. 26B

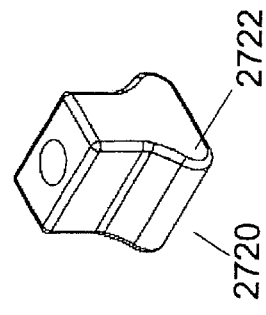
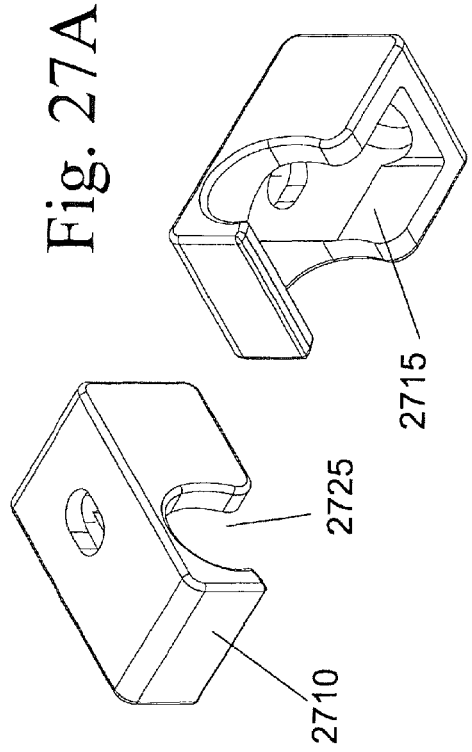
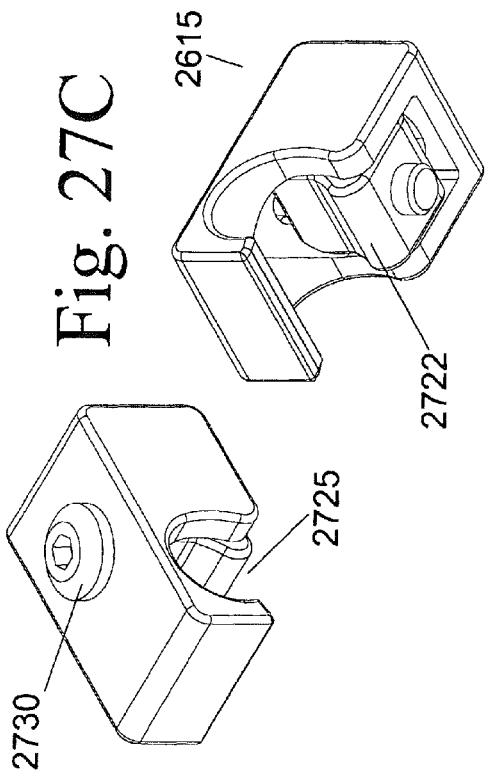

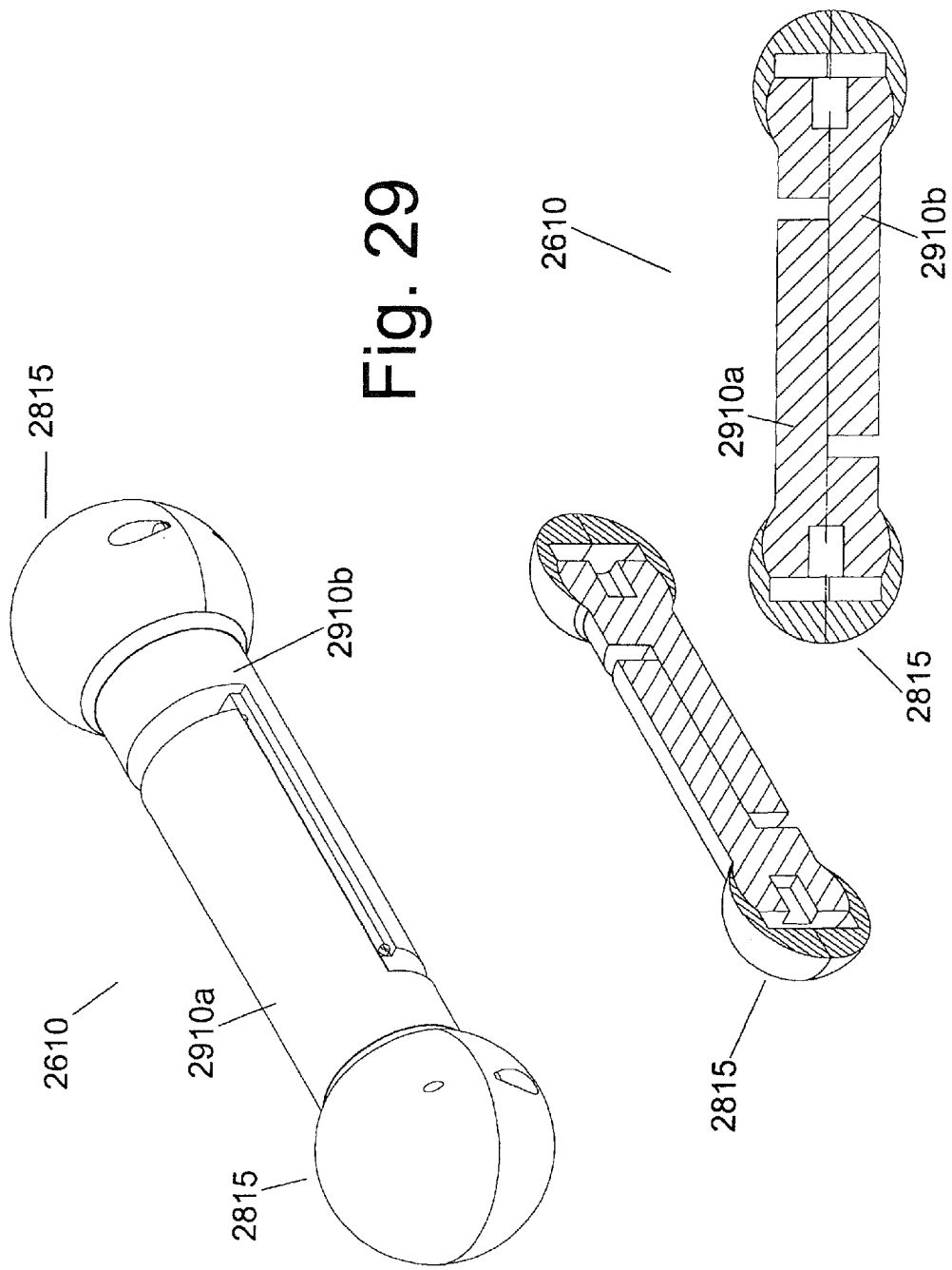

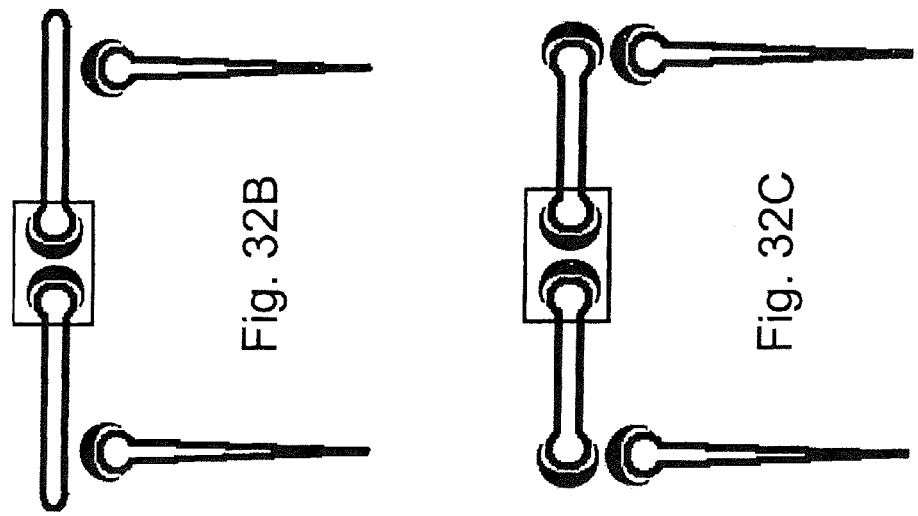
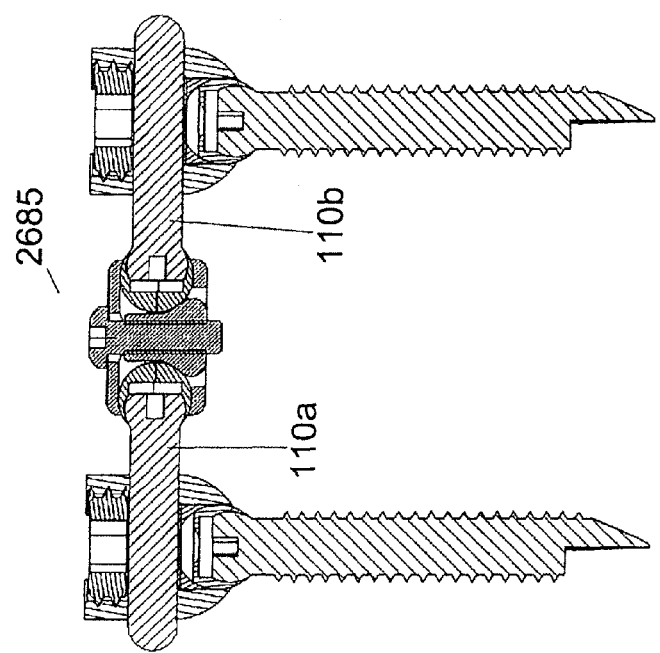

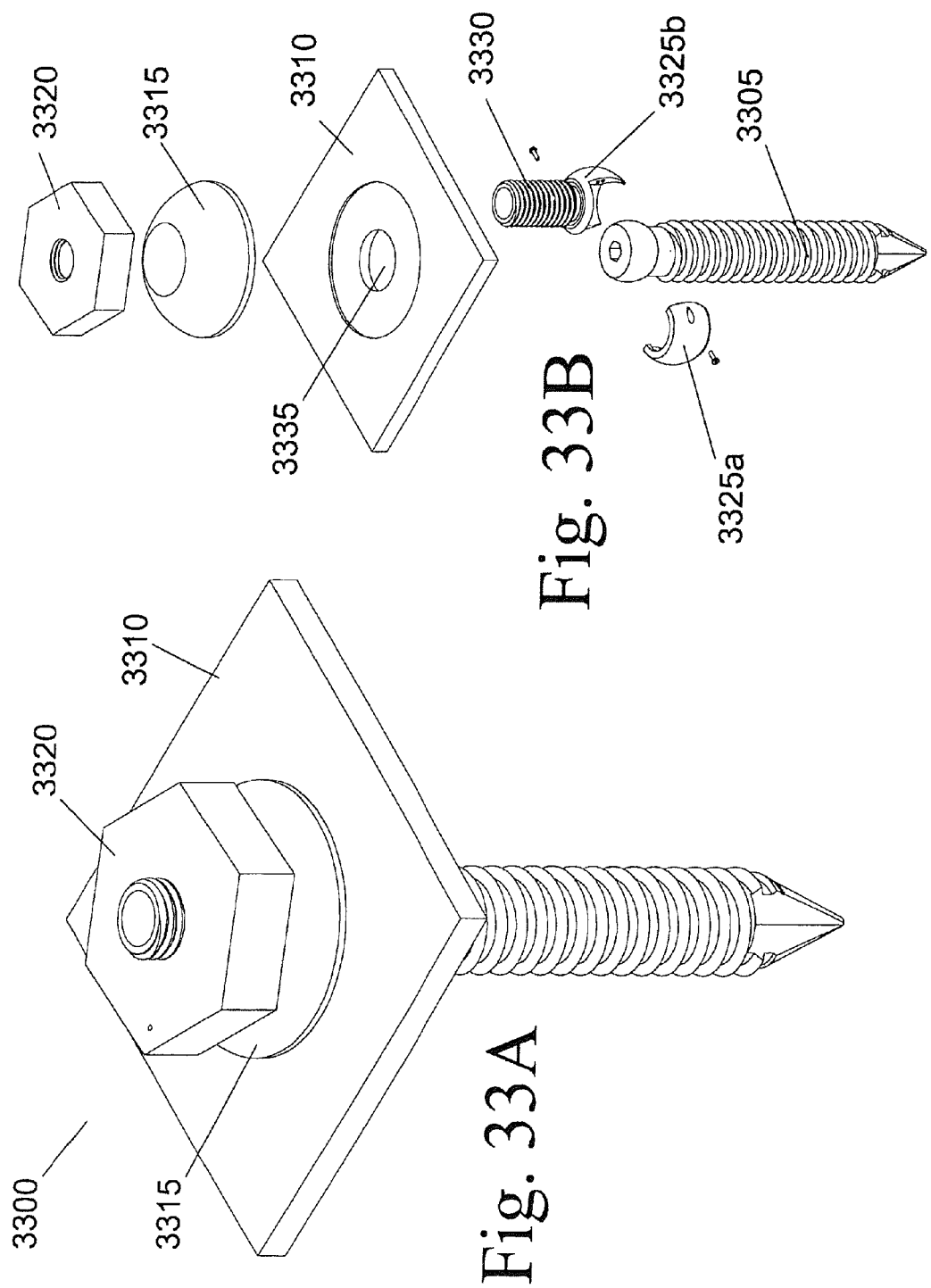

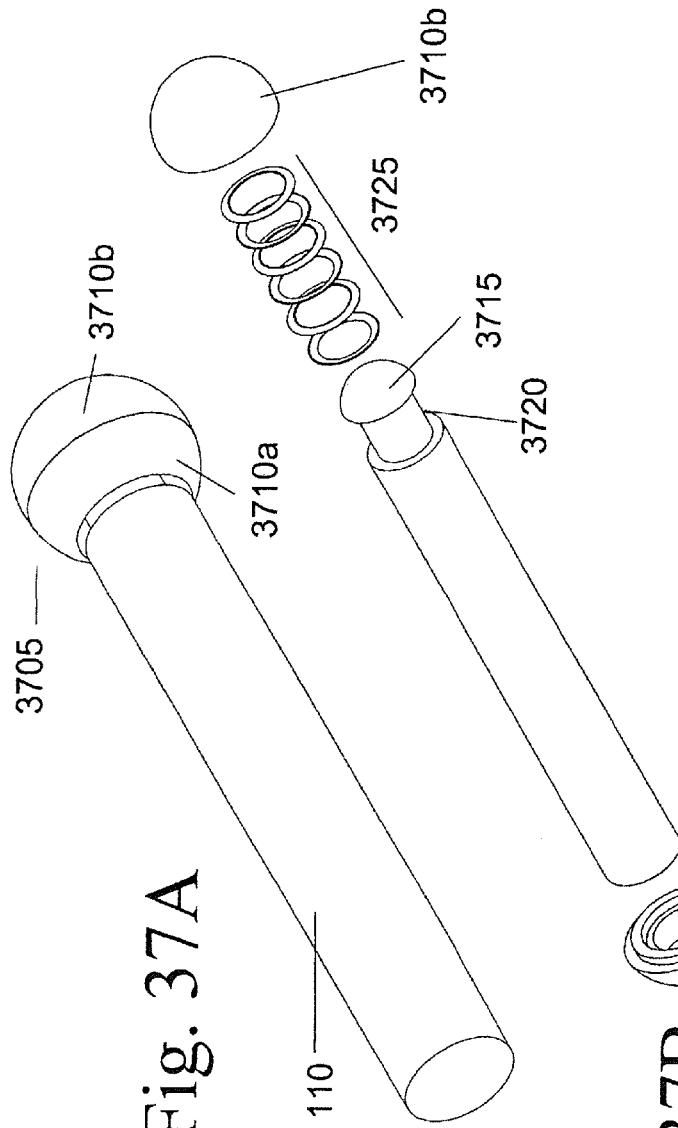
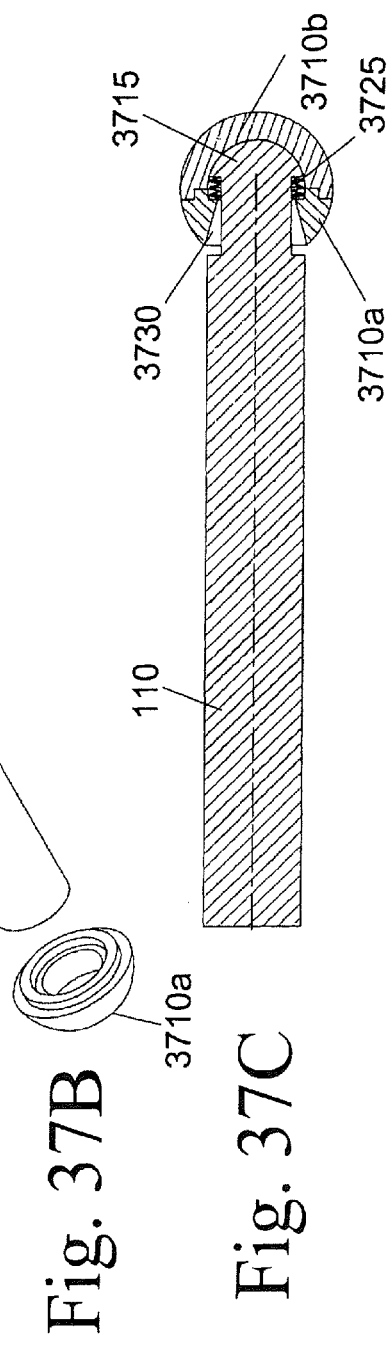
Fig. 37A
Fig. 37B
Fig. 37C

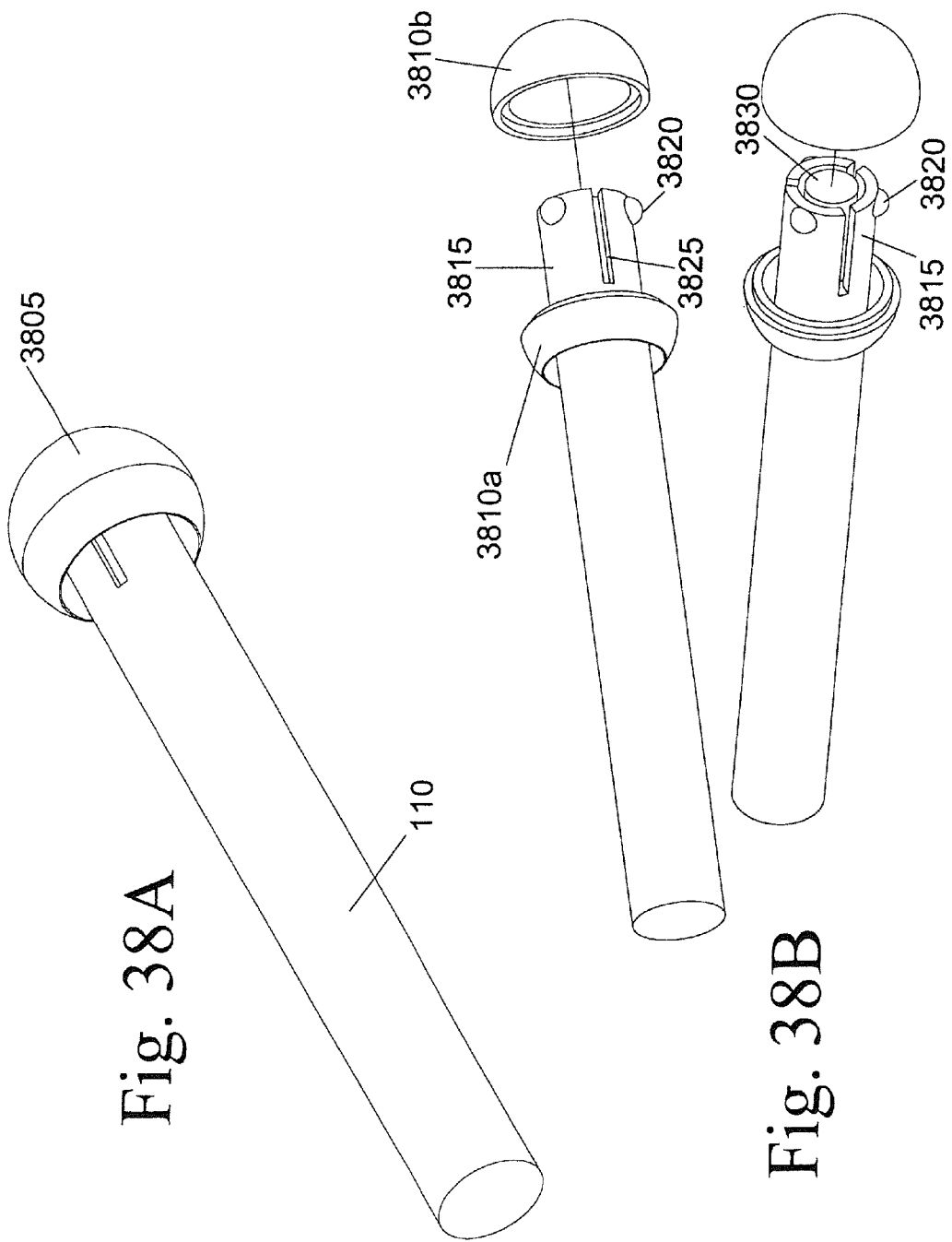

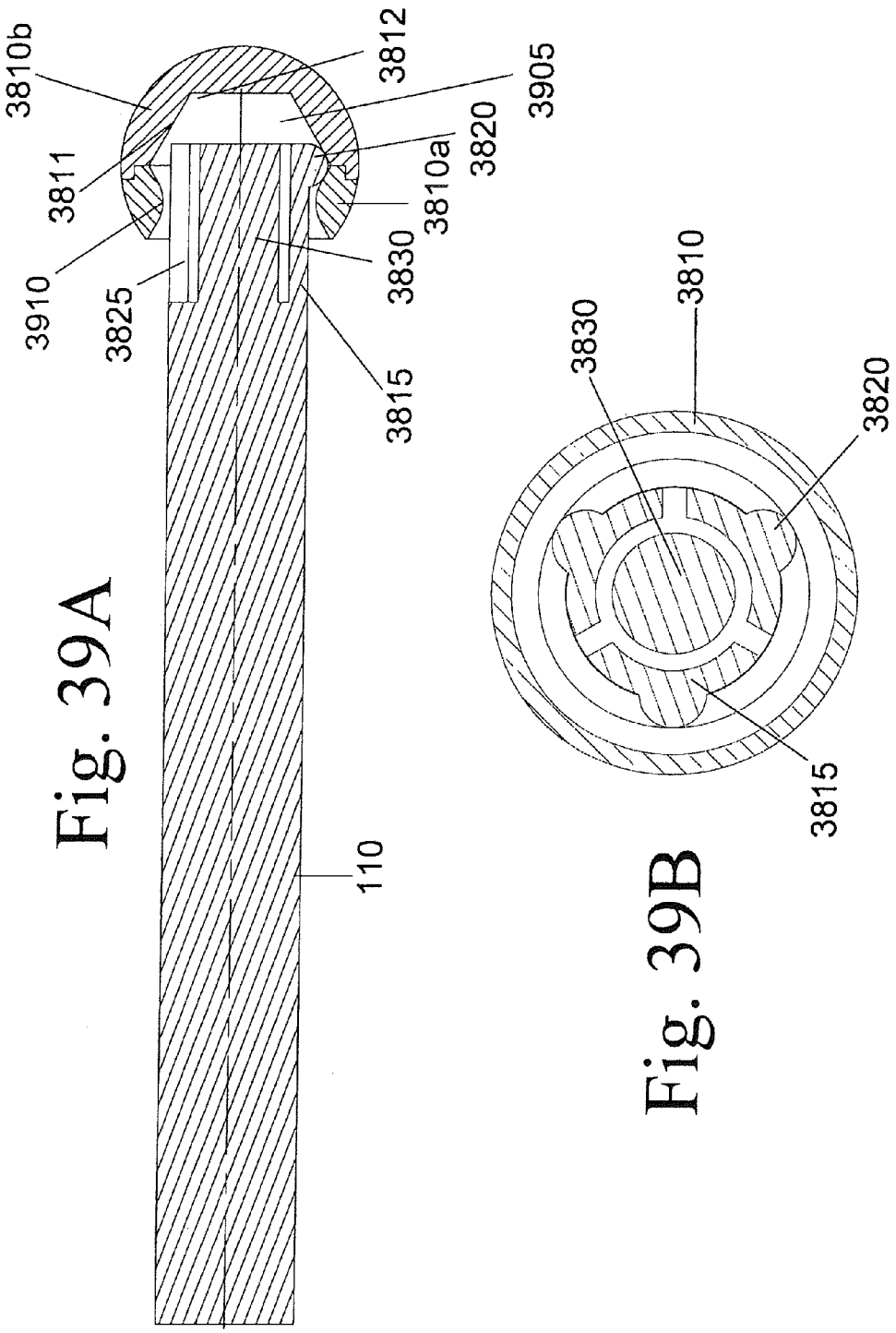

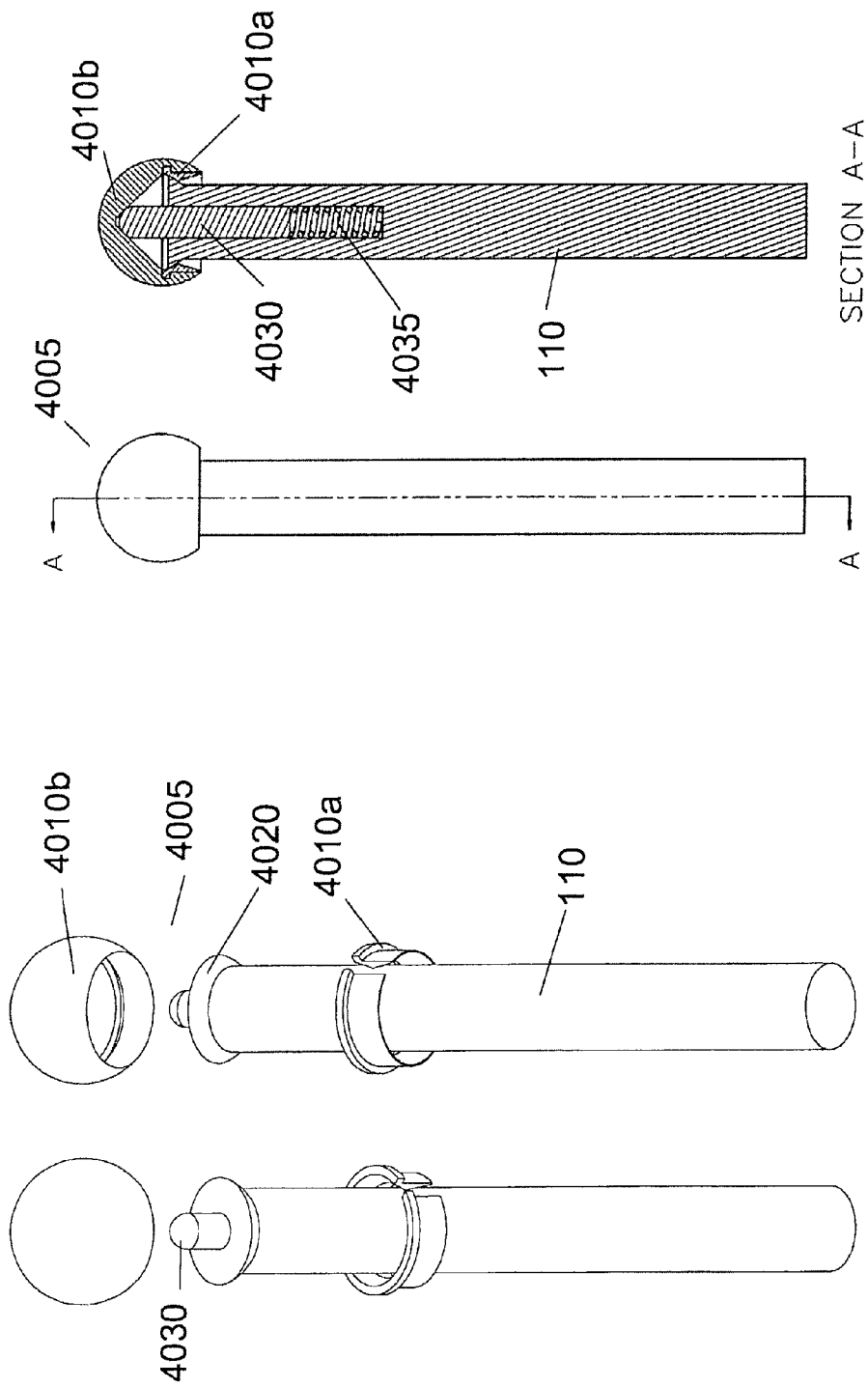

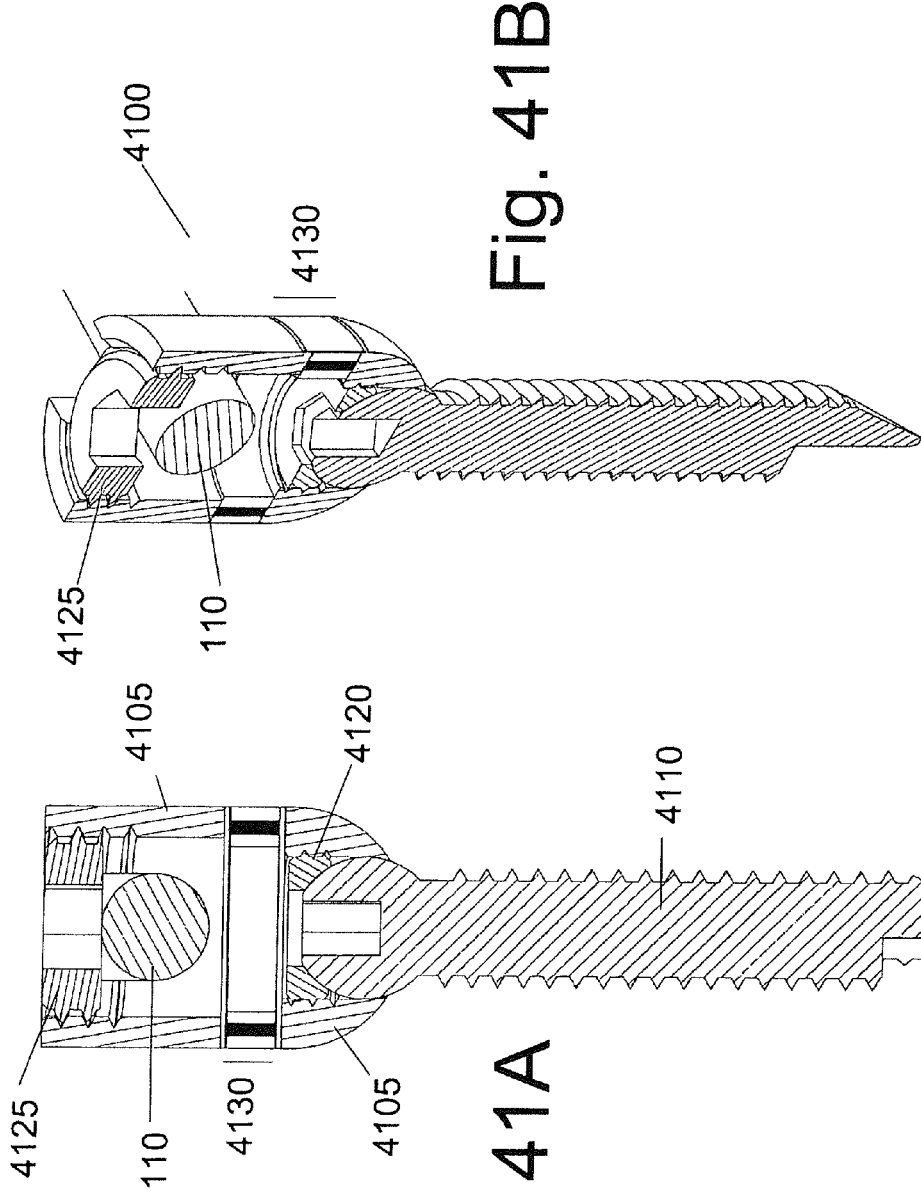

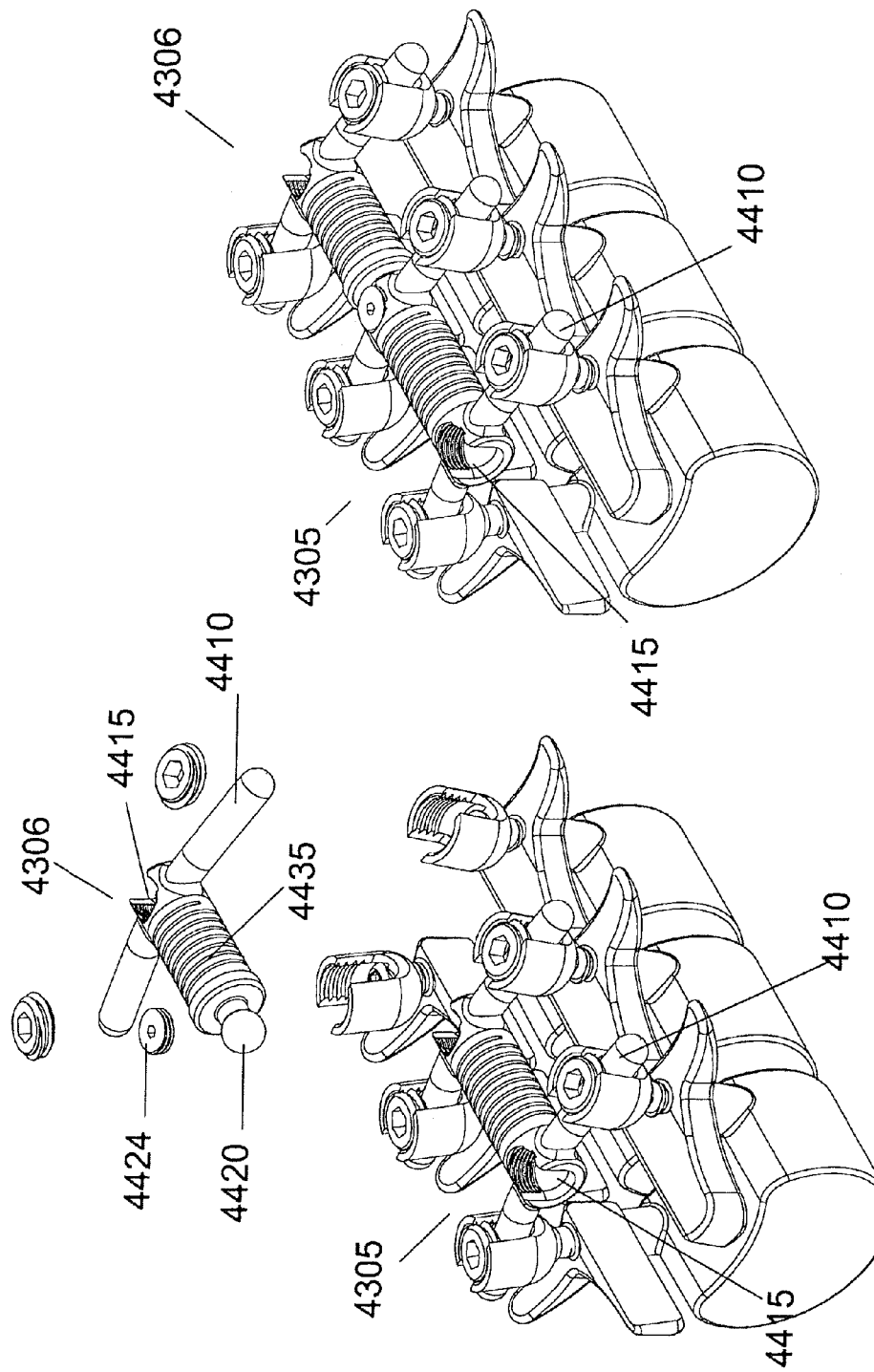

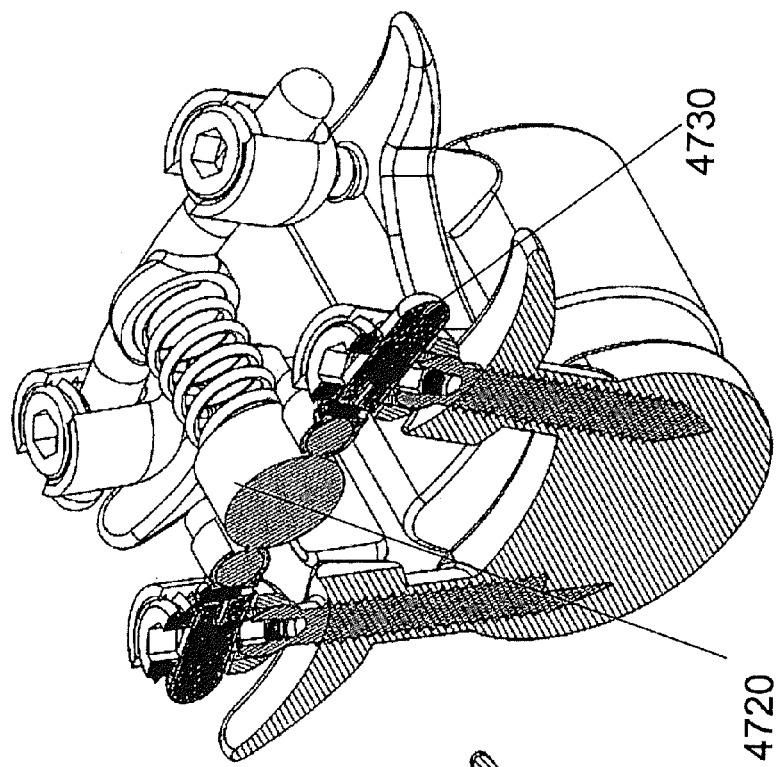
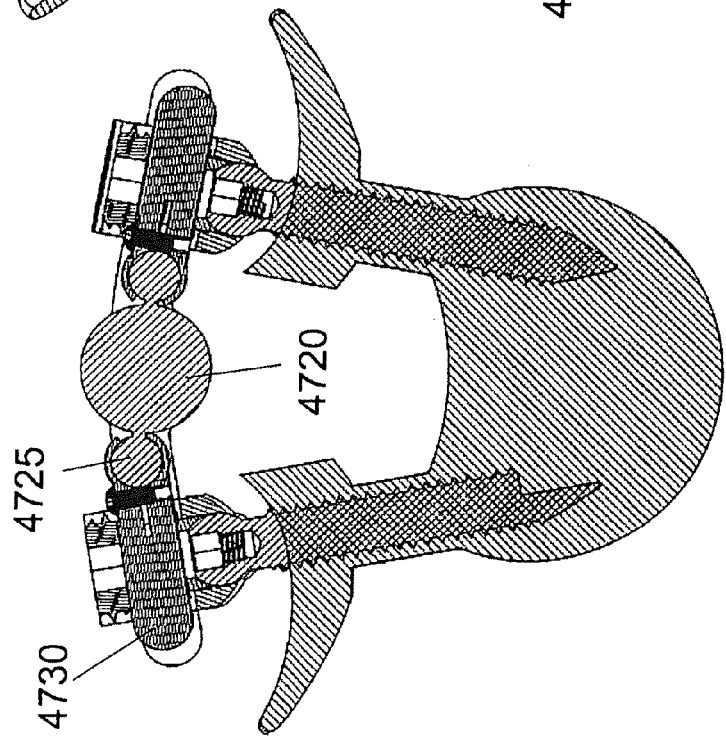
Fig. 47A
Fig. 47B

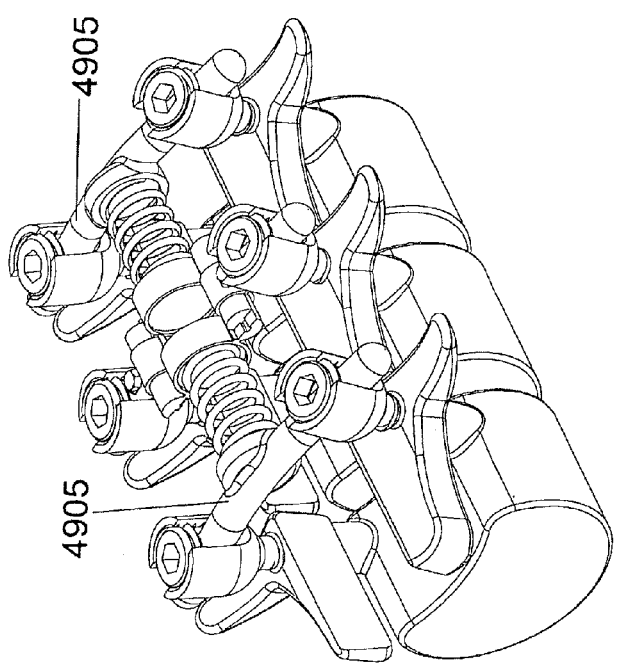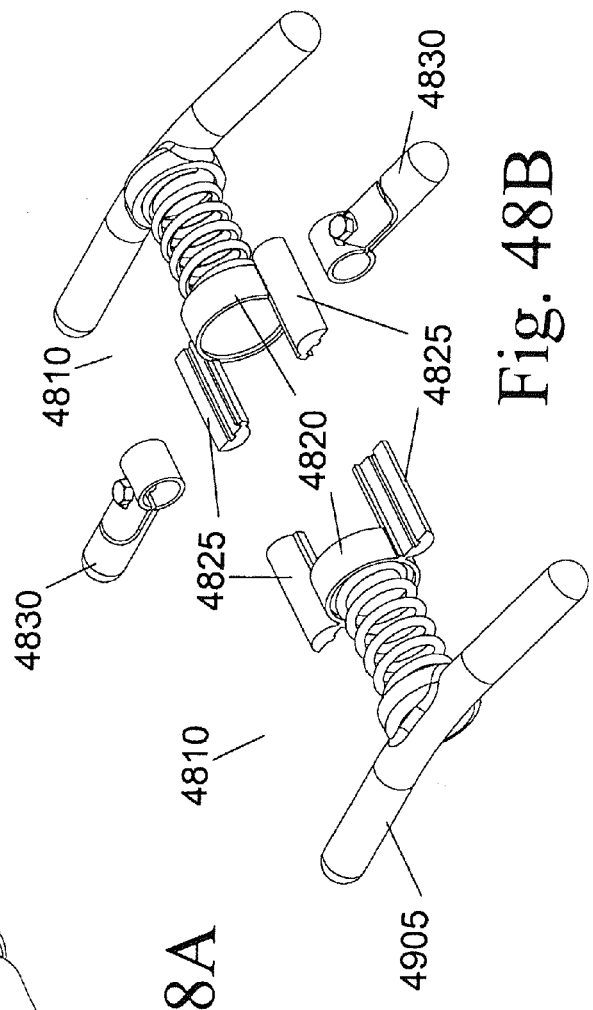

SPINAL MOTION PRESERVATION DEVICES AND METHODS OF USE

REFERENCE TO PRIORITY DOCUMENT

This application is a continuation of and claims priority to U.S. patent application Ser. No. 11/891,716 filed on Aug. 13, 2007 and entitled "Spinal Motion Preservation Devices and Methods of Use", which claims priority to U.S. Provisional Patent Application Ser. No. 60/837,023 filled filed Aug. 11, 2006, U.S. Provisional Patent Application Ser. No. 60/842,697 filed Sep. 6, 2006, U.S. Provisional Patent Application Ser. No. 60/852,774 filed Oct. 19, 2006 and U.S. Provisional Patent Application Ser. No. 60/874,195 filled filed Dec. 11, 2006, each of the foregoing incorporated herein by reference in their entirety.

BACKGROUND

Pain from degenerative spine disease is a major health problem in the industrialized world and the surgical treatment of spinal pathology is an evolving discipline. The traditional surgical treatment of a degenerating and painful inter-vertebral disc has been the complete immobilization and bony fusion of the involved spinal segment. An extensive array of surgical techniques and implantable devices have been formulated to accomplish this goal.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The second procedure necessitates re-dissection through the prior operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional fusion surgery.

There is a growing recognition that segmental spinal fusion and complete immobilization is an inadequate solution to degenerative disease of the spine. Replacement of the degenerated and painful disc with a mobile prosthesis is a more intuitive and rational treatment option. This approach would permit preservation of spinal mobility in many patients with degenerative disc disease. Eventually, the degenerative process will progress sufficiently so that motion preservation with a mobile prosthesis is no longer possible. Those patients may be treated with fusion. That is, fusion and complete segmental immobilization is reserved for those patients with advanced degenerative disease where the spinal segment is beyond surgical reconstruction.

Since the articulation between adjacent vertebral bones is composed of the inter-Vertebral disc and two facet joints, any attempt at restoration of vertebral motion must address all three components of the articulation. Replacement of the painful disc with an artificial prosthesis will restore a more full range of motion to the segment and those patients with extensive degenerative disease of the facet joints will experience an increase in facet joint pain after artificial disc implantation because of the increased motion. For this reason, artificial disc placement is contraindicated in those patients with significant facet joint disease. Similarly, those with healthy facet joints at the time of implantation will develop pain as these joints degenerate over time.

The rate of facet joint degeneration and the subsequent development of pain are emerging as major determinates of the clinical success of artificial disc replacement. That is, patient who undergoes artificial disc replacement to treat back pain will have re-emergence of the pain symptoms as the facet joints degenerate and the rate of joint degeneration will determine the time till symptom recurrence. Since the useful life of an artificial disc prosthesis greatly exceeds the life expectancy of the degenerating facet joint, the rate of joint degeneration becomes the true determinate of the pain-free interval that resides between the time of disc prosthesis implantation and the time of pain recurrence.

The use of posterior dynamic implants will partially off-load the posterior elements, load-share with the facet joint and significantly slow the rate of joint degeneration. These devices can be used to protect the facet joints in patients with an implanted artificial disc prosthesis or to slow the degenerative cascade in patients with a natural disc (i.e., without an artificial disc implant). However, since placement of posterior dynamic implants requires a posterior surgical approach while placement of an artificial disc prosthesis necessitates an anterior or lateral surgical approach, patients who require treatment of all three joints of a spinal motion segment must be subjected to a multi-stage operation with multiple incisions.

SUMMARY

There remains a need in the art for implants and methods that can treat multi-joint degeneration within a spinal motion segment using a single surgical approach. In this application, multiple embodiments of orthopedic implants that replace the function of a natural disc are illustrated. In an embodiment, the implant can be placed across the disc space through a trans-pedicular corridor using a substantially posterior surgical approach. In another embodiment, an implant can be placed across the disc space at a different level through a substantially lateral or anterior approach.

Multiple embodiments of posterior dynamic spinal implants are disclosed. Among other functions, these devices may be used to off-load the posterior spinal elements (facet joints and the like), load-share with the anterior spinal elements (inter-vertebral disc and the like), protect the facet joints in patients with an implanted artificial disc prosthesis, and slow the degenerative cascade in patients with a natural disc.

In one aspect, there is disclosed an orthopedic implant adapted to provide and maintain motion between adjacent vertebral bodies of a human or animal subject, comprising: a member sized and shaped to be positioned within a pathway in a first sacral vertebra along a trajectory that has a starting point lateral to a posterior sacral foramen and medial to a sacro-iliac joint, wherein the trajectory transverses a portion of one sacral pedicle and portion of a first sacral vertebral body and enters the disc space immediately superior to the sacrum; wherein a first portion of the implant transverses the first sacral vertebra and is adapted to adhere to the vertebral bone, and wherein a second portion of the implant positions within the disc space immediately above the sacrum and wherein the second portion is adapted to provide movement between the sacrum and the vertebra immediately above the sacrum.

In another aspect, there is disclosed a method for the implantation of an orthopedic device that maintains motion between adjacent vertebrae, comprising: positioning the device within a pathway in a first sacral vertebra along a trajectory that has a starting point lateral to a posterior sacral foramen and medial to a sacro-iliac joint, wherein the trajectory transverses a portion of one sacral pedicle and portion of a first sacral vertebral body and enters the disc space immediately superior to the sacrum, wherein the implant has a portion imparts motion, the portion being contained within the disc space.

In another aspect, there is disclosed a method for the implanting an orthopedic device in a subject, comprising: implanting the orthopedic device through a lateral entry site to the spine; and positioning a distal aspect of the implant to contact a vertebra at a level other than a vertebral level from which the implant insertion was started, wherein the insertion site is initiated through the lateral entry site in the spine.

In another aspect, there is disclosed an anchor adapted for fixation onto a bone of a human or animal subject, comprising a threaded bone screw having a curvilinear side partial defect that is adapted to form an implantation corridor for a second orthopedic implant.

In another aspect, there is disclosed a device that is adapted to interconnect two anchors that are each implanted into a bone member of a human or animal subject comprising: a rod member that has a first bearing surface on one end, wherein the first bearing surface is contained within a second bearing surface, wherein the first and second bearing surfaces articulate with respect to one another in a manner that substantially permits rotational movement and limits translational movement; wherein the second bearing surface is adapted to be retained by a bone anchor, such that in a first unlocked state of the bone anchor, the second bearing surface is freely movable relative to the bone anchor, and such that in a second locked state of the bone anchor, the second bearing surface is rigidly retained within the bone anchor but the first bearing surface is movable relative to the second bearing surface.

In another aspect, there is disclosed an anchor adapted for fixation onto a bone of a human or animal subject, comprising: a screw member having a head and a shank; a coupler that couples the head to a plate; and a locking member, wherein in a first state, the locking member permits the screw head to rotate relative to the coupler by virtue of a domed interface between the locking member and the coupler such that the screw can be freely rotated relative to the plate, and wherein in a second state the locking member is tightened against the coupler to lock against the coupler and fixate the coupler relative to the plate, and wherein the locking member is in the second state, the screw head can rotate at least slightly but is biased toward a neutral position.

In another aspect, there is disclosed a method of linking a first dynamic bone screw connector to a second bone screw connector, comprising: removably attaching a modular connector of the first bone screw connector to a modular connector of the second bone screw connector, wherein the modular connectors are attached to one another in a manner that permits relative movement between the modular connectors.

The disclosed devices can collectively be used to treat multi-joint degeneration and replicate physiologic spinal movement. Other features and advantages should be apparent from the following description of various embodiments, which illustrate, by way of example, the principles of the disclosed devices and methods.

BRIEF DESCRIPTION OF THE FIGURES

FIG. 5A shows another embodiment wherein the implant is positioned in a different manner in the bone.

FIG. 5B shows another embodiment of an implant.

FIG. 5C shows another embodiment wherein the implant is positioned in a different manner in the bone.

FIG. 6 shows an exploded view of a dynamic bone screw assembly.

FIG. 8A shows an exploded view of a dynamic connecting rod assembly.

FIG. 8B shows a cross sectional view of the rod assembly of FIG. 8A.

FIG. 8C show an additional view of the rod assembly.

FIGS. 11A-11C show assembled, exploded, and cross-sectional views, respectively, of the implant.

FIGS. 12B and 12C show exploded and assembled views, respectively, of a screw head assembly.

FIGS. 13A to D show additional views of alternative implant placement pathways.

FIG. 14A shows a perspective, explosive view of a rod with dynamic connecting assemblies on both ends.

FIG. 14B shows assembled views of the rod of FIG. 14.

FIGS. 16A and 16B show a dynamic connecting assembly that employs an elongated plate member.

FIGS. 18A-18E show various embodiments of rod assemblies with movable or articulating regions.

FIGS. 19A and 19B show exploded and cross-sectional views, respectively, of another embodiment of a dynamic rod assembly.

FIG. 23 shows a side view of a portion of a spine with a plurality of vertebrae that are offset from one another.

FIG. 24 shows the spine portion after bone screw assemblies have been attached to vertebrae and prior to attachment of a dynamic rod assembly to the bone screw assemblies.

FIG. 25 shows the spine portion after the dynamic rod assembly has been used to link the bone screw assemblies.

FIG. 26A shows an assembled view of a cross-connector connecting a pair of elongated fixation rods 110 on either side of the vertebral midline.

FIG. 26B shows an exploded view of the cross-connector.

FIG. 27A shows perspective views of a bracket member of a coupler assembly.

FIG. 27B shows a locking block of the coupler assembly.

FIG. 27C shows perspective assembled views of the coupler assembly

FIG. 29 shows perspective and cross-sectional views of the rod assembly of the cross-connector.

FIG. 32A shows the cross-connector without the vertebrae.

FIG. 32B shows a schematic view of the cross-connector linked to screw assemblies.

FIG. 32C shows a schematic view of a different cross-connector assembly that is linked to screw assemblies.

FIG. 33A shows a perspective view of a bone screw assembly.

FIG. 33B shows a perspective view of the assembly in an exploded state.

FIG. 37A shows a perspective view of a rod with a dynamic head assembly.

FIG. 37B shows the rod with the dynamic head assembly in an exploded state.

FIG. 37C shows a cross-sectional view of the rod.

FIG. 38A shows a perspective view of a rod with a dynamic head assembly.

FIG. 38B shows the rod with the dynamic head assembly in an exploded state.

FIG. 39A shows a side cross-sectional view of the rod.

FIG. 39B shows a cross-sectional view of the rod looking along the axis of the rod.

FIG. 40A shows a perspective view of a rod with a dynamic head assembly in an exploded state.

FIG. 40B shows the rod with the dynamic head assembly in an assembled state.

FIGS. 41A and 41B show cross-sectional views of a dynamic bone screw assembly.

FIGS. 43A and 43B show views of a modular dynamic connectors embodiment.

FIGS. 47A and 47B show cross-sectional views of the device of FIG. 46A.

FIG. 48A shows another embodiment of a multilevel dynamic connector.

FIG. 48B shows an exploded view of the multilevel dynamic connector of FIG. 48A.

DETAILED DESCRIPTION

Figure 1:
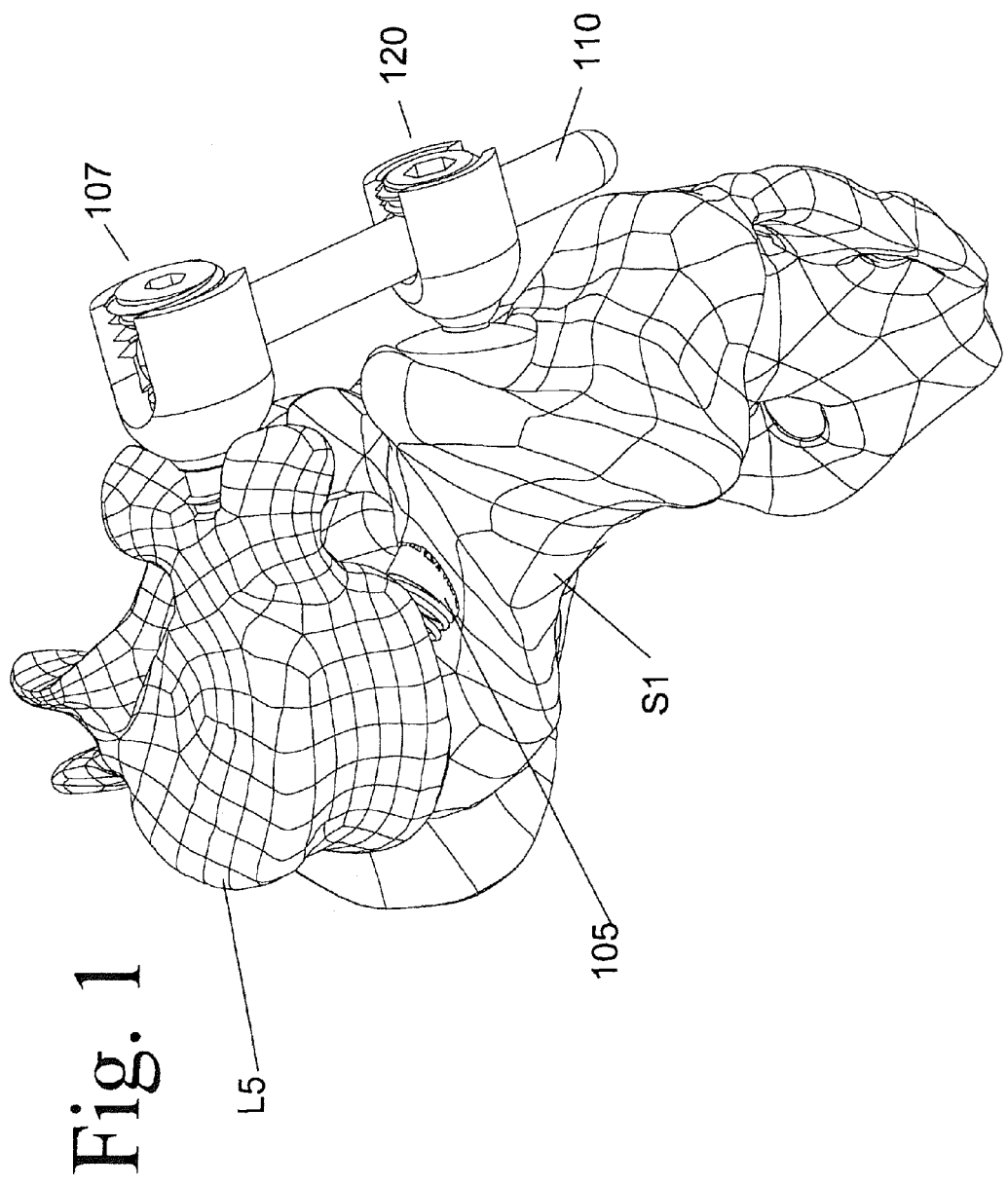
FIG. 1 shows a perspective view of a first embodiment of a device of the present invention positioned in spinal bone.

FIG. 1 shows a perspective view of a first embodiment of a device of the present invention positioned in spinal bone. In the illustration, a bone screw portion 205 (shown in FIG. 2A) of a bone screw assembly 107 has been placed through a left L5 pedicle and into a L5 vertebral body. A curvilinear implant 105 with a malleable segment is shown positioned within the L5/S1 disc space. An interconnecting rod 110 is used to connect the L5 fastener assembly 107 to an S1 fastener assembly 120.

Figure 2:
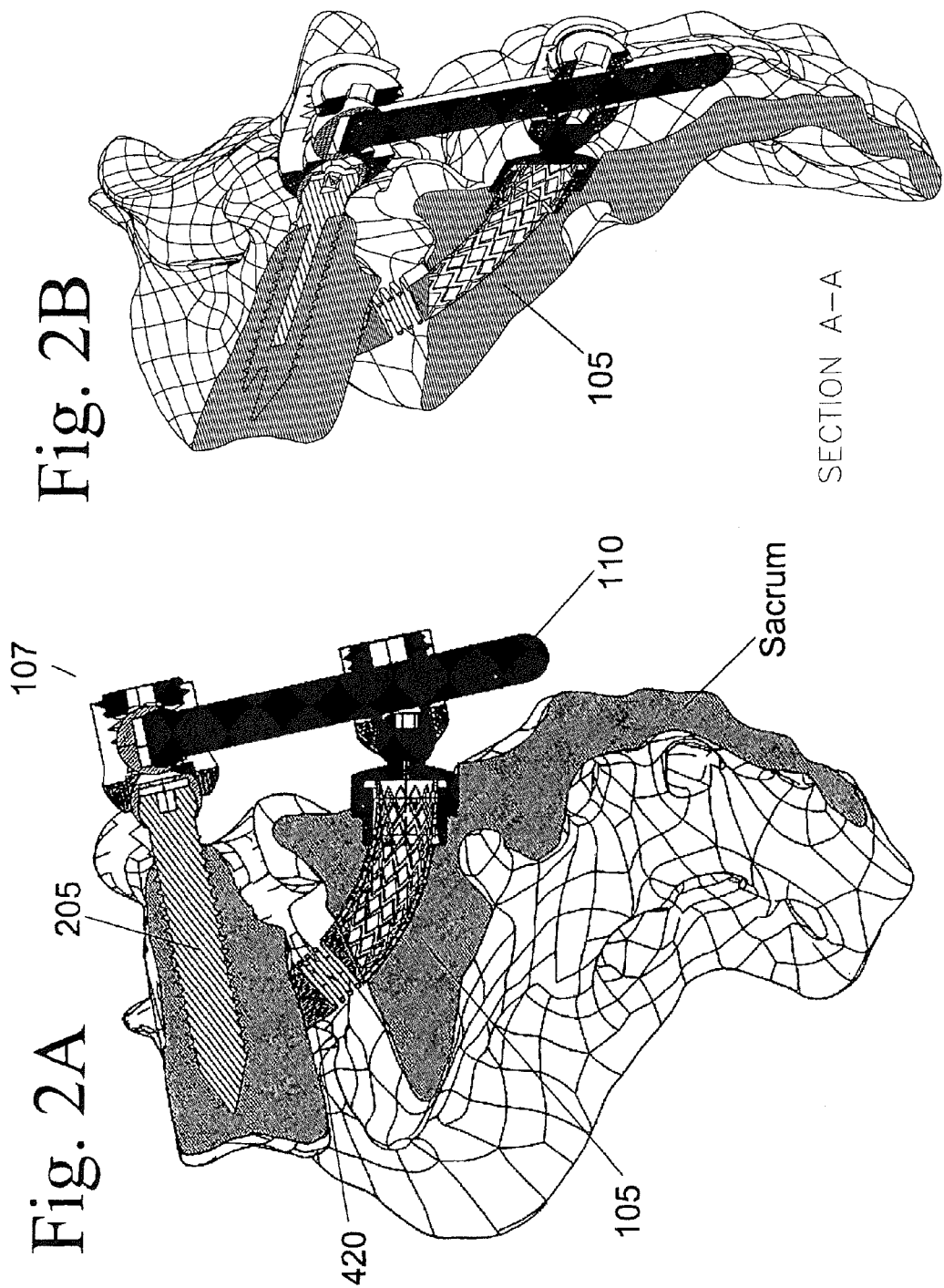
FIGS. 2A and 2B illustrate first and second perspective sectional views of the device of FIG. 1.
Figure 3:
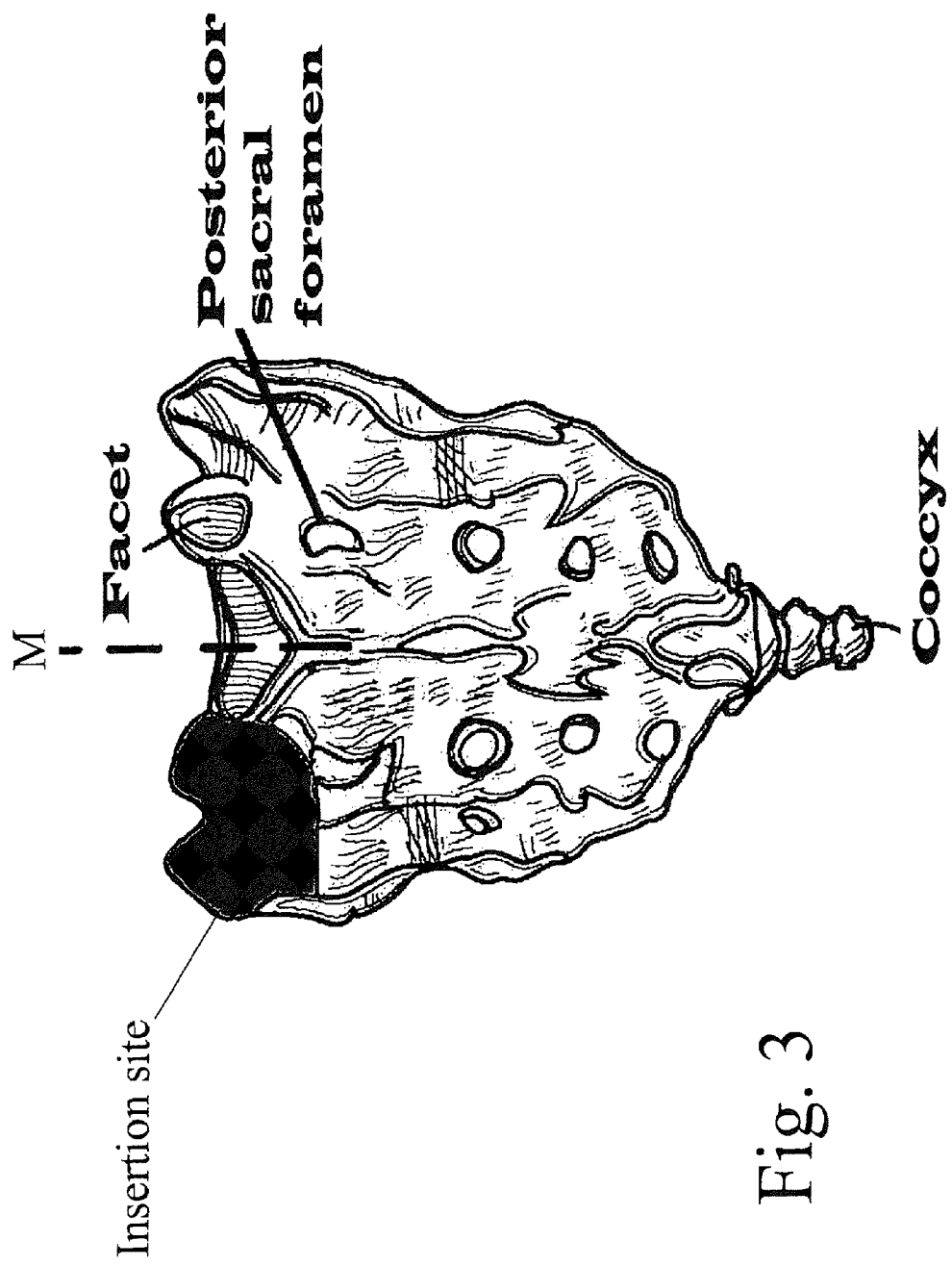
FIG. 3 shows the approximate insertion site.

FIGS. 2A and 26 illustrate first and second perspective sectional views of the device of FIG. 1. An implant insertion site is substantially located between the superior aspect of the posterior sacral surface and the superior aspect of the first posterior sacral foramen. The insertion site may overlap at least a portion of a L5/S1 facet joint. FIG. 3 shows the approximate insertion site. It should be appreciated that the actual insertion site may vary at least in part from what is shown in FIG. 3. In an embodiment, another pathway is formed through a similar insertion site on the opposite side of the vertebral midline and a second implant 105 is similarly positioned on each side of the midline M.

The implant 105 is inserted into a pre-formed pathway or is used to form a pathway through the aforementioned insertion site such that the pathway transverses a portion of a first sacral vertebrae and at least a portion of one sacral pedicle. In an embodiment, the pathway is curvilinear—as shown in FIGS. 2A and 2B—and may be of uniform or non-uniform curvature. Alternatively, the pathway may be linear or substantially linear. A linear pathway is particularly useful when an anterior spondylolisthesis (anterior displacement of an upper vertebra relative to a lower vertebra) of an L5 vertebral body is present relative to the sacrum.

Figure 4B:
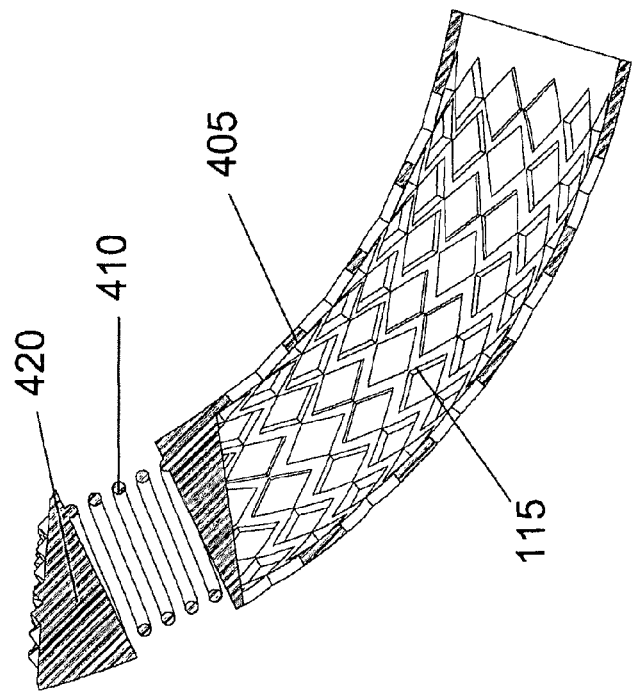
FIGS. 4A and 4B show perspective and side cross-sectional views, respectively, of a first embodiment of an implant.
Figure 4A:
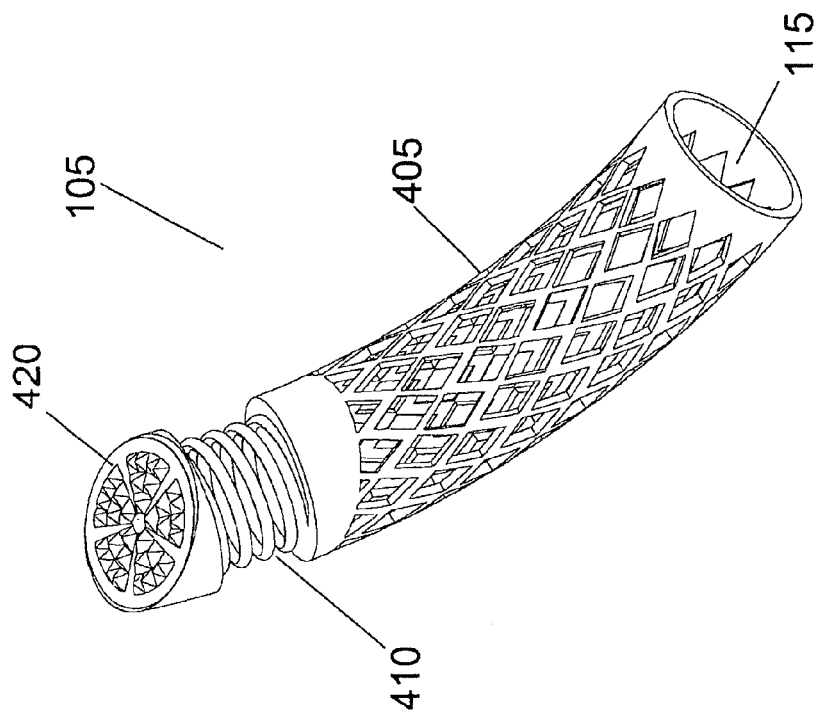

The implant 105 can have a variety of structures. FIGS. 4A and 4B show perspective and side, cross-sectional views, respectively, of a first embodiment of the implant 105. In the embodiment shown in FIG. 4, the implant 105 is a curvilinear, cage-like structure that is shaped to transverse the aforementioned sacral entry point, a sacral pedicle, a sacral vertebral body and then enter the disc space at the L5/S1 level. At least a portion of the implant 105 can be a hollow cage with an inner passageway or space 115 that accommodates a bone graft.

The implant 105 has side walls 405 that can be perforated so as to permit contact and interaction between the contained bone graft and the vertebral bone. Alternatively, the implant body may be substantially solid and may have various structural and/or surface features that serve to enhance anchorage into adjacent bone (not shown). Such features may be added to any implant embodiment described herein and may include, for example, one or more ridges, indentations, textures, or other structural features within and/or on the implant surfaces that would anchor the implant into the vertebral bone. An implant may be also made with a porous ingrowth surface (such as titanium wire mesh, plasma-sprayed titanium, tantalum, porous CoCr, and the like), provided with a bioactive coating, and/or made using tantalum in order to promote bone in-growth or establish a mineralized connection between the bone and the implant. Further, the implant may be at least in part manufactured from bone, bone graft substitutes, and/or carbon nanotubes.

As shown in FIGS. 4A and 4B, the implant 105 has a malleable member 410. The malleable member 410 is located on the implant such that the malleable member 410 can be at least partially positioned within the disc space when the implant is properly positioned in the bone as shown in FIGS. 2A-2C. In this manner, the malleable member 410 provides relative movement between the L5 vertebral body and the sacrum. In the illustrated embodiment, the malleable member 410 is shown as a helical spring. Alternatively, it may be composed of any material adaptable for malleable use. As known by those of ordinary skill in the art, there are a host of materials and mechanisms that may serve as malleable structures. These include, but are not limited to, elastomeric substances, super elastic materials, memory shape materials, machined spring devices, hydraulic mechanism, magnets and the like. Further, rigid members with an intervening joint (such as a ball in socket joint, and the like) may be also used to provide relative movement between the adjacent bones. A piston-like feature may be also placed within malleable member 410 to guide the allowable movement.

Figure 4C:
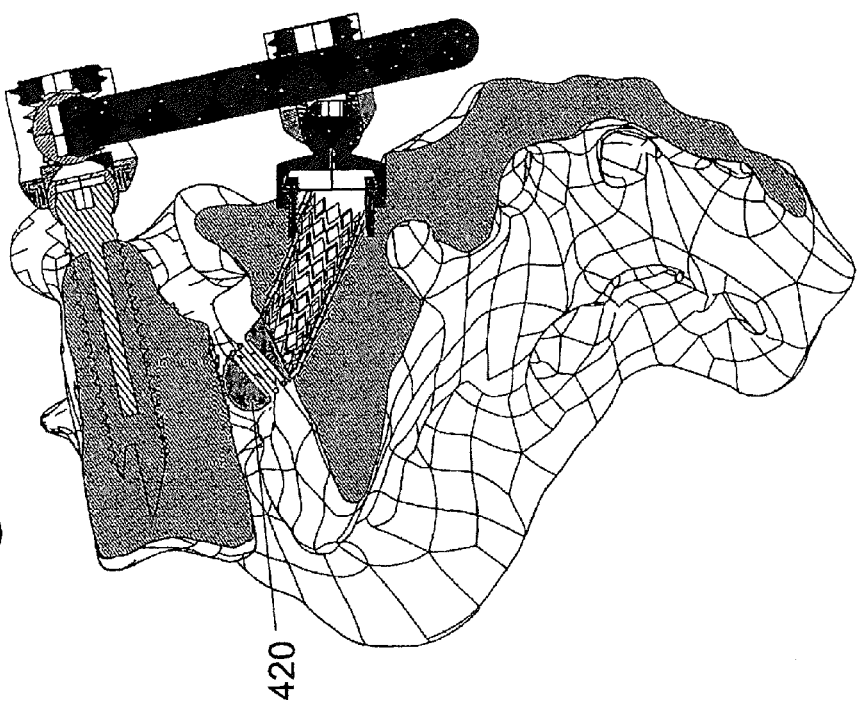
FIGS. 4C and 4D show other embodiments of a device.
Figure 4D:
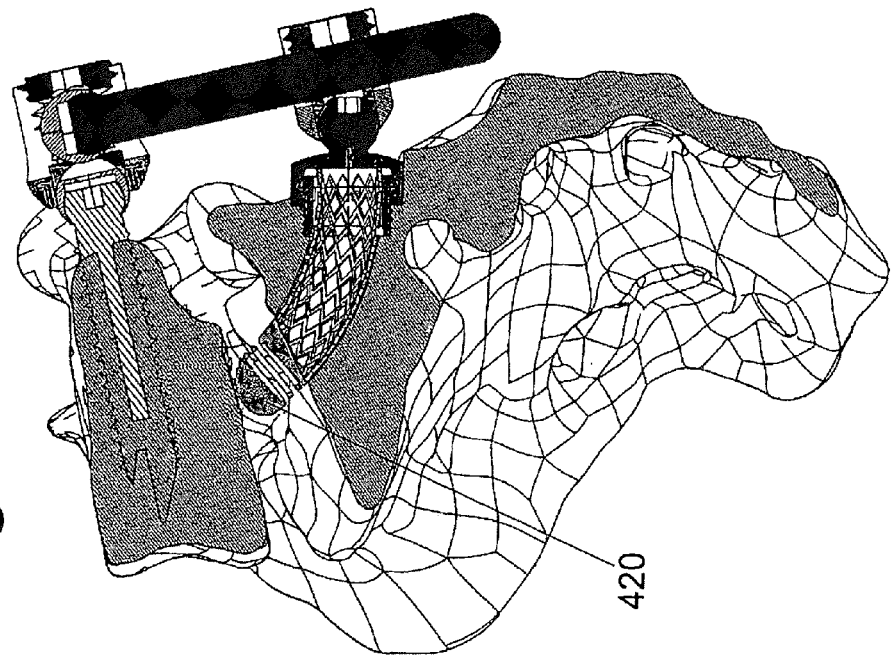

The implant 105 further includes an abutment member 420 that forms an abutment surface that abuts the inferior surface of the L5 vertebral body, as shown in FIGS. 2A and 2B. The abutment surface of the abutment member 420 may include features, such as protrusions, to increase gripping with bone. FIG. 4C shows another embodiment of the implant 105 wherein the abutment member 420 has a curved abutment surface that allows additional movement between the abutment member 420 and the L5 vertebral body.

FIG. 5A shows another embodiment wherein the implant 105 is positioned in a different manner in the bone. In this embodiment, the implant 105 penetrates the inferior L5 surface and enters the L5 vertebral body. The malleable member 410 is positioned in the disc space and a distal aspect of the implant 105 rests against the L5 bone screw 205. Alternately, the distal aspect of the implant 105 may rest at any other point within the L5 vertebral body. In another embodiment, implant 105 is used without supplemental posterior instrumentation—as shown in FIG. 5B. Further, any of the disclosed embodiments that replace the function of the natural disc, such as implants 105, may be used without supplemental posterior instrumentation.

FIG. 6 shows an exploded view of a dynamic bone screw assembly that can be used for the bone screw assembly 107 shown in FIG. 2A. In this embodiment, the head of a screw is positioned within an inner housing member in which the head can rotate in a ball and socket manner. The inner housing member can be immobilized relative to the housing to fixedly attach the screw to the housing. However, the head of the screw can rotate within the inner housing member to permit some movement between the screw and the housing. In addition, the head can be completely immobilized within the inner housing.

With reference to FIG. 6, the bone screw assembly includes an outer housing 601, a bone screw 600, and a rod 603. A locking nut 607 can be threaded into the housing 601 to provide a downward force onto the rod 603 and immobilize the rod relative to the housing 601 and an inner housing (610a & b). The bone screw 600 has a head 605 that can be positioned within inner housing members 610a and 610b. While not shown, the members 610a and 61b are joined to form the assembled inner housing member using threaded screws, ratchets, clips, adhesives, or any other technique for segment assembly. A saddle 615 is positioned within the housing 601 below the rod 603 and above the inner housing members 610 in the assembled device.

Figure 7:
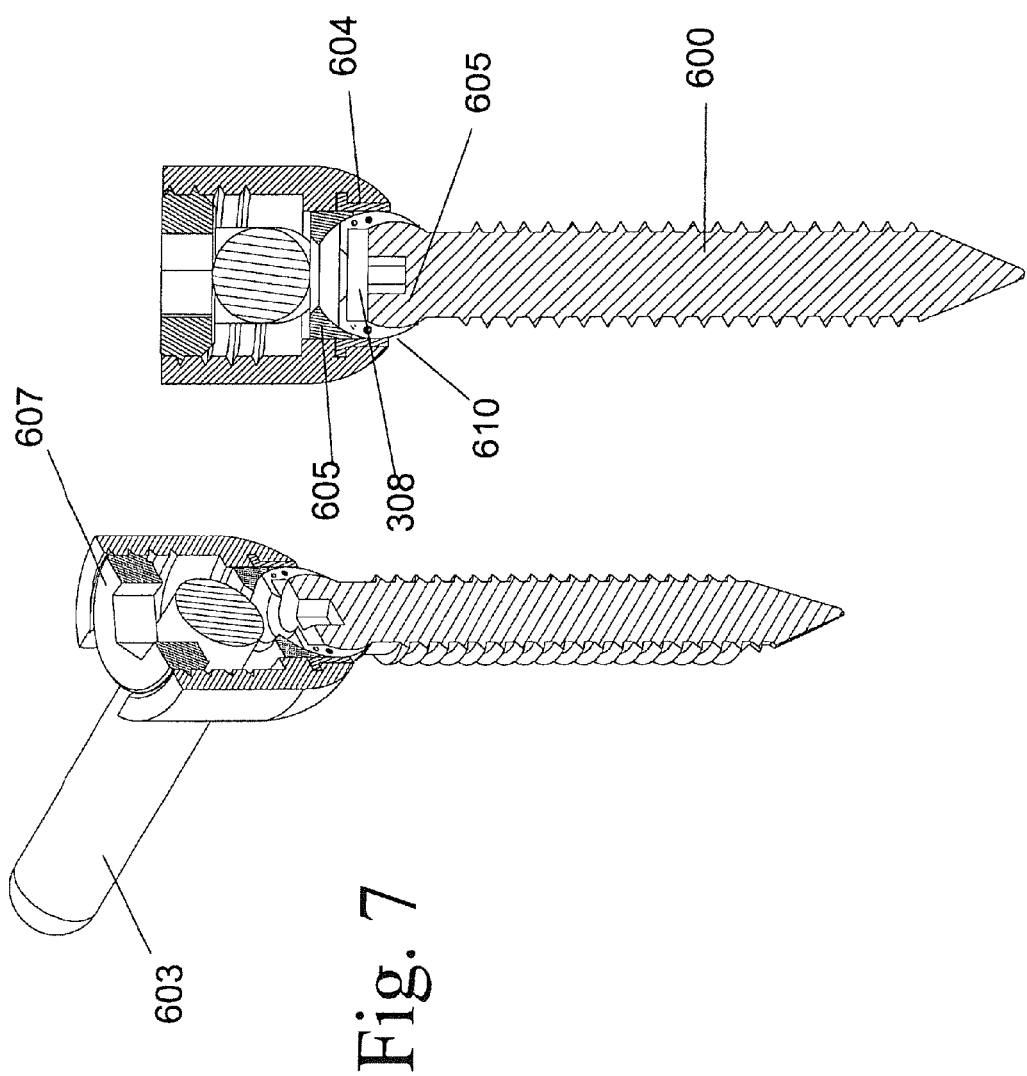
FIG. 7 shows perspective and side cross-sectional views of the assembly of FIG. 6.

FIG. 7 shows perspective and side cross-sectional views of the assembly of FIG. 6. The head 605 of the screw 610 is positioned within the inner housing members 610, which collectively form a socket for the head 605. The socket contains a space 308 that is positioned, for example, above the head 605. The saddle 615 is positioned directly above the inner housing 610 assembly and below the rod 603.

The locking nut 607 is advanced toward the rod 603 to tightly press the rod 603 against the upper edge of the saddle 615. This also causes the saddle 615 to press downward against the inner housing members 610 and force the inner housing members 610 against a seat in the housing 601, which causes rigid immobilization of the rod 603, housing 601, and inner housing members 610 relative to one another. However, the head 605 of the bone screw 600 is movable within the inner aspect of the inner housing members 610 to produce the dynamic aspect of the assembly. That is, the head 605 of the screw 600 can rotatably move within the socket formed within the inner housing members 610.

The space 308 within the inner housing member 610 can contain a material or structure that resists movement of the head 605 of the bone screw 600 relative to the inner aspect of the inner housing members 210. The material or structure within the space 308 can be, for example, elastomeric substances, super elastic materials, memory shape materials, machined spring devices, hydraulic mechanism, magnets or any other appropriate materials/devices that will resist movement of the head of bone screw relative to the inner aspect of the inner housing members. When the screw head is moved out of a predetermined position in the inner housing members, the material/device within space 308 will apply a force to the head of screw and resist any bone screw movement away from the neutral position. In this way, the assembly would return the screw and the attached bone to the neutral position once the deflecting force has dissipated. Further, before locking the assembly with the locking nut 615, the surgeon can freely adjust the orientation of the screw relative to housing without influencing the assembly's neutral position or pre-loading the screw and bone construct.

FIG. 8A shows an exploded view of a dynamic connecting rod assembly. FIG. 8B shows a cross sectional view of the rod assembly of FIG. 8A. The rod assembly can be used as the rod 110 shown in FIG. 2A. The assembly includes an elongated rod 805 having a dynamic head connector assembly including a head 810 that is rounded or partially-rounded with an end surface 807. The dynamic head connector assembly further includes outer members 815a and 815b. The dynamic head assembly permits relative movement between the rod 805 and a separate device (such as a bone screw or the implant 105) to which the dynamic head assembly is attached.

The rounded head can be a portion of an ellipse, a sphere and the like and contains an end surface 807. In one embodiment, the surface 807 is substantially flat while in another embodiment, the surface 807 is curvilinear. When the head 810 is a portion of a sphere, it is can be configured to be less than a one half of a sphere. The head 810 is positioned within outer members 815a and 815b. Members 815a and 815b are coupled using threaded screws, ratchets, clips, adhesives, or any other technique for segment assembly to form an assembled outer member 815.

With the head 810 positioned within the interior aspect of the assembled outer members 815, a cavity 820 is formed above the surface 807 of the head 810. The cavity 820 can contain an elastic material(s), fluids, spring device(s), magnets or any other appropriate materials/devices that will resist movement of the head 810 relative to the inner aspect of the assembled member 815. With relative motion between the members 815 and the head 810, the material(s)/device(s) within cavity 820 will apply a force to the surface 807 and resist any movement of the rod 805 away from a neutral position.

The inner surface of each half member 815a and 815b forms a complimentary surface to that of the outer surface of the head 810, wherein the interaction of these two surfaces forms a smooth articulation. In an embodiment, the inner surface is adapted to form a surface that is spherical, conical and the like. While the maximum diameter of the head 810 of the rod 805 is illustrated as being greater than the diameter of the rod 805, it should be appreciated that the head 810 may be alternatively adapted to have a maximum diameter less than or equal to the diameter of the rod 805. In such a configuration, a relief cut 825 is positioned between the head 810 and the rod 805 as shown in FIG. 8C.

Figure 9B:
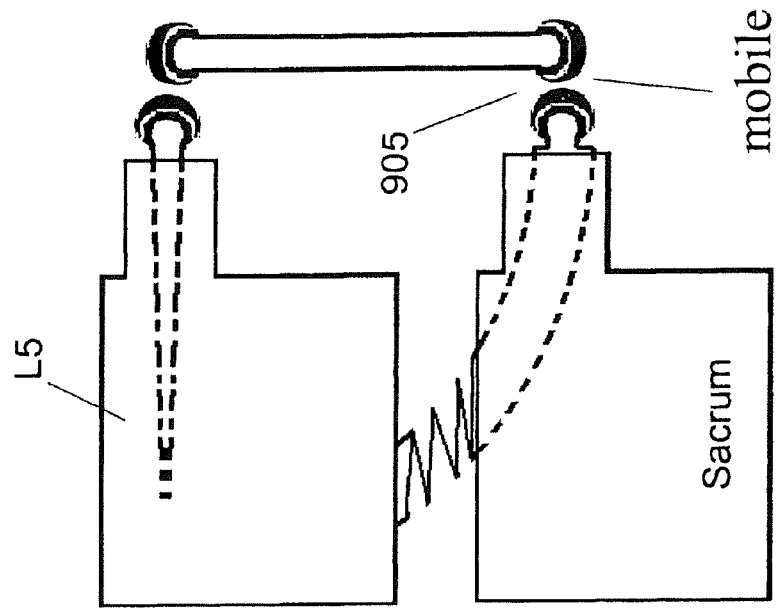
FIGS. 9A-9B show schematic representations of dynamic relationships between rod, bone screw, and implant assemblies.
Figure 9A:
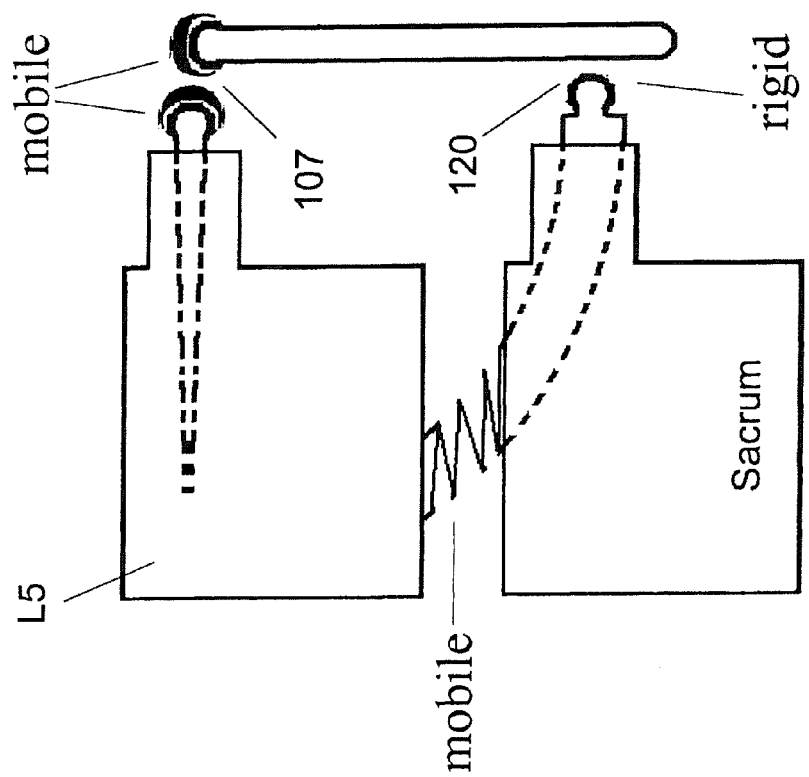

With reference again to FIGS. 2A and 2B, the interaction between bone screw assembly 107 and the rod assembly is dynamic in that relative movement is permitted therebetween. The relative movement is enabled via the dynamic screw assembly and the dynamic head connector assembly arrangements described above with reference to FIGS. 6 and 8A-8C. Thus, relative movement is allowed between rod 110 and bone screw 205 when the bone screw assembly 107 is in a locked configuration. Conversely, the rod 110 and the assembly 120 are rigidly affixed when assembly 120 is in the locked configuration. This relationship is schematically depicted in FIG. 9A and permits the formation of a rigid cantilever framework that is comprised of rod 110 and assembly 120 that is rigidly anchored into the sacrum S. The L5 vertebral body is movably attached to this rigid framework through the actions of malleable member 410 and the dynamic interaction between assembly 107 and the rod 110. This configuration is particularly useful when a spondylolisthesis (displacement of an upper vertebra relative to a lower vertebra in the horizontal plane) of an L5 vertebral body is present relative to the sacrum, since it permits relative movement between L5 and the sacrum but prevents vertebral translation.

In another embodiment, the interaction between the rod 110 and an assembly 905 that interfaces with the implant 105 may be dynamically adapted by the addition of at least one articulation member. This configuration is schematically depicted in FIG. 9B.

Figure 10:
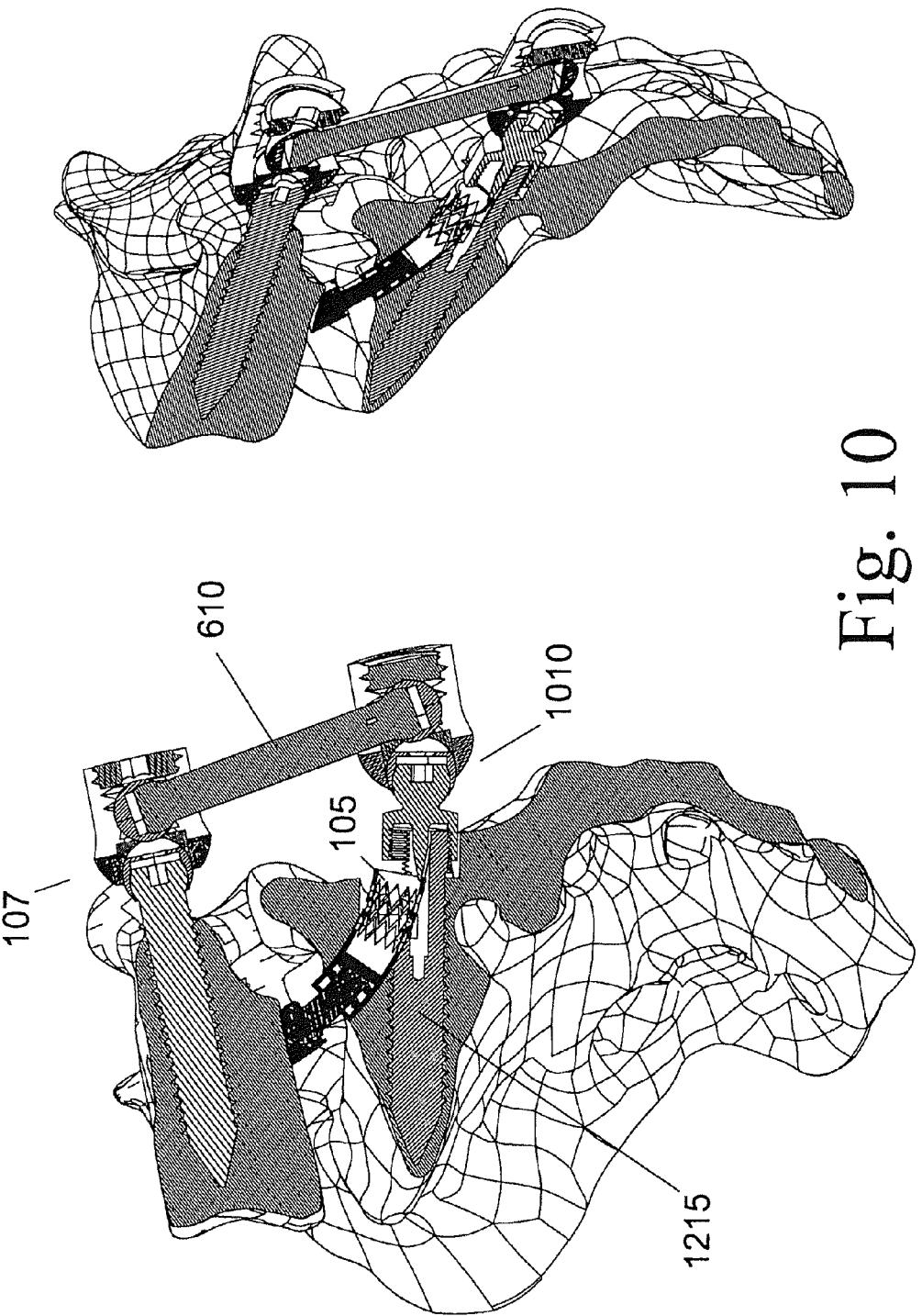
FIG. 10 shows a cross-sectional view of an embodiment of an assembly that permits dynamic movement between the rod and the implant.

FIG. 10 shows a cross-sectional view of an embodiment of an assembly that permits dynamic movement between the rod 110 and another embodiment of the implant 105. A dynamic bone screw assembly 1010 interacts with the implant 105 as described in detail below. FIGS. 11A-11C show assembled, exploded, and cross-sectional views, respectively, of the implant 105 of FIG. 10. The implant 105 comprises a curved member similar to the previously-described embodiment. A biasing member 1105, such as a spring, is positioned within the interior of the implant 105. A stop-member 1110 guides the biasing member 1105 within the implant 105. A curved extender 1115 with a rounded head 1120 is coupled to the biasing member 1105. The head 1120 is movably positioned within an abutment member 1130 that is adapted to abut a bony surface or any other desired surface. The abutment member 1130 can move (as represented by the arrow A in FIG. 11C) relative to the remainder of the implant 105 and tension or compress the biasing member 1105.

Figure 12A:
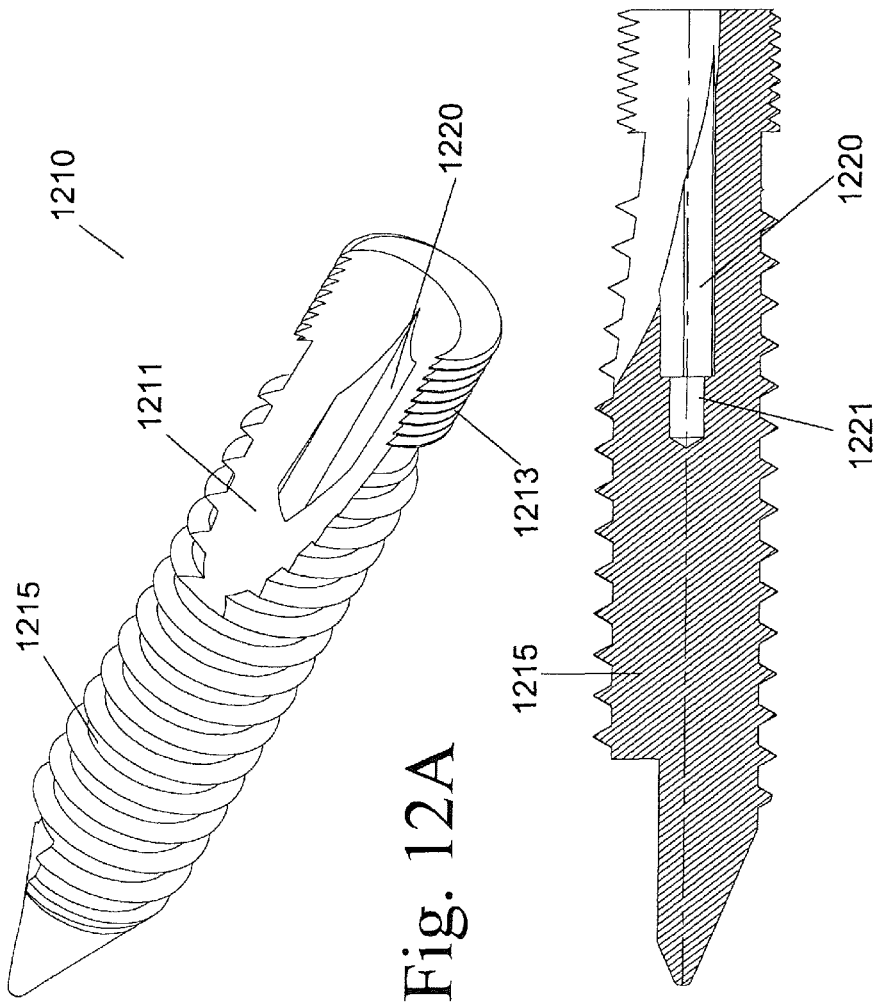
FIG. 12A shows perspective and cross-sectional views of a bone screw that interacts with the dynamic implant of FIGS. 11A-11C.

FIG. 12A shows perspective and cross-sectional views of a bone anchor 1210 that interacts with the dynamic implant of FIGS. 11A-11C. The anchor 1210 includes a distal threaded shank 1215 that screws into bone and a proximal threaded shoulder 1213. A curvilinear cut-out 1211 is formed along one side of the anchor 1210. Preferably, the cut-out 1211 has a radius and curvature comparable to complimentary implant 105 so that the implant may smoothly travel within cut-out 1211 during placement. A bore 1220 extends through the wall of cut-out 1211 along the central longitudinal axis of shank 1215. The internal shape of bore 1220 is adapted to accept the distal end of a complimentary screw driver. In the illustrated embodiment, bore 1220 has a hexagonal configuration but any of the known screw driver/receptacle configurations may be alternatively used. Threaded cylindrical bore 1221 (threads not shown) rests at the distal end of bore 1220 and acts a point of threaded attachment between the screw driver and anchor 1210.

FIGS. 12B and 12C show exploded and assembled views, respectively, of the head assembly 1230. With reference to FIG. 12B, the head assembly 1230 has a rounded head 1305 positioned on a housing 1310. The head 1305 fits within and interacts with a pair of housing members 1316a and 1316b in the same manner of the housing members 610 described above with reference to FIG. 6. Thus, relative movement is permitted between the head 1305 and the housing members 1316. A space 1325 (FIG. 12C) is formed when the head 1305 is positioned within the assembled members 1316 and the space preferably contains a malleable biasing material that biases the head 1305 toward a neutral position.

With reference to FIG. 12C, the housing 1310 has an interior threaded cavity 1340 that is sized and shaped to accept the proximal threaded shoulder 1213 of the bone anchor 1210 of FIG. 12. With reference again to FIG. 10, in the assembled device, the outer wall of the implant 105 abuts the surface of cut-out 1211 of anchor 1210. With member 1230 screwed onto the proximal aspect of anchor 1210, protrusion 1341 of member 1230 forcefully abuts the proximal aspect of implant 105 and traps it against the inner aspect of cut-out 1211. In this way, the implant is at least partially immobilized relative to anchor 1210.

Figure 15B:
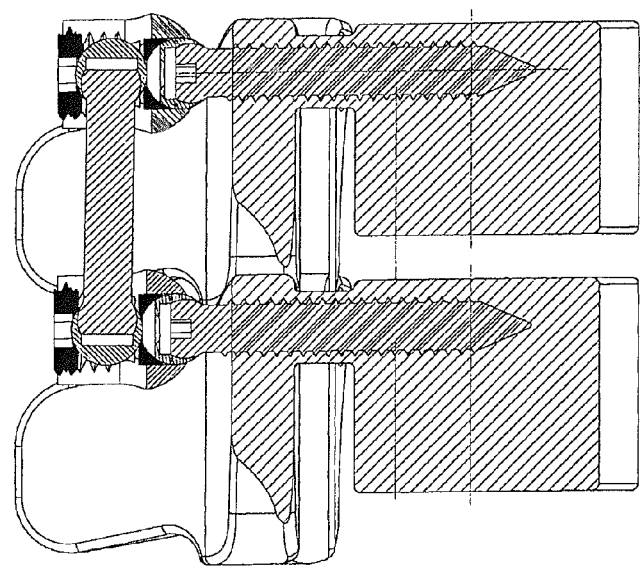
FIGS. 15A to F show various embodiments of implant positioning and motion.

Several pathways and methods that allow placement of the distal tip of an implant at a spinal level that differs from the implant insertion site are now described. FIG. 13A shows an anterior-posterior and lateral views of the spine with a curvilinear implant placed through a lateral insertion site. FIG. 13B shows a sectional view through the implant. While depicted as a hollow cage implant that may be filled with bone graft material and used to fuse adjacent bones, the pathway and method may be alternatively used to place a motion preserving curvilinear implant, such as implant 105. In another embodiment, FIG. 13C shows anterior-posterior and lateral views of the spine with a substantially straight implant placed through a lateral insertion site. FIG. 15E shows a sectional view through the implant. Alternatively, a straight motion preserving implant that employs a ball-and-socket joint atop a movable member or piston that is situated within a substantially straight cage (similar to curvilinear implant 105) may be used. Finally the pathway and implant may have a combined straight segment/curved segment configuration.

With further reference to FIG. 10, the rod 110 can be configured such that it has dynamic capabilities with respect to both the assembly 107 and the assembly 120. This embodiment of the rod 110 has a dynamic head assembly similar to that shown in FIGS. 8A-8C. However, the dynamic head assembly is on both ends of the rod, rather than on a single end as in the embodiment of FIGS. 8A-8C. FIG. 14A shows a perspective, explosive view of a rod 110 with dynamic connecting assemblies on both ends. As discussed above, the connecting assemblies includes the elongated rod 110 having heads 810 that are rounded or partially-rounded with an end surface 807. The rounded head can be a portion of an ellipse, a sphere and the like and contains an end surface 807. In one embodiment, the surface 807 is substantially flat while in another embodiment, the surface 807 is curvilinear. When the head 810 is a portion of a sphere, it is can be configured to be less than a one half of a sphere. The head 810 is positioned within outer members 815a and 815b. The members 815a and 815b are joined to form an assembled outer head member using members 1405 such as threaded screws, ratchets, clips, adhesives, or any other technique for segment assembly.

FIG. 14B shows assembled views of the rod of FIG. 14A. With the head 810 positioned within the interior aspect of the assembled outer members 815, a cavity 820 is formed above the surface 807 of the head 810. The cavity 820 can contain any material or device adaptable for malleable use. These include, but are not limited to, elastomeric substances, super elastic materials, memory shape materials, machined spring devices, hydraulic mechanism, magnets and/or any other appropriate materials/devices that will resist movement of the head 810 relative to the inner aspect of the assembled member 815. With relative motion between the members 815 and the head 810, the material(s)/device(s) within cavity 820 will apply a force to surface 807 and resist any movement of the rod 805 away from a neutral position.

Figure 15A:
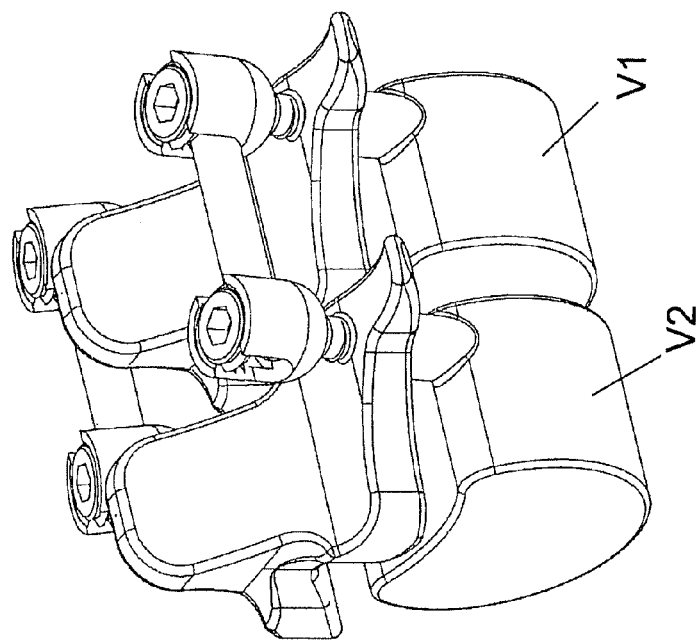
Figure 15D:
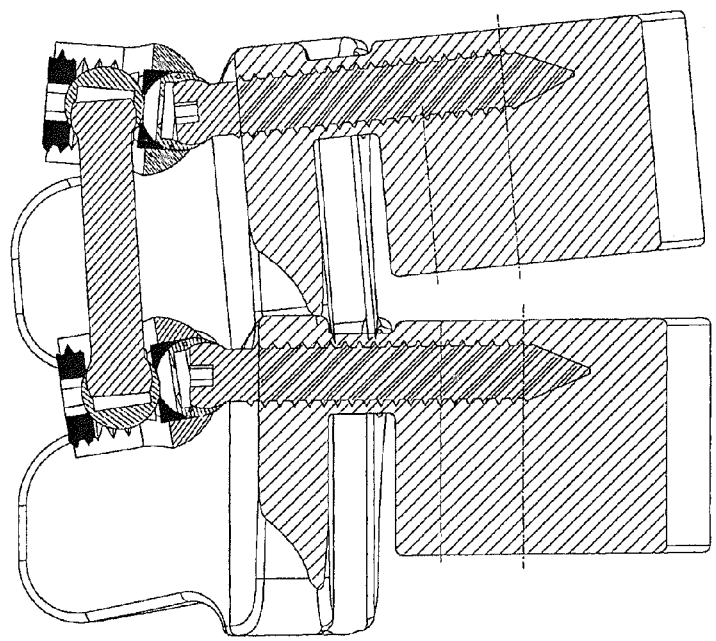
Figure 15C:
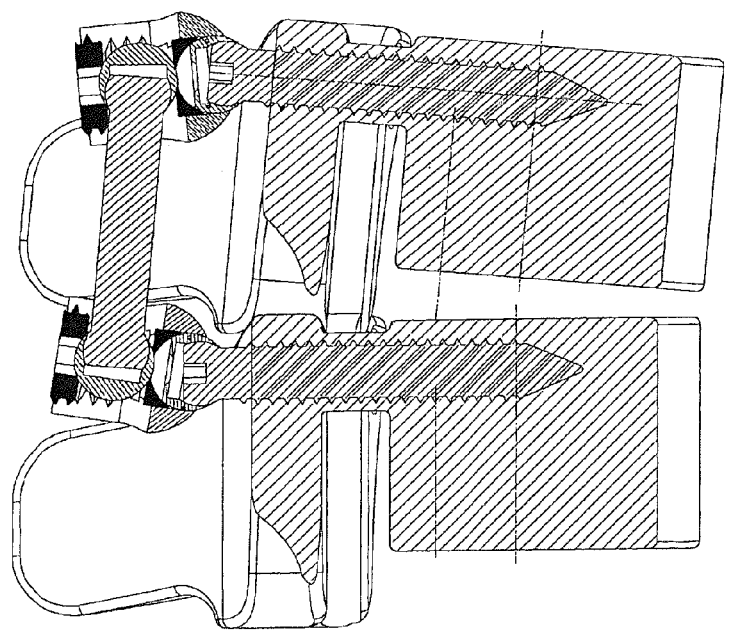

FIG. 15A shows a schematic representation of a spinal motion segment with the implanted dynamic screws of FIG. 6 and the dynamic rod assembly of FIG. 14A. FIG. 15B shows a cross-sectional view through the implanted screw assemblies with the vertebrae in neutral orientation relative to one another. The dynamic screws are implanted into vertebrae V1 and v2 and interconnected by the dynamic rod assembly. It should be appreciated that the vertebrae are represented schematically and those of ordinary skill in the art will recognize that certain anatomical features have been omitted for diagrammatic simplicity. FIG. 15C shows a cross-sectional view through the implanted screw assemblies with the vertebras in a relative flexion while FIG. 15D shows a comparable cross-sectional view with the vertebras in relative extension. These figures illustrate the movement of the dynamic components of the implanted devices during vertebral movement.

Figure 15F:
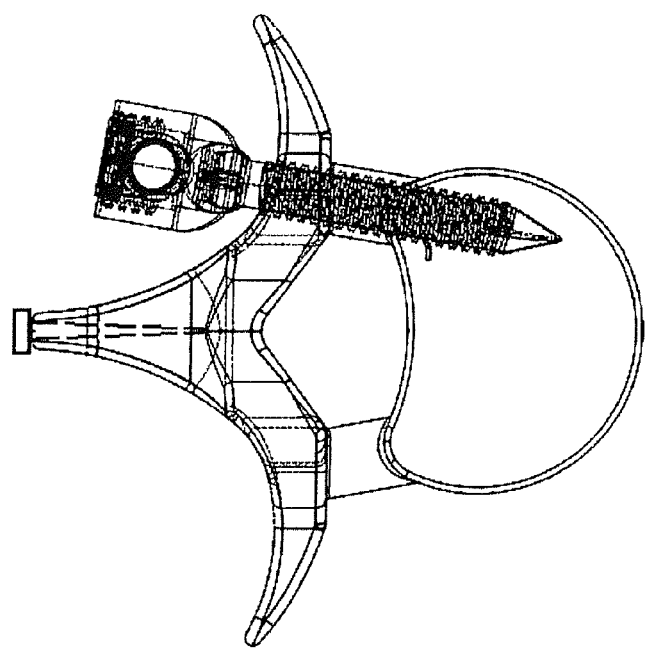
Figure 15E:
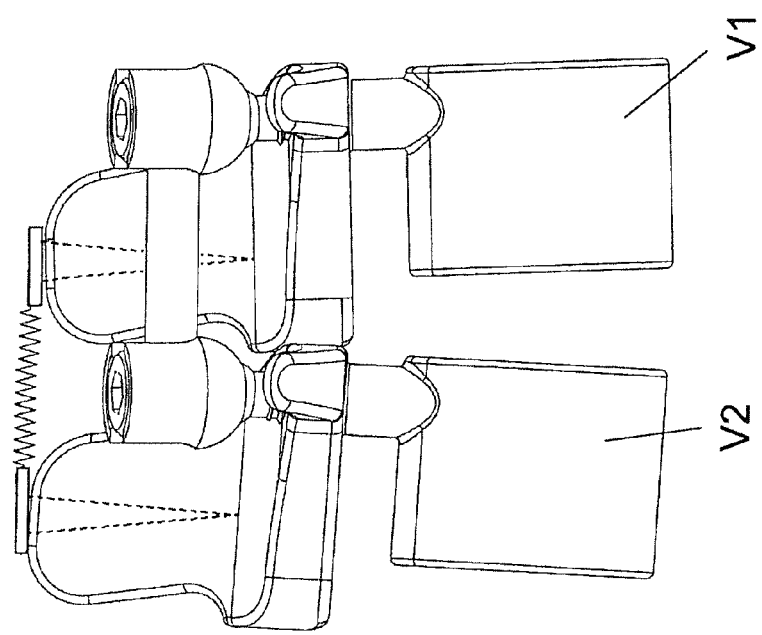

It should be appreciated that malleable members can be attached to various portions of the vertebra. For example, FIGS. 15E and 15F show lateral and axial views of a schematic representation of a spinal motion segment. A malleable member is attached to the spinous process of each vertebra and provides a biasing force onto the dynamic rod assemblies. In this embodiment, the dynamic rod of FIG. 14A may be used with dynamic or non-dynamic screw assemblies. (Non-dynamic screw assemblies are currently in common use and numerous embodiments have been disclosed in the art.) The dynamic rod functions as a fulcrum onto which the biasing force of the malleable spinous process member will act. When the biasing force is compressive (pushes the spinous processes towards one another), then the disc space and the anterior spinal column will be off-loaded and they will experience a decrease in overall load.

The configuration of the dynamic rod connecting assembly shown in FIG. 14A can be employed with other types of elongated members other than rods. For example, FIGS. 16A and 16B show a dynamic connecting assembly that employs an elongated plate member 1605. The plate member 1605 has a dynamic head assembly that includes a head 1610 that fits within and interacts with outer members 1615a and 1615b in the same manner as described above with respect to FIG. 15A. That is, with the head 1610 positioned within the interior aspect of the assembled outer members 1615, a cavity is formed above the surface of the head 1610. The cavity can contain any material adaptable for malleable use. As known by those of ordinary skill in the art, there are a host of materials and mechanisms that may serve as malleable structures. These include, but are not limited to, elastomeric substances, super elastic materials, memory shape materials, machined spring devices, hydraulic mechanism, magnets and/or any other appropriate materials/devices that will resist movement of the head 1610 relative to the inner aspect of the assembled members 1615. With relative motion between the members 1615 and the head 1610, the materials)/device(s) within the cavity will apply a force to the surface of the head 1610 and resist any movement of the elongated plate 1605 away from a neutral position.

Figure 17A:
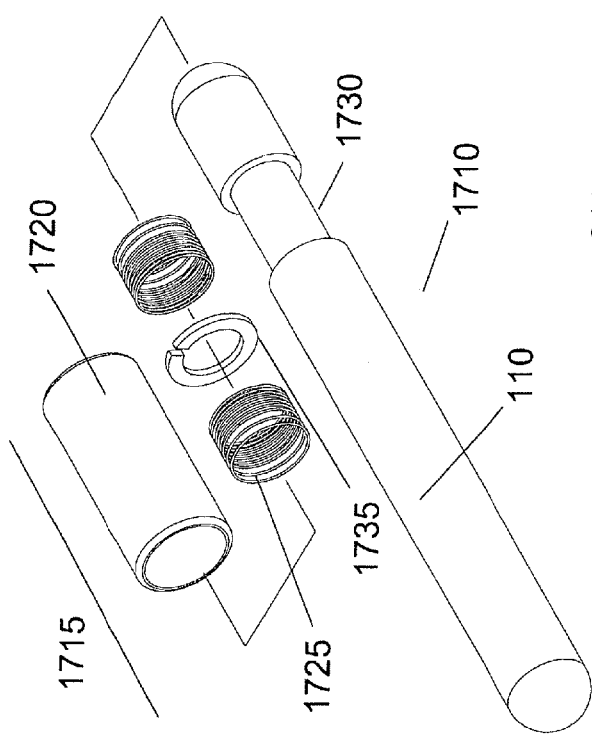
FIGS. 17A and 17B show exploded and side views, respectively, of a dynamic rod assembly.
Figure 17B:
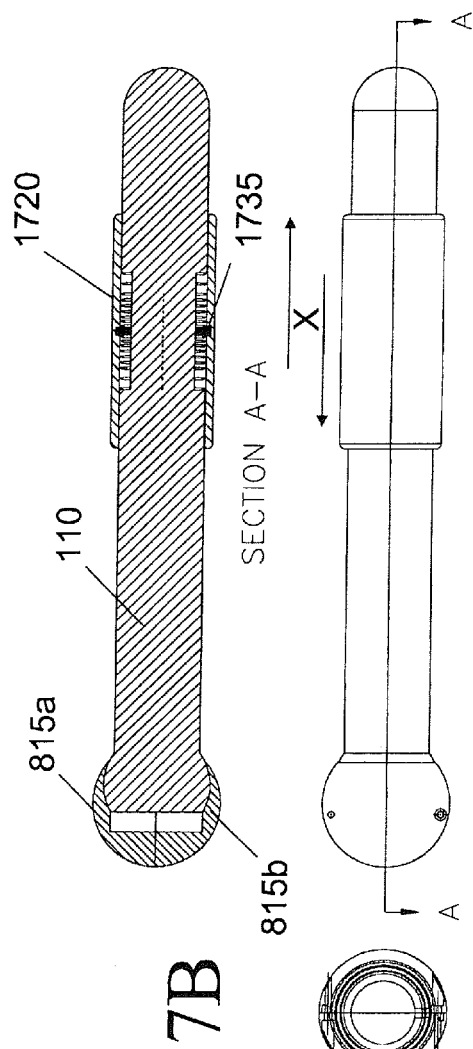

FIGS. 17A and 17B show exploded and side views, respectively, of a dynamic rod assembly 1710 that permits a bone screw assembly to be movably attached to a portion of a rod such as along a portion between first and second ends of the rod. The rod assembly 1710 includes a rod 110 and a dynamic sleeve assembly 1715 slidably mounted thereon. The assembly 1715 includes a sleeve 1720 sized to slidably mount on the rod 110, and one or more biasing members 1725 that fit within a channel 1730 on the rod 110. The biasing members 1725 fit within the channel 1730 beneath the sleeve 1720, as best shown in the cross-sectional view of FIG. 17B. An attachment member 1735, such as a washer, can be used to secure the sleeve 1720 to the rod 110.

The sleeve 1720 can slidably move along a direction X with respect to the rod 110. The biasing members 1725 bias the sleeve 1720 toward a neutral and resist any movement of the sleeve 1720 away from the neutral position. In an embodiment, one or both ends of the rod 110 has a dynamic connector assembly comprised of a pair of outer members 815a and 815b movably mounted on a head of the rod, such as was described above with reference to FIG. 8A-8D.

It should be appreciated that a dynamic rod assembly can include one or more dynamic features that permit movement along one or more portions of the rod relative to one or more other portions of the rod. The movement can be linear, curvilinear, pivoting, rotating and the like. FIGS. 18A-18E show various embodiments of rod assemblies with movable or articulating regions. For example, FIG. 18A shows a rod assembly formed of a first rod member 110a and second rod member 110b rotatably connected to one another via a dynamic rod connector 1805 of the type described above with reference to FIG. 8A-8C. The rod members 110a and 110b each have a dynamic sleeve assembly 1715 of the type described above in FIGS. 17A and 17B.

In another embodiment shown in FIG. 18B, the rod 110 has a dynamic sleeve assembly 1715 positioned in between first and second ends of the rod. The two ends 1815 of the rod 110 have dynamic connector assembly comprised of a pair of outer members movably mounted on a head of the rod, such as was described above with reference to FIG. 8A-8C. FIG. 18C shows another embodiment with a variation of the sleeve assembly 1715. In this embodiment, the sleeve assembly 1715 includes a sleeve 1825 that is integrally formed with one end of the rod member 110b. An end of rod member 110a is slidably mounted within the sleeve 1825 with biasing members urging the rod member 110a toward a neutral position relative to the rod member 110b. One or both ends of the rod assembly can include a dynamic head assembly comprised of a pair of outer members movably mounted on a head of the rod, such as was described above with reference to FIG. 8A-8C.

FIG. 18D shows another embodiment that includes a first rod member 110a and a second rod member 110b that are movably coupled to one another in both linear and rotational movement. A coupling rod member 110*c* forms a sleeve that slidably houses an end region of the rod member 110*a* to permit linear movement that is biased toward a neutral position via biasing member 1725. The coupling rod member 110*c* also forms an outer housing 1820 that rotatably couples to a rounded end of the rod member 110*b*, such as in the manner described above with reference to the dynamic connector of FIG. 8A-8C. FIG. 18E shows another embodiment that combines the various dynamic assemblies described above in a single rod assembly.

FIGS. 19A and 19B show exploded and cross-sectional views, respectively, of another embodiment of a dynamic rod assembly. This embodiment includes first and second rod members 110*a* and 110*b*, each having heads with dynamic rod connectors of the type described above with reference to the dynamic connector of FIG. 8A-8C. The rod members 110 are movably connected via a dynamic assembly 1905 that includes a connector 1910 with a pair of articulating portions 1915. The ends of the connector 1910 couple to respective ends of the rod members 110*a* and 110*b* as shown in FIG. 19B. An outer sleeve 1925 is formed of two members that mount over the connector 1910 and the rod members 110 with a pin P keeping the device in an assembled state. The dynamic assembly 1905 permits movement of the rod members 110*a* and 110*b* relative to one another.

Figure 20:
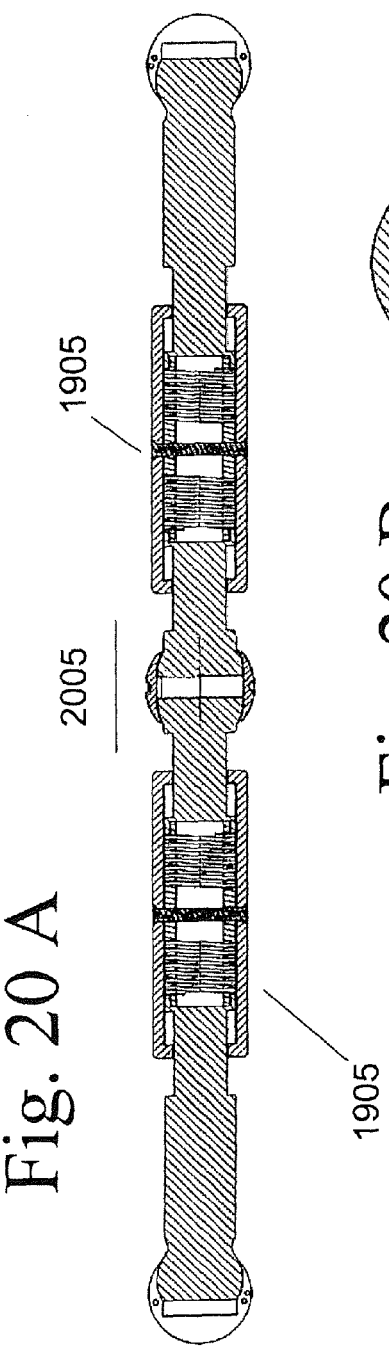
FIG. 20A shows another dynamic rod assembly.
FIGS. 20B and 20C show enlarged assembled and exploded views, respectively, of a dynamic connector.
Figure 20:
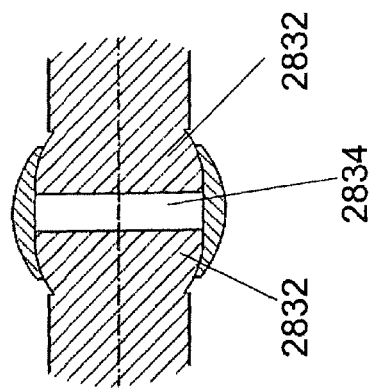
Figure 20C:
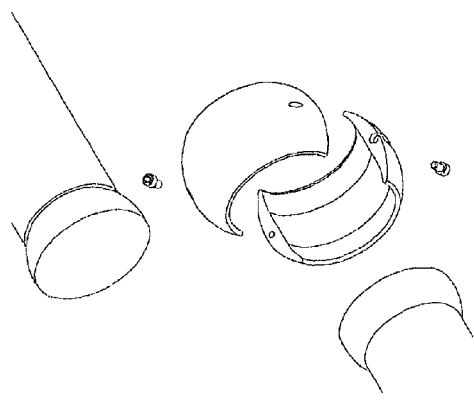

FIG. 20A shows another dynamic rod assembly that employs dynamic assemblies 1905 of the type described above with reference to FIG. 19A-19B. The rod assembly of FIG. 20A includes a central dynamic connector 2005 that dynamically connects first and second rod members 110*a* and 110*b* to one another in the manner of the dynamic rod connector described above with reference to the dynamic connector of FIG. 8A-8C, FIGS. 20B and 20C show enlarged assembled and exploded views, respectively, of the dynamic connector 2005. In the assembled device, cavity 2834 is formed between each of the flat surfaces 2832 that comprise the superior surface of each spherical end of rod members 110. Cavity 2834 can contain any material adaptable for malleable use. These include, but are not limited to, elastomeric substances, super elastic materials, memory shape materials, machined spring devices, hydraulic mechanism, magnets and/or any other appropriate materials/devices that will resist movement of the surface 2832 relative to the inner aspect of the assembled connector 2005.

Figures 21A, 21B:
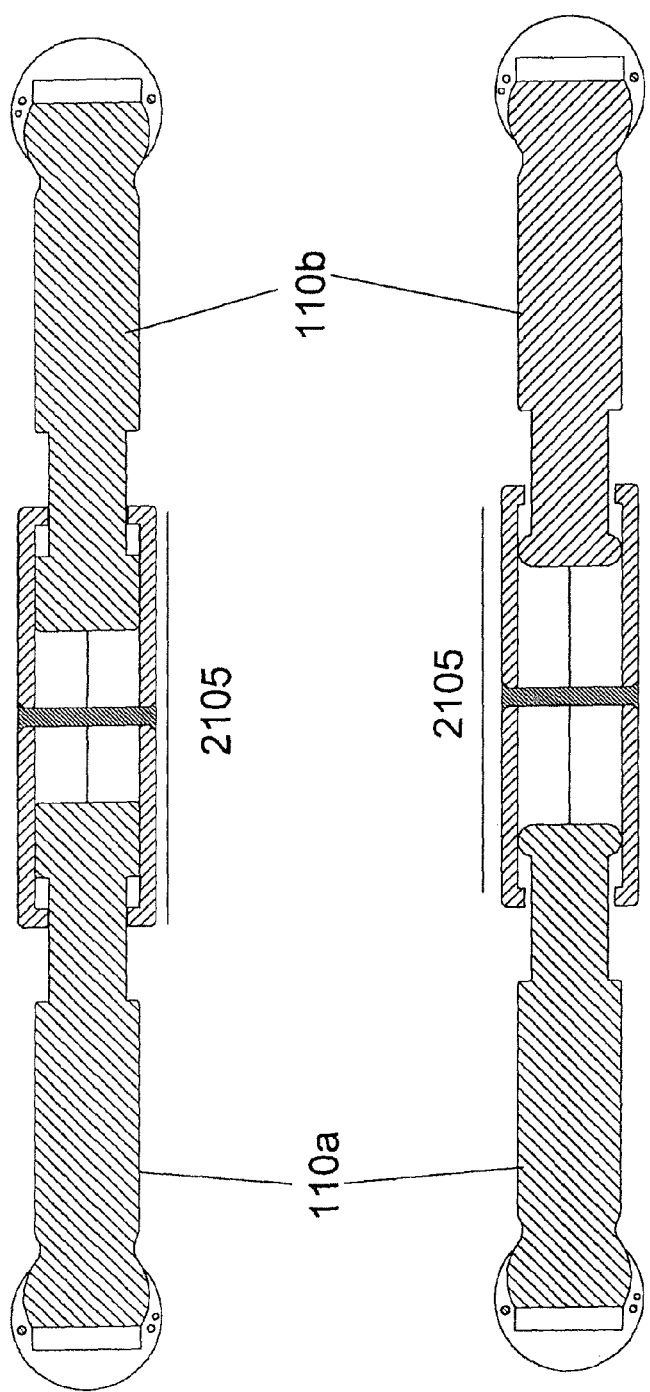
FIGS. 21A and 21B show additional embodiments of dynamic rod assemblies with central dynamic connector connecting first and second rod members.

FIGS. 21A and 21B show additional embodiments of dynamic rod assemblies with central dynamic connector connecting first and second rod members 110*a* and 110*b*. The first and second rod members 110 are movably connected via a central dynamic connector 2105 formed of an outer sleeve that defines an inner cavity in which the ends of the first and second rod members 110*a* and 110*b* are movably positioned.

Figure 22A:
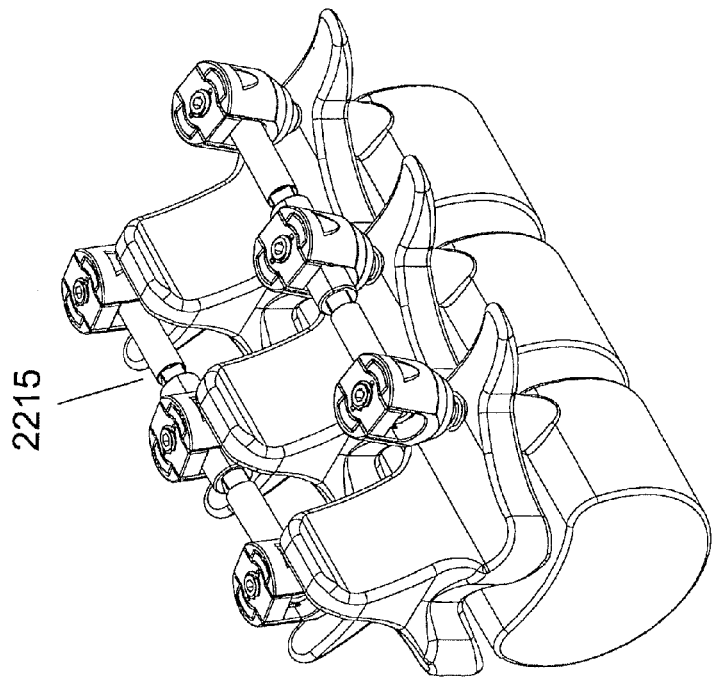
FIG. 22A shows a portion of a spine with vertebrae V1, V2, and V3.
Figure 22B:
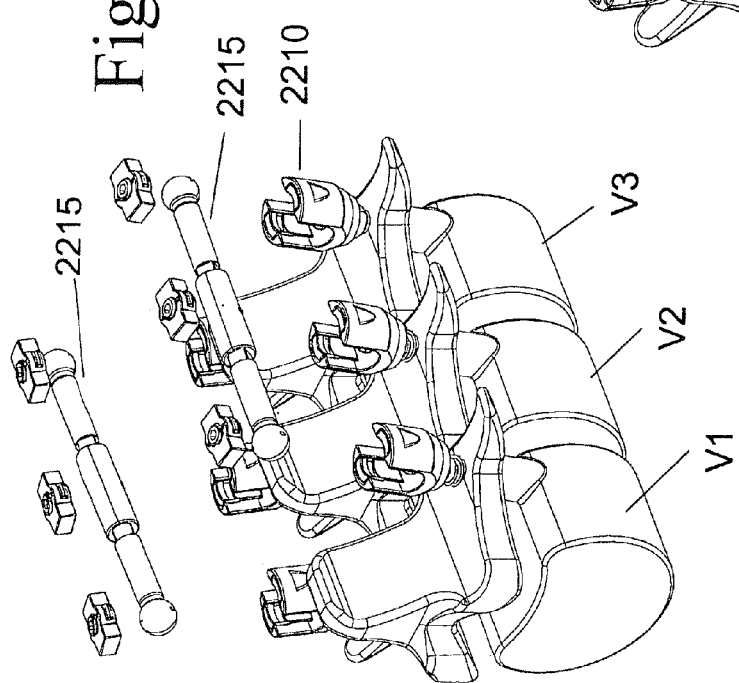
FIG. 22B shows the portion of the spine with dynamic rod assemblies interconnecting the screw assemblies.

FIG. 22A shows a portion of a spine with vertebrae V1, V2, and V3. At least one screw assembly 2210 (which may be a dynamic screw assembly) is attached to each of at least two vertebras. The screw assemblies can be interconnected via a dynamic rod assembly, which can be of any embodiment or combination of embodiments of the dynamic rod assemblies described herein. FIG. 22B shows the portion of the spine with dynamic rod assemblies interconnecting the screw assemblies. The dynamic rod assemblies permit interconnection of the screw assemblies while permitting at least some movement (linear, curvilinear, rotational or combinations thereof) between the screw assemblies and attached vertebrae.

FIGS. 23 to 25 illustrate a method for the use of dynamic screw and rod assemblies to correct aberrant vertebral alignment while maintaining relative vertebral motion. FIG. 23 shows a side view of a portion of a spine with a plurality of vertebrae that are offset from one another. The illustrated vertebrae have a concave curvature K in the sagittal plane. This alignment is termed kyphosis and would be an aberrant curvature if found in the cervical or lumbar segments of the spine. Abnormal spinal alignment is traditionally corrected by interconnecting a series of bone screws with a rod contoured to the desired curvature. With the rod in place, the bones are forcibly repositioned into the desired alignment by the rigid rod and the bones are then immobilized and fused in that position.

In the dynamic correction of a kyphotic alignment, dynamic bone screws are placed into the spine with the central screw(s) at a greater height from the bone surface than the end screws. FIG. 24 shows the spinal segment after bone screw assemblies 2210 have been attached to vertebrae and prior to attachment of a dynamic rod assembly 2215 to the bone screw assemblies. At placement, the dynamic rod is transiently deflected to conform to each screw position. Once seated, the malleable members within the dynamic rod will collectively act to return the rod to the neutral position and realign the attached bones. FIG. 25 shows the spine portion after the dynamic rod assembly has been used to link the bone screw assemblies 2210. As shown, the curvature is re-aligned into a convex (lordotic) configuration.

FIG. 26A shows an assembled view of a cross-connector 2610 connecting a pair of elongated fixation rods 110 on either side of the vertebral midline. FIG. 26B shows an exploded view of the cross-connector 2610. The cross-connector 2610 includes a cross-connecting rod 2610 that can include any of the embodiments of the dynamic rod, head, and screw features described above. The rod 2610 is described in detail below. The ends of the rod 2610 are coupled to rods 110 via coupler assemblies 2615 in a manner that permits dynamic movement between the rod 2610 and the rods 110.

FIG. 27A shows perspective views of a bracket member 2710 of the coupler assembly 2615. The bracket member 2710 is a housing that defines an internal cavity 2715 that receives a locking block 2720, which is shown below in detail with reference to FIG. 27B. The bracket member 2710 has a rounded slot 2725 that is sized and shaped to receive a rod 110. FIG. 27B shows the locking block 2720 of the coupler assembly 2615. As mentioned, the locking block is sized and shaped to fit within the cavity 2715 of the bracket member 2710. The locking block 2720 has an enlarged lower region 2722 and a shaft that interfaces with a locking screw. The locking screw 2730 (threads not shown) interfaces with the locking block 2710 to incrementally tighten the locking block 2720 (threads not shown) into the bracket member. FIG. 27C shows perspective assembled views of the coupler assembly 2615. The slot 2725 defines a space where the rod 110 can be positioned. The locking screw 2730 can be tightened to raise the locking block 2720 such that the enlarged region 2722 abuts against the rod 110 to lock the rod within the coupler assembly 2615.

Figure 28A:
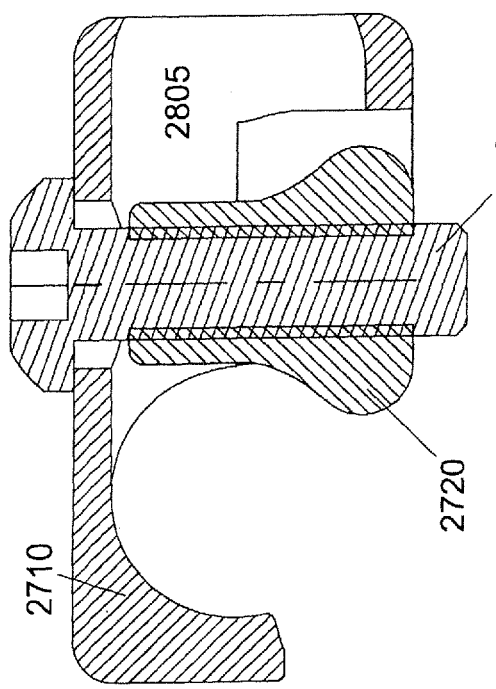
FIG. 28A shows an enlarged view of the coupler assembly with the locking block positioned in the bracket member.
Figure 28B:
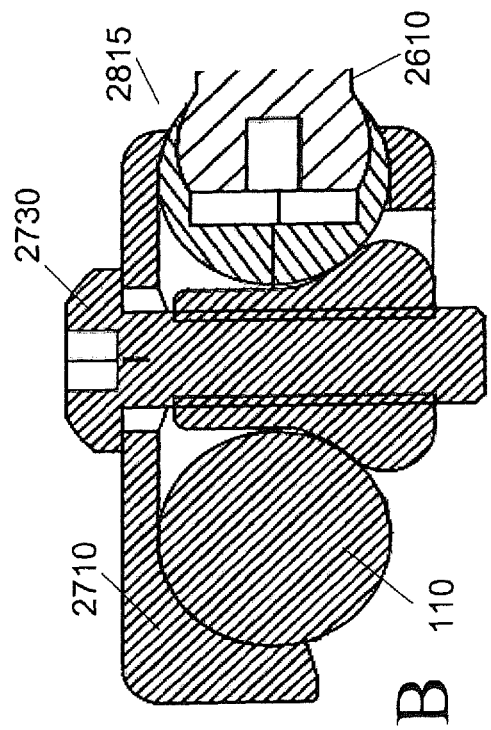
FIG. 28B shows the coupler assembly with the rods.

FIG. 28A shows an enlarged view of the coupler assembly 2615 with the locking block 2720 positioned in the bracket member 2710. The locking screw 2730 is positioned within the locking block 2720. The bracket member 2710 defines a space 2805 that is sized and shaped to receive a dynamic head connector assembly 2815 of the rod 2610 of the cross-connector. FIG. 28B shows the coupler assembly 2615 with the rod 110 and rod 2610 positioned in the bracket member 2710. The dynamic head assembly 2815 is configured pursuant to the dynamic head assembly discussed above with reference to FIGS. 8A-8C. The locking screw 2730 is tightened to raise the locking block 2720 such that the enlarged region pushes against the heads of the rods 110 and 2610 to secure them within the bracket member 2710. The dynamic head assembly 2815 permits relative movement between the rod 2610 and the bracket member 2710.

FIG. 29 shows perspective and cross-sectional views of the rod assembly 2610 of the cross-connector 2610. The rod assembly 2610 includes first and second rod members 2910*a* and 2910*b* that are slidably connected to one another. The rod members 2910 can slidably move relative to one another. As shown in the side view of FIG. 29, the rod members 2910 collectively form a single rod. Each rod member 2910 includes a respective dynamic head assembly comprised of a pair of outer members movably mounted on a head of the rod, as described above with reference to FIGS. 8A-8D.

Figure 30:
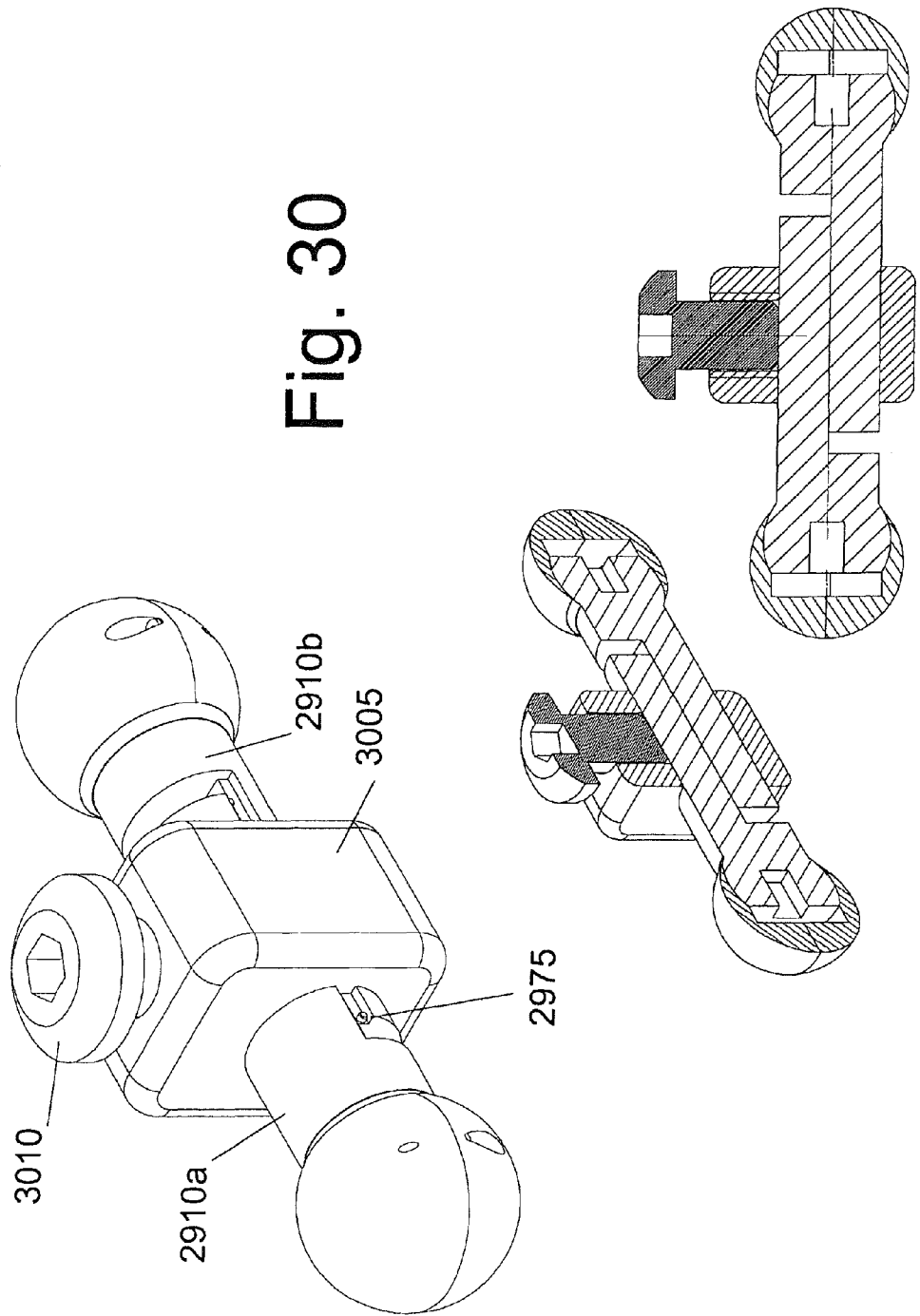
FIG. 30 shows the rod assembly with a clamping member on the rod members.
Figure 31:
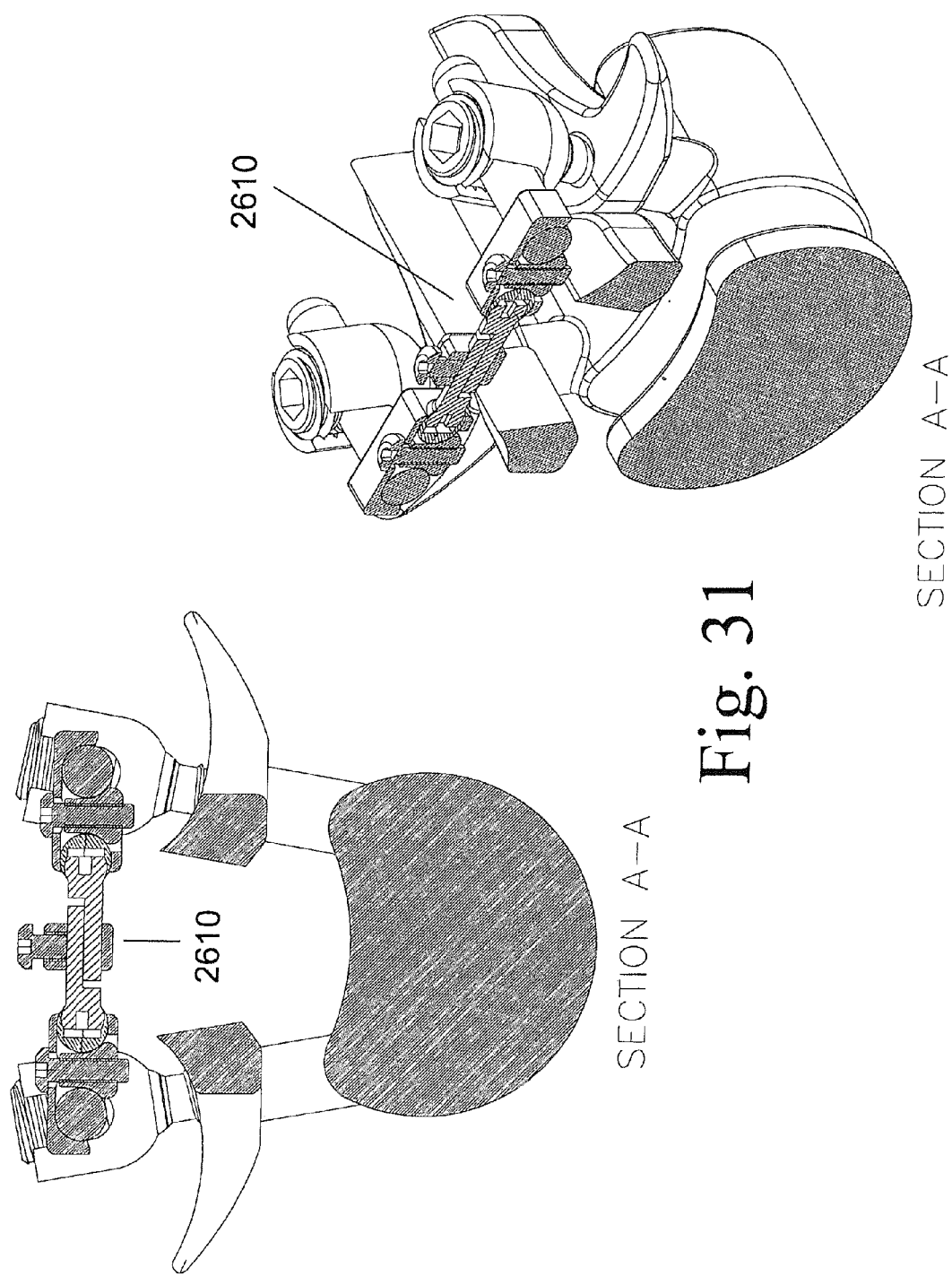
FIG. 31 shows side and perspective cross-sectional views of the cross connector connected to a pair of screw assemblies that are implanted on vertebrae.

FIG. 30 shows the rod assembly 2610 with a clamping member 3005 on the rod members 2910*a* and 2910*b*. The clamping member 3005 serves to secure the rod members 2910*a* and 2910*b* to one another and can be used to tighten the members in a fixed position relative to one another. Toward this end, the clamping member 3005 includes a locking nut 3010 that can be tightened into the clamping member 3005 to press the members 2910*a* and 2910*b* into a fixed relationship. Pin 2975 is placed into at least one side of each rod member 2910 and acts to prevent the disassembly of the assembled device. FIG. 31 shows side and perspective cross-sectional views of the assembled construct wherein dynamic cross connector 2615 is connected to a pair of interconnecting rods.

FIG. 32A shows a cross-sectional view of an additional dynamic connector. Connector 2685 is used to interconnect two bone screw assemblies. The latter may be dynamic, as illustrated, or non-dynamic. While connector 2685 contains a central coupler assembly that is similar to the central coupler assembly 2615 of FIG. 28A, the coupler of the current embodiment is adapted to accept a dynamic head assembly on either side of the central locking screw. The dynamic head assembly is configured pursuant to the dynamic head assembly discussed above with reference to FIGS. 8A-8C. The current embodiment advantageously permits each rod portion 110 to be positioned independently of the other rod. With actuation of the locking screw of the central coupler, the relative position of each rod member is locked but motion is still permitted because of the action of the dynamic head assemblies. FIG. 32B shows a schematic representation of the dynamic connector linked to dynamic screw assemblies. In FIG. 32C, a schematic representation of another embodiment is shown wherein an additional dynamic head assembly is positioned on the distal end of at least one of the rod portions 110.

FIG. 33A shows a perspective view of a bone screw assembly 3300. FIG. 33B shows a perspective view of the assembly 3300 in an exploded state. The assembly 3300 includes a bone screw 3305 that couples to an orthopedic connecting member 3310. While the connecting member 3310 is represented as a plate, it could represent any alternative device adapted to connect bone screws, such as, for example, a rod configured into a closed or open loop. The assembly 3300 includes a dome shaped coupler 3315 that interfaces with a set screw 3320, as described below. The bone screw 3305 has a proximal head that fits within first and second housing members 3325*a* and 3325*b*. An elongated threaded section 3330 extends upwardly from the housing member 3325*b* and fits through a hole 3335 in the connecting member 3310.

Figure 34:
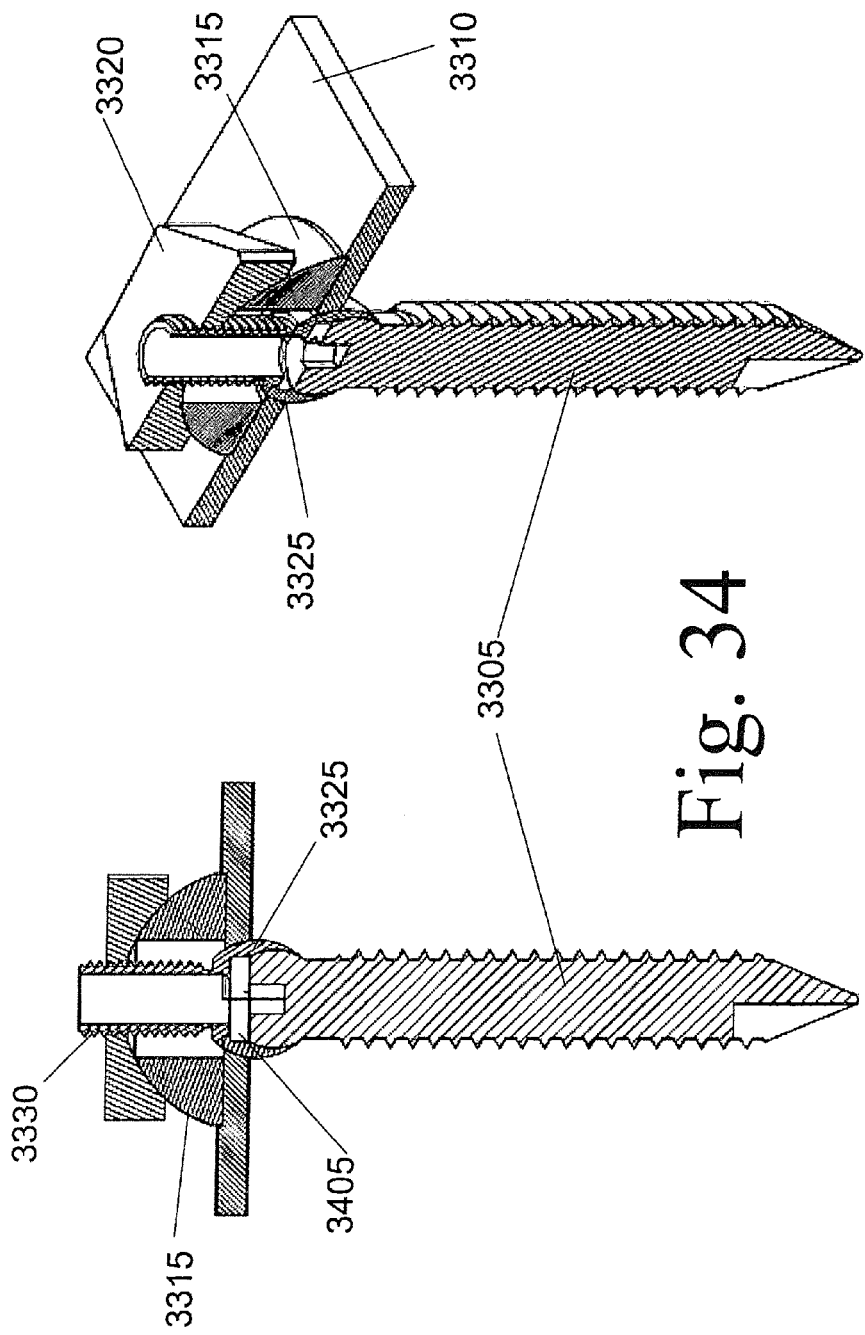
FIG. 34 shows side and perspective cross-sectional views of the assembly.

FIG. 34 shows side and perspective cross-sectional views of the assembly 3300. The first and second housing members form a space 3405 that can contain a material or structure that resists movement of the head of the bone screw 3305 relative to the inner aspect of the inner housing members. The material or structure within the space 3405 can be, for example, elastomeric substances, super elastic materials, memory shape materials, machined spring devices, hydraulic mechanism, magnets and/or any other appropriate materials/devices that will resist movement of the head of the bone screw relative to the inner aspect of the housing members. When the screw head is moved out of a predetermined position in the inner housing members, the material/device within space 3405 will apply a force to the head of screw and resist any bone screw movement away from the neutral position. The assembly is adapted to return the screw and the attached bone to the neutral position once the deflecting force has dissipated.

The elongated threaded section 3330 extends upwardly through the connecting member 3310 and threadedly mates with the locking nut 3320. When the locking nut 3320 is not fully tightened, the screw head 3325 and members 3325 can rotate relative to the dome shaped coupler 3315 by virtue of a domed interface 3410 between the locking nut 3320 and the dome shaped coupler 3315. In this first state, the screw 3305 can be freely rotated relative to the connector member. As the locking nut 3320 is tightened downwardly against the dome shaped coupler 3315, it compresses against the dome shaped coupler 3315 to lock against the dome-shaped coupler 3315 and fixate it relative to the connector member 3315. In this second state, the screw head can rotate at least slightly within the members 3325 but are biased toward a neutral position by virtue of the material/device within space 3405.

Figure 35:
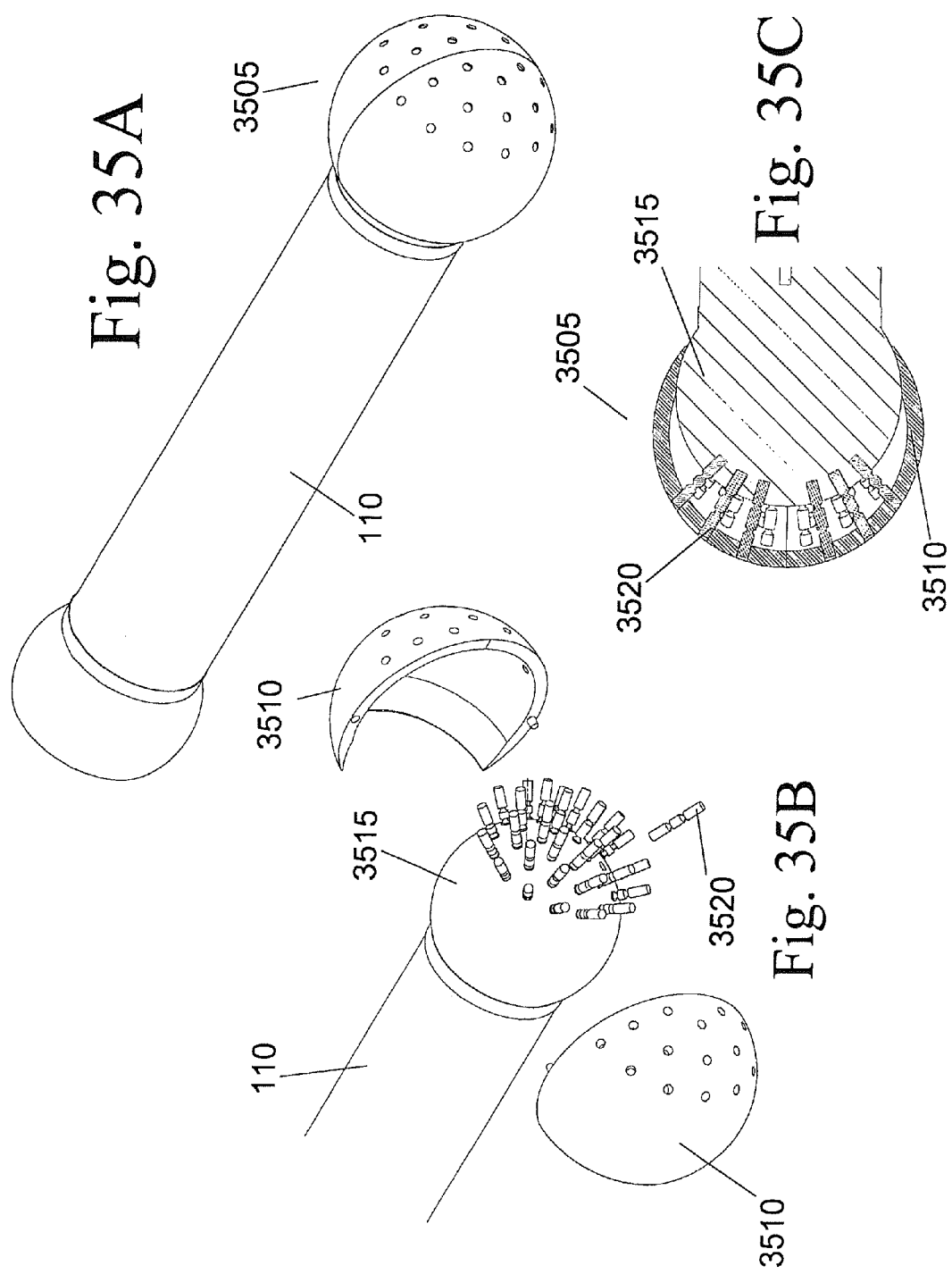
FIG. 35A shows a perspective view of a connecting rod with dynamic heads on opposite ends of the rod.
FIG. 35B shows an exploded view of a head of the 110.
FIG. 35C shows a cross-sectional view of the head in an assembled state.

FIG. 35A shows a perspective view of a connecting rod 110 with dynamic head assembly 3505 on at least one end of the rod 110. The head assembly 3505 is adapted to permit movement of the rod 110 relative to at least a portion of the head 3505. FIG. 35B shows an exploded view of a head 3505 of the rod 110. FIG. 35C shows a cross-sectional view of the head 3505 in an assembled state. The head 3505 includes a pair of outer members 3510 that surround a central head 3515 which is rigidly attached to the rod 110. One or more elongated flexible members 3520 extend between the central head 3515 and the outer members 3510. The flexible members 3520 are adapted to change shape in response to a force applied thereto but are biased toward a default state that maintains the outer members 3510 in a default position relative to the central head 3515.

Thus, the outer members 3505 can move relative to the central head 3515 when a force is applied thereto wherein the flexible members 3520 change shape in response to such movement. However, the flexible members 3520 urge the outer members 3505 back to a default position after the force has been removed. In this manner, the rod 110 and head 3515 are permitted at least some relative movement with respect to outer member 3510. In another embodiment, the space between head 3515 and outer member 3510 may be alternatively (or additionally) filled with an elastomeric substance that would bias movement within assembly 3505 towards a neutral position. In another embodiment, the outer surface of head 3515 is adapted to circumferentially abut the inner aspect of member 3510 so that no significant space is formed between them. The bore placed within member 3510 for rod 110 to exit the inner aspect of 3510 is sufficiently sized so that head 3515 can move relative to 3510. No biasing member is contained within to act upon the members and restore them to a neutral position once a deflecting force has dissipated. The range of motion between the members is preferably, but not necessarily, less than twenty one degrees.

Figure 36:
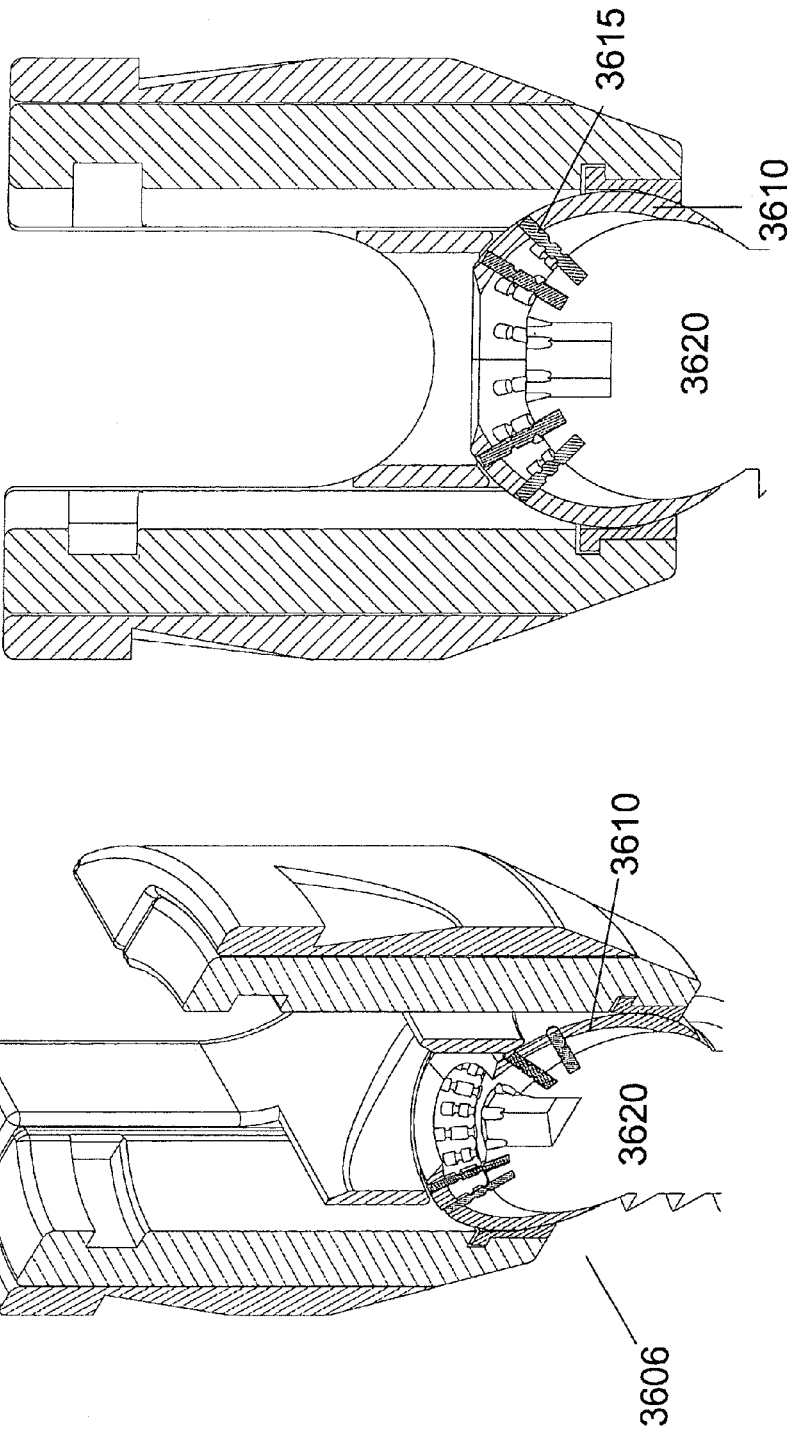
FIG. 36 shows an embodiment of a bone screw assembly.

FIG. 36 shows an embodiment of a bone screw assembly 3606. The bone screw assembly 3606 includes a screw with a head assembly 3606 positioned in outer members 3610. One or more flexible members 3615 couple a central screw head 3620 to the outer members 3615 to permit relative movement therebetween. The flexible members 3615 bias the central screw head 3620 toward a default position in the manner described above with reference to FIGS. 35A-35C. The described embodiments of dynamic head 3505 may be alternatively used.

FIG. 37A shows a perspective view of a rod 110 with a dynamic head assembly 3705. FIG. 37B shows the rod 110 with the dynamic head assembly 3705 in an exploded state. FIG. 37C shows a cross-sectional view of the rod. The dynamic head assembly 3705 includes first and second outer members 3710a and 3710b that collectively surround a central head 3715 that is partially spherical in shape. Member 3710a may be circumferentially solid, as depicted, or it may be alternatively split longitudinally (in a direction parallel to the long axis of rod 110) to form a "C" ring configuration. In assembly, the outer members 3710a and 3710b are joined to form a form outer member 3710 using head shrink coupling, threaded screws, ratchets, clips, adhesives, or any other appropriate technique for segment assembly. The central head 3715 extends from at lease one end of rod 110 such that a section 3720 of reduced diameter is positioned between the rod 110 and the central head 3715. As best shown in FIG. 37C, the central head 3715 is sized such that a cavity is located inside the outer members 3710 with a biasing member 3725 positioned inside the cavity. In addition, a wedge shaped bore 3730 is located in the outer members 3710a.

The outer members 3710 are adapted to move relative to the central head 3715 in response to forces applied thereto. The curvilinear surface of head 3715 forms a bearing surface with the inner aspect of member 3710b and permits rotational movement therebetween as limited by the amount of play between the wedge-shaped bore 3730 and the section 3720. The biasing member 3725 biases the outer members 3710 toward a default position when the outer members 3710 are moved away from the default position relative to the central head 3715.

FIG. 38A shows a perspective view of a rod 110 with a dynamic head assembly 3805. FIG. 386 shows the rod 110 with the dynamic head assembly 3705 in an exploded state. The dynamic head assembly 3805 includes first and second outer members 3810a and 3810b that collectively surround a section 3815 of the rod 110. A plurality of rounded protrusions 3820 extend outwardly from the section 3815. The protrusions 3820 are interspersed around the circumference of the section 3815. A plurality of longitudinally-extending slots 3825 are also interspersed around the circumference of the section 3815. The slots 3825 permit the section 3815 to flex inwardly and outwardly with respect to a central rod section 3830.

FIG. 39A shows a side cross-sectional view of the rod 110. FIG. 39B shows a cross-sectional view of the rod looking along the axis of the rod 110. The outer member 3810b is sized relative to the section 3815 such that a cavity 3905 is located inside the outer member 3810b. Because of angled circumferential wall 3811, cavity 3905 has a conical configuration that is toped by wall 3812. The protrusions 3820 abut an inner aspect of the outer members 3810 at the junction between the outer member 3810a and the outer member 3810b. The inner aspect of the outer member 3810a curves radially inward toward the section 3815 to form a shoulder 3910 that abuts the protrusions 3820. As before, members 3810a and 3810b are joined to form a form outer member 3810 using head shrink coupling, threaded screws, ratchets, clips, adhesives, or any other appropriate technique for segment assembly.

With the device in the assembled state, dynamic head assembly 3805 and rod 110 are movable relative to one another and exhibit a biasing force that returns the two members to a neutral relative position after the influence of a deflecting force has dissipated. In response to movement between the two members 3805 and 110, protrusions 3820 are forced away from the neutral position that lies at the junction between the outer member 3810a and the outer member 3810b. The constricting inner surfaces of members 3810 produce an inward deflection of protrusions 3820 and sections 3815. The material used for device manufacture will inherently resist deformation of the base of section 3815 and provide a biasing force that favors the neutral position. In this way, the dynamic assembly is biased toward a default state and urges the outer members 3810 toward a default position relative to the rod 110.

FIG. 40A shows a perspective view of a rod 110 with a dynamic head assembly 4005 in an exploded state. FIG. 40B shows the rod 110 with the dynamic head assembly 4005 in an assembled state. FIG. 40B also shows a cross-sectional view of the rod. The dynamic head assembly 4005 includes first and second outer members 4010a and 4010b that collectively surround one end of rod 110, wherein a lip 4020 with a curvilinear undersurface is located. In assembly, the undersurface of lip 4020 forms a bearing surface with inner surface of member 4010a. An elongated extender member 4030 extends outwardly from the rod 110 along the central axis of the rod. As best shown in FIG. 40B, the extender member 4030 is slidably positioned in a bore within the rod 110. A biasing member 4035, such as a spring, is located within the bore to bias the extender member 4030 outwardly from the bore.

With reference to FIG. 408, the outer member 4010b couples to the outer member 4010a to form a dynamic head assembly 4005. The outer member 4010b has an inner contour that is conical. The inner contour of member 4010a is complimentary to the undersurface of lip 4020 and both are preferably spherical. An end of the extender member 4030 abuts the crest of the wedge-shaped inner aspect of the outer member 4010b. The interaction between the end of the extender member 4030 and the inner aspect of outer member 4010b provides a biasing force that favors a neutral position. As illustrated, dynamic head assembly 4005 and rod 110 are movable relative to one another and the biasing force provided by member 4030 will act to return the two members to a neutral relative position after the influence of a deflecting force has dissipated.

FIGS. 41A and 41B show cross-sectional views of a dynamic bone screw assembly. The assembly 4100 includes a housing 4105 that receives a bone screw 4110 through an inner bore in the housing 4105. The housing 4105 includes a slot that receives a rod 110. A first locking nut 4120 can be used to lock the bone screw 4110 relative to the housing 4105 by providing a downward force against the head of the bone screw 4110 that immobilizes the bone screw within a seat inside the housing 4105. Likewise, a second locking nut 4125 can be used to lock the rod 110 relative to the housing 4105 by pressing the rod 110 downward against a bottom surface of the slot. The housing 4105 includes a flexible or articulating region 4130 that is configured to enable a first region of the housing 4105 to move relative to a second region of the housing 4105, as described below.

Figure 42B:
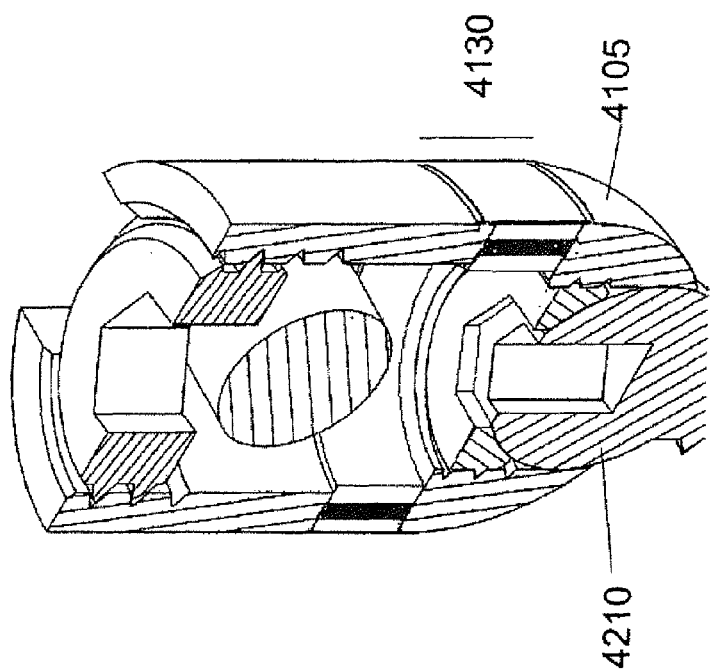
FIGS. 42A and 42B show cross-sectional views of a housing region of the assembly of the assembly of FIG. 41A.
Figure 42A:
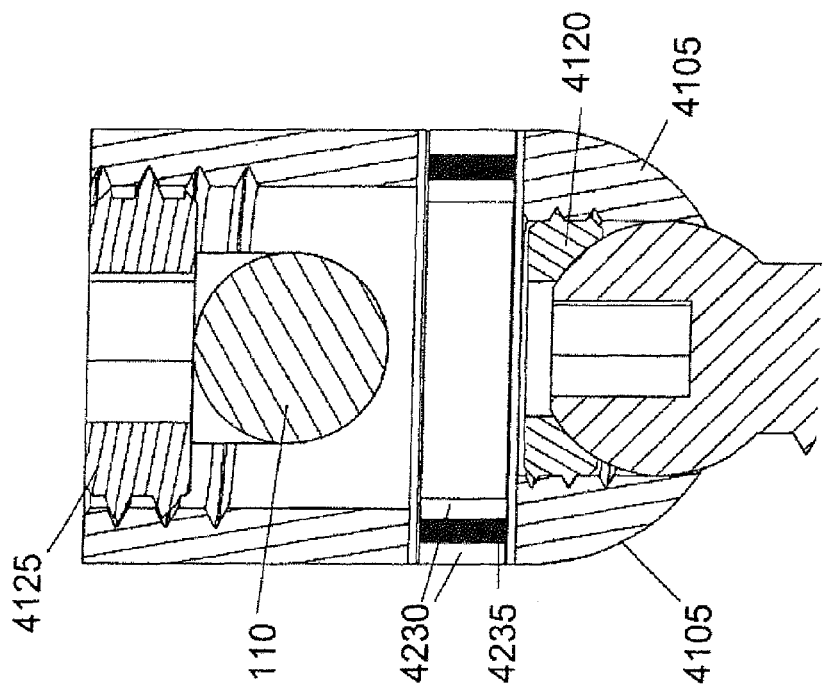

FIGS. 42A and 42B show cross-sectional views of the housing region of the assembly of the assembly of FIG. 41A. The screw 4110 has a shank that extends from a head 4210. The head 4210 sits within a seat formed within the bottom region of the housing 4105. The first locking nut 4120 has threads that engage corresponding threads inside the housing 4105. The first locking nut 4120 can be advanced downward to exert a force on the head 4210 of the screw 4110 to thereby immobilize or lock the screw 4110 relative to the housing 4105. The screw head and/or the seat in which it sits may be serrated, textured, coated, corrugated or otherwise treated in any manner intended to increase the frictional forces between them so as to potentate the locking mechanism. These features may be equally applied to any other embodiment disclosed in this application.

The rod 110 sits within the channel in the housing 4105. The second locking nut 4125 engages a threaded region in the housing 4105 and can be advanced downward against the rod 2215. The second locking nut 4125 provides a downward force to press the rod 110 against the bottom of the channel and immobilize the rod 110 relative to the housing 4105.

As mentioned, the region 4130 of the housing is configured to enable a first region of the housing 4105 to move relative to a second region of the housing 4105. The region 4130 enables the region of the housing that is locked to the rod 110 to move relative to the region of the housing that is locked to the screw 4110. In this manner, the region 4130 permits the rod 110 to move relative to the screw 4110 while both the rod and screw are immobilized relative to the housing 4105.

The region 4130 can be configured in various manners so as to permit such movement. In the illustrated embodiment, the region 4130 is at least partially filled with a malleable material 4230, such as elastomer (polyurethane, rubber, and the like), that can deform. This permits the region 4130 to elastically flex or deform such that the segment of the housing 4105 above the region 4130 can move relative to the segment below the region 4130. The region 4130 also contains a material such as a braided wire or cable 4235 that is preferably imbedded within the malleable material 4230 and acts to resist the distraction and separation the region of the housing that is locked to the rod 110 from the region of the housing that is locked to the screw 4110. The malleable material 4230 will provide a biasing force that returns the two housing regions on either side of region 4130 to a neutral relative position after the influence of a deflecting force has dissipated.

Figure 44:
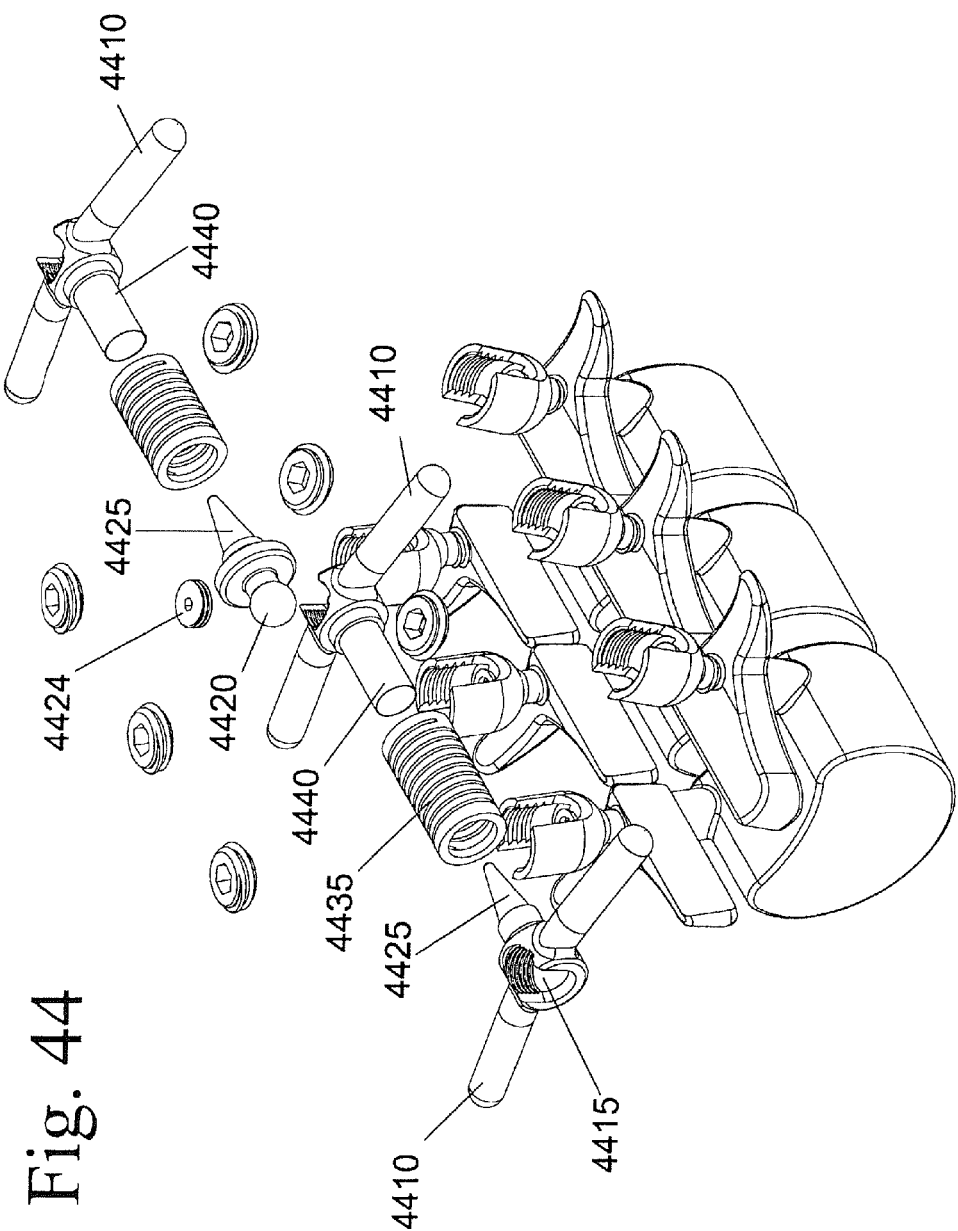
FIG. 44 shows an exploded view of the modular dynamic connectors.
Figure 45:
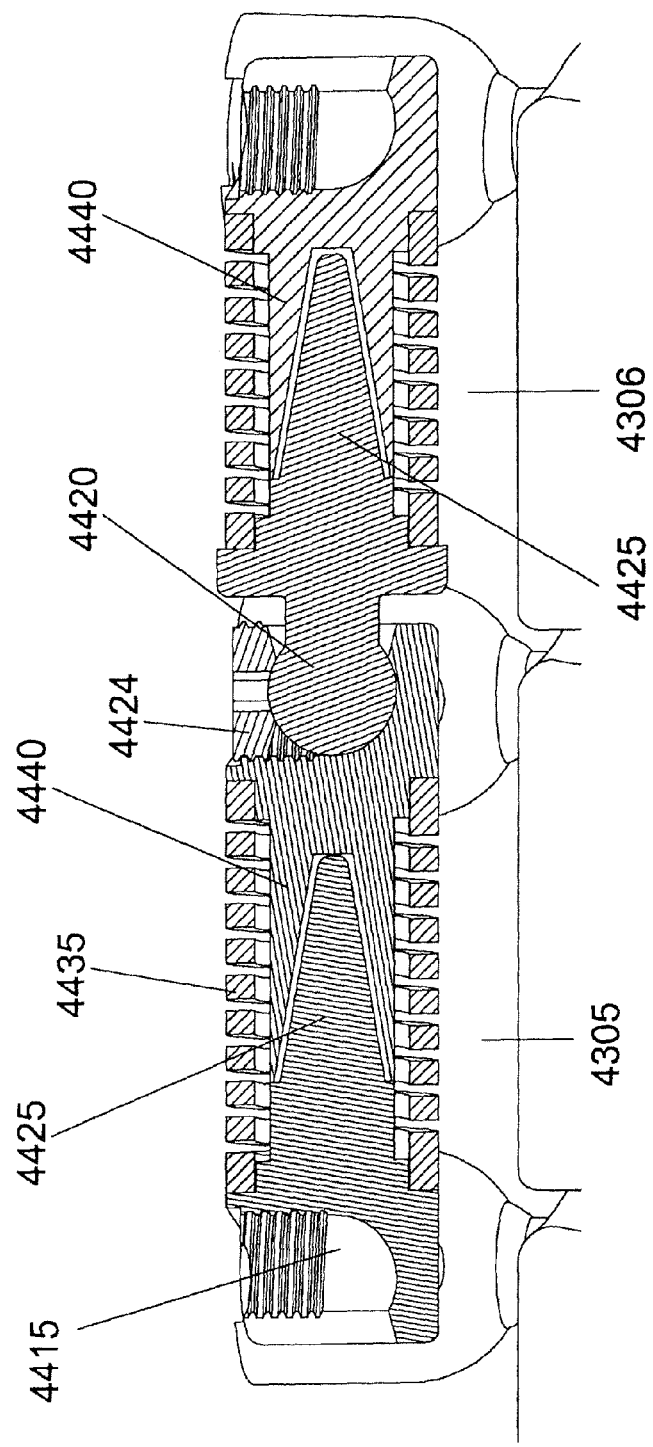
FIG. 45 shows a cross-sectional view of the implanted modular dynamic connectors.

FIGS. 43A and 43B show an embodiment of two modular dynamic assemblies 4305 and 4306 that are adapted to link bone screw assemblies to one another across the vertebral midline. FIG. 44 shows an exploded view of modular assemblies 4305 and 4306 while FIG. 45 shows a cross-sectional view of the two implanted dynamic assemblies. Dynamic assembly 4305 has a rod cross-member 4410 at each end of the device. As illustrated, each rod 4410 is rigidly affixed onto two bone screw assemblies, wherein each of the two screw assemblies is attached onto an opposite side of the vertebral midline of a single vertebra. Each rod 4410 contains a central coupler member 4415 that is adapted to removably couple to a second coupler 4420 of a complimentary modular dynamic assembly 4306. Assembly 4306 contains a ball-like coupler 4420 on one end and a rod cross-member 4410 with a coupler 4415 on another end.

In an embodiment, the first coupler 4415 is a cup-like member that removably receives therein the second coupler 4420, which is comprised of a ball-like member. After attachment of the two couplers, a locking nut 4424 is used to rigidly contain ball-like coupler 4420 within first coupler 4415. While coupler 4420 is attached to, coupler 4415 of the previously implanted device 4305, the rod member 4410 that is positioned on the other end of device 4306 is affixed to bone screw assemblies that are each attached to the vertebral bone at the new level. Using this device and method, adjacent dynamic assemblies can be modularly coupled to one another across multiple vertebral levels.

FIG. 45 shows a cross-sectional view of a modular dynamic coupler 4305 and 4306 attached to one another across multiple vertebral levels. The interaction of cone member 4425 and cone receptacle member 4440 within each dynamic coupler is well illustrated. Flexion and extension movement of the vertebral bodies will produce various levels of movement between members 4425 and 4440. In specific, the device permits more translational and rotational movement between the vertebral bodies when they are in relative flexion than when they are in relative extension.

Figure 46B:
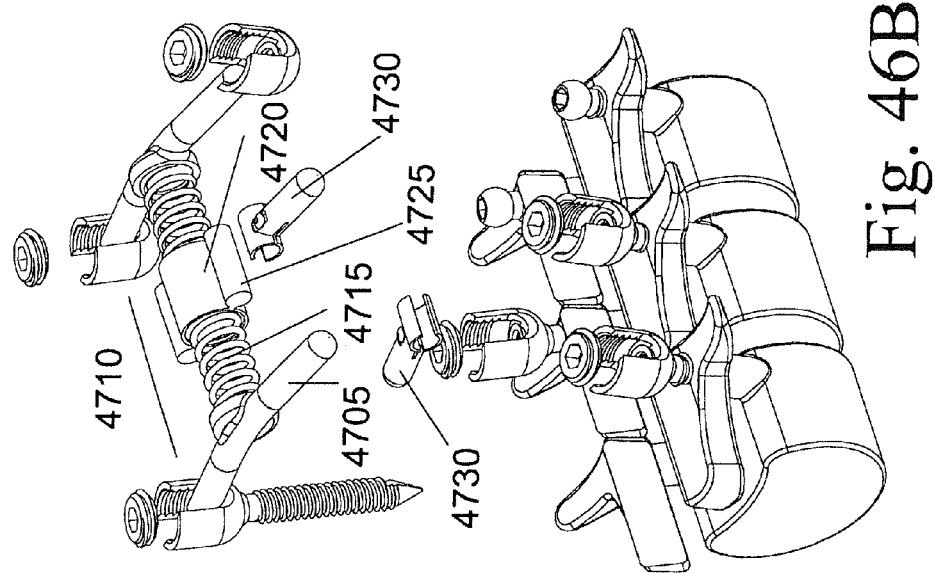
FIG. 46B shows an exploded view of the multilevel dynamic connector of FIG. 46A.
Figure 46A:
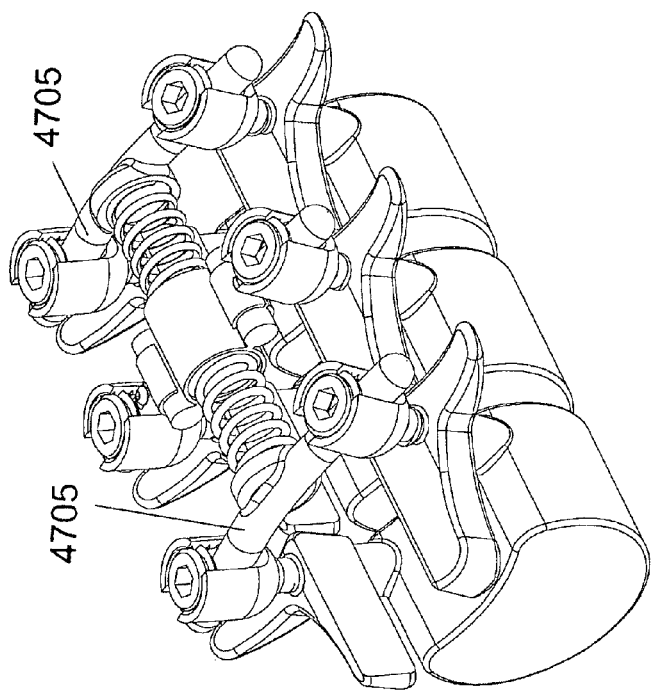
FIG. 46A shows an embodiment of a multilevel dynamic connector.

FIG. 46A shows an embodiment of a multi-level dynamic assembly in an assembled state. FIG. 47B shows an exploded view of the assembly. The device is adapted to link across three or more vertebral bones and includes a pair of cross-rods 4705, each of which links a pair of bone screw assemblies across the vertebral midline. The cross-rods 4705 are linked to one another via a linking member 4710 comprised of a pair of articulating members 4715 (such as springs) and a central member 4720. The central member 4720 has a pair of couplers 4725 that each couple to a movable cross-rod 4730. In use, the movable cross-rods 4730 are connected to bone screw assemblies that are attached to the intermediate vertebral bones. After attachment to the bone screw assemblies, the movable cross-rods 4730 are rigidly affixed onto their respective couplers 4725. Cross sectional views through the movable cross-rods 4730 are shown in FIGS. 48A and 48B.

FIG. 49A shows another embodiment of a multi-level dynamic assembly and FIG. 49B shows the device in an exploded state. As in the previous embodiment, the cross-member assembly is adapted to link at least three vertebral bones. The assembly includes a pair of end cross-rods 4905, each of which links a pair of bone screw assemblies across the vertebral midline. The cross-rods 4905 are linked to one another via a pair of linking member 4810 that couple to one another. Each linking member 4810 is comprised of an articulating member 4815 (such as malleable members and/or rigid bearing surfaces) and a central member 4820. The central member 4820 has a pair of couplers 4825 that each removably couple to a cross-rod 4830. The cross-rods 4830 can be cross-linked to a bone screw assembly implanted on an intermediate vertebral level(s) and then rigidly affixed to the central members 4820.

It should be appreciated that any of the dynamic features described herein of the dynamic couplers can be used within the dynamic bone screws and that the dynamic features of the dynamic bone screws can be used with the dynamic couplers.

Any of the embodiments disclosed in this application and/or their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any embodiment may also contain a bone or bone graft substitute component that is intended to fuse with the spinal bone and provide superior fixation of the device onto the spine. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, the prosthesis surface(s) that are adjacent to bone may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening.

Lastly, the illustrated embodiments and/or any component can also be entirely or partially made of a shape memory material or other deformable material.

The shown embodiments are illustrative and do not limit the scope of the invention. At a minimum, additional embodiments of the present invention can be created by one of ordinary skill using various combinations of the embodiments illustrated herein. It is understood that various modifications may be made without departing from the spirit and scope of the claims. Accordingly, other embodiments are within the scope of the following claims.

The invention claimed is:

1. A method for implantation of an orthopedic device assembly onto a first vertebral bone and a second adjacent vertebral bone, and into an intervening inter-vertebral disc space, said method comprising:
   identifying a first pedicle of said first vertebral bone;
   advancing a first anchor member of said assembly at least partially through said first pedicle and into a body of said first vertebral bone, said anchor member being separated from contact with said second vertebral bone;
   advancing a second member of said assembly at least partially through said first pedicle and into said body of said first vertebral bone;
   advancing a bone forming material through said first pedicle and into a cavity of said second member subsequent to said act of advancing said second member into said first vertebral bone, said bone forming material configured to form a bony fusion with at least a portion of said first vertebral bone;
   passing a distal segment of said second member into said intervening disc space, at least a portion of said distal segment being positioned to abut a surface of said second vertebral bone; and
   coupling a proximal segment of said second member to said anchor member.

2. The method of claim 1, wherein at least a portion of said anchor member configured to be advanced through said first pedicle and into said body of said first vertebral bone is threaded.

3. The method of claim 1, wherein said coupling of said proximal segment of said second member to said anchor member comprises a rigid coupling thereof.

4. The method of claim 1, wherein at least a portion of said second member comprises a curvilinear segment.

5. The method of claim 1, further comprising:
   movably coupling a housing member to a proximal aspect of said anchor member; and
   receiving an interconnecting member within said housing member.

6. The method of claim 5, further comprising transitioning a locking feature of said housing member to a locked state configured to substantially immobilize said interconnecting member with respect to said housing member.

7. The method of claim 5, further comprising coupling said interconnecting member to a second anchor attached to said second vertebral bone.

8. A method for stabilization of a spinal segment comprising a first vertebral bone, a second adjacent vertebral bone, and an intervening inter-vertebral disc space, said method comprising:
   identifying a first pedicle of said first vertebral bone;
   advancing a first member of said assembly at least partially through said first pedicle and into a body of said first vertebral bone, said anchor member, once implanted within said first vertebral bone, being separated from contact with said second vertebral bone;
   advancing a second member of said assembly at least partially through said first pedicle and into said first vertebral bone, said second member comprising a substantially curvilinear feature;
   passing a distal segment of said curvilinear feature of said second member into said intervening disc space, said distal segment being positioned to abut a bony surface of said second vertebral bone; and
   coupling a proximal segment of said curvilinear feature of said second member to said anchor member.

9. The method of claim 8, further comprising advancing a bone forming material through said first pedicle and into said first vertebral bone, said bone forming material configured to form a bony fusion with at least a segment of said first vertebral bone.

10. The method of claim 8, further comprising inserting a rod member into at least a portion of a housing associated with said first member, said rod member being configured to articulate with respect thereto via at least one articulation member.

11. The method of claim 10, wherein one or more dynamic features of said rod member permit movement along one or more portions of said rod member relative to one or more other portions thereof.

12. The method of claim 11, wherein said movement comprises at least one of: linear movement, curvilinear movement, pivoting, and rotating.

13. A method for implantation of an orthopedic device onto a living subject, said method comprising:
   advancing an anchor member of said device at least partially through a first pedicle of a first vertebral bone and into a body of said first vertebral bone, said anchor member being separated from contact with a second vertebral bone adjacent to said first vertebral bone;
   advancing a second member of said device at least partially through said first pedicle and into said body of said first vertebral bone, a distal segment of said second member entering an intervening disc space between said first and second vertebral bones and abutting a surface of said second vertebral bone;
   advancing a bone forming material through said first pedicle and into a cavity of said second member, said bone forming material configured to form a bony fusion with at least a portion of said first vertebral bone; and
   coupling a proximal segment of said second member to said anchor member.

14. The method of claim 13, wherein a portion of said anchor member which is configured to be advanced through said first pedicle and into said body of said first vertebral bone is threaded.

15. The method of claim 13, wherein said act of coupling said proximal segment of said second member to said anchor member comprises a rigid coupling thereof.

16. The method of claim 13, wherein at least a portion of said second member comprises a curvilinear segment.

17. The method of claim 13, further comprising:
   movably coupling a housing member to a proximal aspect of said anchor member; and
   receiving an interconnecting member within said housing member.

18. The method of claim 17, further comprising substantially immobilizing said interconnecting member with respect to said housing member via a locking feature of said housing member.

19. The method of claim 17, further comprising coupling said interconnecting member to a second anchor, said second anchor being attached to said second vertebral bone and separated from contact with said first vertebral bone.

20. The method of claim 17, wherein said interconnecting member comprises a rod member, said rod member being configured to articulate with respect to said anchor member via at least one articulation member.

21. The method of claim 20, wherein one or more dynamic features of said rod member permit movement along one or more portions of said rod member relative to one or more other portions thereof.

22. The method of claim 21, wherein said movement comprises at least one of: linear movement, curvilinear movement, pivoting, and rotating.

\* \* \* \* \*